(12) United States Patent
Liu

(10) Patent No.: US 11,453,869 B2
(45) Date of Patent: Sep. 27, 2022

(54) CATALYSIS DEACTIVATED ANGIOTENSIN-CONVERTING ENZYME 2 (ACE2) VARIANTS AND THEIR USES

(71) Applicant: AVIRMAX, INC., Hayward, CA (US)

(72) Inventor: Shengjiang Liu, Hayward, CA (US)

(73) Assignee: AVIRMAX, INC., Hayward, CA (US)

( * ) Notice: Subject to any disclaimer, the term of this patent is extended or adjusted under 35 U.S.C. 154(b) by 0 days.

(21) Appl. No.: 17/368,755

(22) Filed: Jul. 6, 2021

(65) Prior Publication Data

US 2022/0064618 A1    Mar. 3, 2022

Related U.S. Application Data

(60) Provisional application No. 63/093,788, filed on Oct. 19, 2020, provisional application No. 63/048,645, filed on Jul. 6, 2020.

(51) Int. Cl.
*C12N 9/48* (2006.01)
*C12N 15/86* (2006.01)

(52) U.S. Cl.
CPC .............. *C12N 9/485* (2013.01); *C12N 15/86* (2013.01); *C12Y 304/17023* (2013.01)

(58) Field of Classification Search
None
See application file for complete search history.

(56) References Cited

U.S. PATENT DOCUMENTS

| 2002/0048763 | A1 | 4/2002 | Penn et al. |
| 2007/0015271 | A1 | 1/2007 | Rosen et al. |
| 2007/0083334 | A1 | 4/2007 | Mintz et al. |
| 2021/0363512 | A1* | 11/2021 | Reiter ............... A61P 31/14 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession U6DXQ3. Jan. 22, 2014 (Year: 2014).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
International Search Report on PCT/US2021/40571, dated Feb. 2, 2022.
Iwanaga, N et al. BioRxiv, Jun. 15, 2020, p. 1-21.
Lei, C et al. Nature Commun, Apr. 24, 2020, V 11, 2010, p. 1-5.

* cited by examiner

*Primary Examiner* — Christian L Fronda
(74) *Attorney, Agent, or Firm* — Yong Chen; Lin Sun-Hoffman; Liu Chen & Hoffman LLP

(57) ABSTRACT

Angiotensin-converting enzyme 2 (ACE2) has been confirmed as a specific receptor for several (3 group coronaviruses include severe respiratory syndrome (SARS) coronavirus (SARS-CoV-1) and recently the causative agent for the World pandemic CoVID-19, SARS-CoV-2, and low pathogenic coronavirus of HCoV-NL63, a member in α-coronavirus group. Viral spike protein (S) of viral envelope is confirmed to bind to ACE2 as viral receptor to start a virus replication cycle. The present invention provides ACE2 and its mutants or variants, the viral or non-viral vectors thereof. Methods of treatment of viral infection of a human subject by using such mutants or variants are also provided.

5 Claims, 27 Drawing Sheets

Specification includes a Sequence Listing.

TM: transmembrane domain
Zinc-binding motif: H374E375XXH378....E402

| | | | Whole Protein |
|---|---|---|---|
| | Length | | 805 aa |
| ▲ | Molecular Weight | | 92,463.25 Da |
| ▲ | Extinction Coefficient (280 nm) | | 175,670 M⁻¹ cm⁻¹ |
| ▲ | Absorbance (280 nm, 0.1%) | | 1.90 |
| | Isoelectric Point (pI) | | 5.21 |
| | Charge at pH 7.0 ▼ | | −21.44 |

| | Amino Acid | | Number | Percent |
|---|---|---|---|---|
| A | Ala | Alanine | 51 | 6.34 |
| C | Cys | Cysteine | 8 | 0.99 |
| D | Asp | Aspartic Acid | 43 | 5.34 |
| E | Glu | Glutamic Acid | 56 | 0.90 |
| F | Phe | Phenylalanine | 39 | 4.84 |
| G | Gly | Glycine | 43 | 5.34 |
| H | His | Histidine | 16 | 1.99 |
| I | Ile | Isoleucine | 40 | 4.97 |
| K | Lys | Lysine | 47 | 5.84 |
| L | Leu | Leucine | 76 | 9.44 |
| M | Met | Methionine | 27 | 3.35 |
| N | Asn | Asparagine | 54 | 6.71 |
| P | Pro | Proline | 37 | 4.60 |
| Q | Gln | Glutamine | 38 | 4.72 |
| R | Arg | Arginine | 31 | 3.85 |
| S | Ser | Serine | 54 | 6.71 |
| T | Thr | Threonine | 39 | 4.84 |
| V | Val | Valine | 50 | 6.21 |
| W | Trp | Tryptophan | 23 | 2.86 |
| Y | Tyr | Tyrosine | 33 | 4.10 |

```
  1 msssswllls lvavtaaqst ieeqaktfld kfnheaedlf yqsslaswny ntniteenvq
 61 nmnnagdkws aflkeqstla qmyplqeiqn ltvklqlqal qqngssvlse dkskrlntil
121 ntmstiystg kvcnpdnpqe cllepglne imansldyne rlwaweswrs evgkqlrply
181 eeyvvlknem aranhyedyg dywrgdyevn gvdgydysrg qliedvehtf eeikplyehl
241 hayvraklmn aypsyispig clpahllgdm wgrfwtnlys ltvpfgqkpn idvtdamvdq
301 awdaqrifke aekffvsvgl pnmtqgfwen smltdpgnvq kavchptawd lgkgdfrilm
361 ctkvtmddfl tahhemghiq ydmayaaqpf llrnganegf heavgeimsl saatpkhlks
421 igllspdfqe dneteinfll kqaltivgtl pftymlekwr wmvfkgeipk dqwmkkwwem
481 kreivgvvep vphdetycdp aslfhvsndy sfiryytrtl yqfqfqealc qaakhegplh
541 kcdisnstea gqklfnmlrl gksepwtlal envvgaknmn vrpllnyfep lftwlkdqnk
601 nsfvgwstdw spyadqsikv rislksalgd kayewndnem ylfrssvaya mrqyflvkvn
661 qmilfgeedv rvanlkpris fnffvtapkn vsdiiprtev ekairmsrsr indafrlndn
721 sleflgiqpt lgppnqppvs iwlivfgvvm gvivvgivil iftgirdrkk knkarsgenp
781 yasidiskge nnpgfqntdd vqtsf (805)
```

Functional Regions of ACE2

1-17: Signal peptide
18..740 /region_name="Topological domain"
741..761 /region_name="Transmembrane region"
762..805 /region_name="Topological domain"

FIG. 3

ACE2-ECD — IgG1-Fc

```
 18 qst ieeqaktfld kfnheaedlf yqsslaswny ntniteenvq
 61 nmnnagdkws aflkeqstla qmyplqeiqn ltvklqlqal qqngssvlse dkskrlntil
121 ntmstiystg kvcnpdnpqe clllepglne imansldyne rlwaweswrs evgkqlrply
181 eeyvvlknem aranhyedyg dywrgdyevn gvdgydysrg qliedvehtf eeikplyehl
241 hayvraklmn aypsyispig clpahllgdm wgRfwtnlys ltvpfgqkpn idvtdamvdq
301 awdaqrifke aekffvsvgl pnmtqgfwen smltdpgnvq kavcHPtawd lgkgdfrilm
361 ctkvtmddfl tahhemghiq ydmayaaqpf llrnganegf heavgeimsl saatpkhlks
421 igllspdfqe dneteinfll kqaltivgtl pftymlekwr wmvfkgeipk dqwmkkwwem
481 kreivgvvep vphdetycdp aslfHvsndy sfirYytrtl yqfqfqealc qaakhegplh
541 kcdisnstea gqklfnmlrl gksepwtlal envvgaknmn vrpllnyfep lftwlkdqnk
601 nsfvgwstdw spyadqsikv rislksalgd kayewndnem ylfrssvaya mrqyflkvkn
661 qmilfgeedv rvanlkpris fnffvtapkn vsdiiprtev ekairmsrsr indafrlndn
721 sleflgiqpt lgppnqppvs DKTHTCPPCPAPELLGGPSVFLFPPKPKDTLMISR
TPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMH
EALHNHYTQKSLSLSPG
```

740 aa

The underlined region is human IgG1 Fc sequence

FIG. 4

|  | Whole Protein | Selection |
| --- | --- | --- |
| Length | 950 codons | |
| ▶ Molecular Weight | - | |
| ▶ Extinction Coefficient (280 nm) | - | |
| ▶ Absorbance (280 nm, 0.1%) | - | |
| Isoelectric Point (pI) | - | |
| Charge at pH 7.0 ▼ | - | |

| Amino Acid | | | Number | Percent | Number | Percent |
| --- | --- | --- | --- | --- | --- | --- |
| A | Ala | Alanine | 53 | 5.58 | | |
| C | Cys | Cysteine | 14 | 1.47 | | |
| D | Asp | Aspartic Acid | 50 | 5.26 | | |
| E | Glu | Glutamic Acid | 69 | 7.26 | | |
| F | Phe | Phenylalanine | 42 | 4.42 | | |
| G | Gly | Glycine | 46 | 4.84 | | |
| H | His | Histidine | 23 | 2.42 | | |
| I | Ile | Isoleucine | 35 | 3.68 | | |
| K | Lys | Lysine | 61 | 6.42 | | |
| L | Leu | Leucine | 88 | 9.26 | | |
| M | Met | Methionine | 27 | 2.84 | | |
| N | Asn | Asparagine | 60 | 6.32 | | |
| P | Pro | Proline | 57 | 6.00 | | |
| Q | Gln | Glutamine | 45 | 4.74 | | |
| R | Arg | Arginine | 34 | 3.58 | | |
| S | Ser | Serine | 65 | 6.84 | | |
| T | Thr | Threonine | 51 | 5.37 | | |
| V | Val | Valine | 63 | 6.63 | | |
| W | Trp | Tryptophan | 25 | 2.63 | | |
| Y | Tyr | Tyrosine | 41 | 4.32 | | |
| * | * | STOP | 1 | - | | |

Chain B, Angiotensin-converting enzyme 2 [Homo sapiens]

Sequence ID: 6M17_B Length: 814 Number of Matches: 1

See 5 more title(s) ⌄ Identical Proteins

Range 1: 27 to 749 GenPept Graphics ▼ Next Match ▲ Previous

| Score | Expect | Method | Identities | Positives | Gaps |
|---|---|---|---|---|---|
| 1509 bit(3906) | 0.0 | Compositional matrix adjust. | 719/723(99%) | 721/723(99%) | 0/723(0%) |

```
Query  1    QSTIEEQAKTFLDKFNHEAEDLFYQSSLASWNYNTNITEENVQNMNNAGDKWSAFLKEQS  60
Sbjct  27   ....................................                          86
Query  61   TLAQMYPLQEIQNLTVKLQLQALQQNGSSVLSEDKSKRLNTILNTMSTIYSTGKVCNPDN  120
Sbjct  87   ....................................                          146
Query  121  PQECLLLEPGLNEIMANSLDYNERLWAWESWRSEVGKQLRPLYEEYVVLKNEMARANHYE  180
Sbjct  147  ....................................                          206
Query  181  DYGDYWRGDYEVNGVDGYDYSRGQLIEDVEHTFEEIKPLYEHLHAYVRAKLMNAYPSYIS  240
Sbjct  207  ....................................                          266
Query  241  PIGCLPAHLLGDMWGREWTNLYSLTVPFGQKPNIDVTDAMVDQAWDAQRIFKEAEKFFVS  300
Sbjct  267  ....................................                          326
Query  301  VGLPNMTQGFWENSMLTDPGNVOKAVCHPTANDLGKGDFRILMCTKVTMDDFLTAHAQMG  360
Sbjct  327  .................................HE..                         386
Query  361  AIQYDMAYAAQPFLLRNGANEGFHQAVGEIMSLSAATPKHLKSIGLLSPDFQEDNETEIN  420
Sbjct  287  H..............E.....................                         446
Query  421  FLLKQALTIVGTLPFTYMLEKWRWMVFKGEIPKDQWMKKWWEMKREIVGVVEPVPHDETY  480
Sbjct  447  ....................................                          506
Query  481  CDPASLFHVSNDYSFIRYYTRTLYQFQFQEALCQAAKHEGPLHKCDISNSTEAGQKLFNM  540
Sbjct  507  ....................................                          566
Query  541  LRLGKSEPWTLALENVVGAKNMNVRPLLNYFEPLFTWLKDQNKNSFVGWSTDWSPYADQS  600
Sbjct  567  ....................................                          626
Query  601  IKVRISLKSALGDKAYEWNDNEMYLFRSSVAYAMRQYFLKVKNQMILFGEEDVRVANLKP  660
Sbjct  627  ....................................                          686
Query  661  RISFNFFVTAPKNVSDIIPRTEVEKAIRMSRSRINDAFRLNDNSLEFLGIQPTLGPPNQP  720
Sbjct  687  ....................................                          746
Query  721  PVS  723
Sbjct  747  ...  749
```

18 qst ieeqaktfld kfnheaedlf yqsslaswny ntniteenvq
61 nmnnagdkws aflkeqstla qmyplqeiqn ltvklqlqal qqngssvlse dkskrlntil
121 ntmstiystg kvcnpdnpqe cllepglne imansldyne rlwawe

| Lane | ACE2-ECD Variant | ID |
|---|---|---|
| 1 | AMI 080 | ACE2-ECD-Fc wt |
| 2 | AMI 090 | ACE2-vECD-Fc (E402Q) |
| 3 | AMI 081 | ACE2-vECD-Fc (E402Q,G466D) |
| 4 | AMI 082 | ACE2-vECD-Fc (E374Q,402Q) |
| 5 | AMI 083 | ACE2-vECD-Fc (E375Q,402Q) |
| 6 | AMI 084 | ACE2-vECD-Fc (E375Q, E402Q,H374A) |

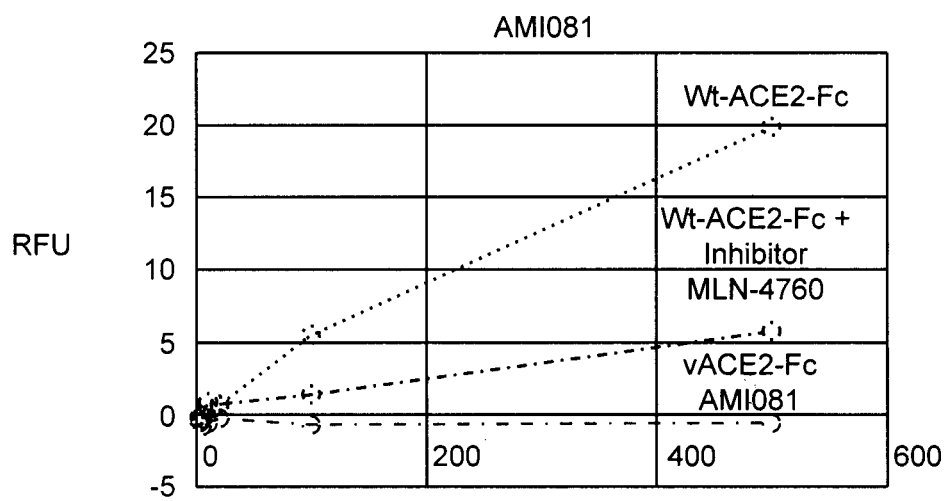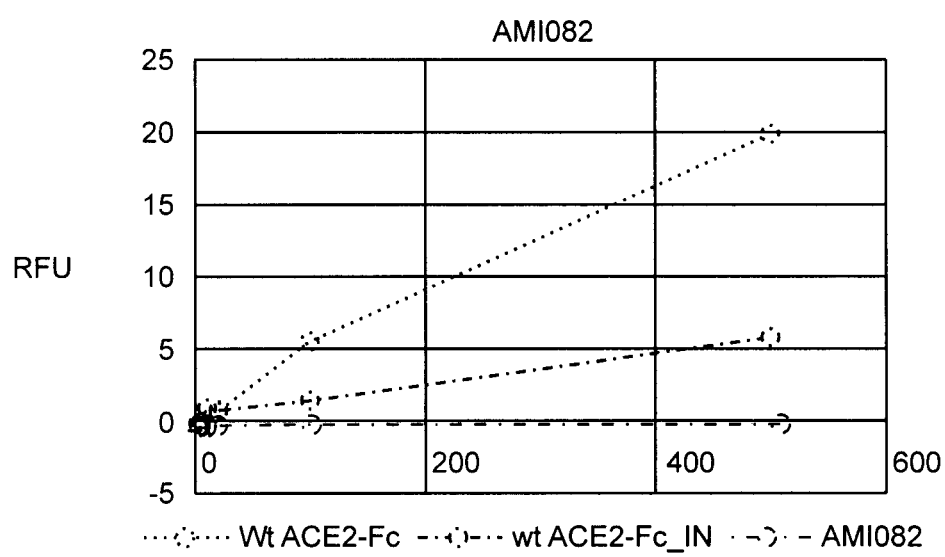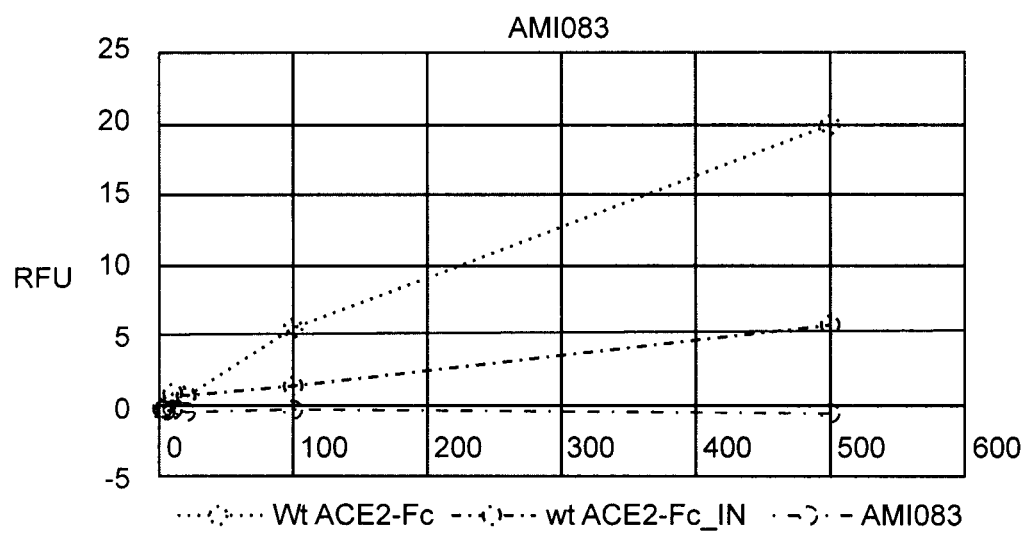
FIG. 15A

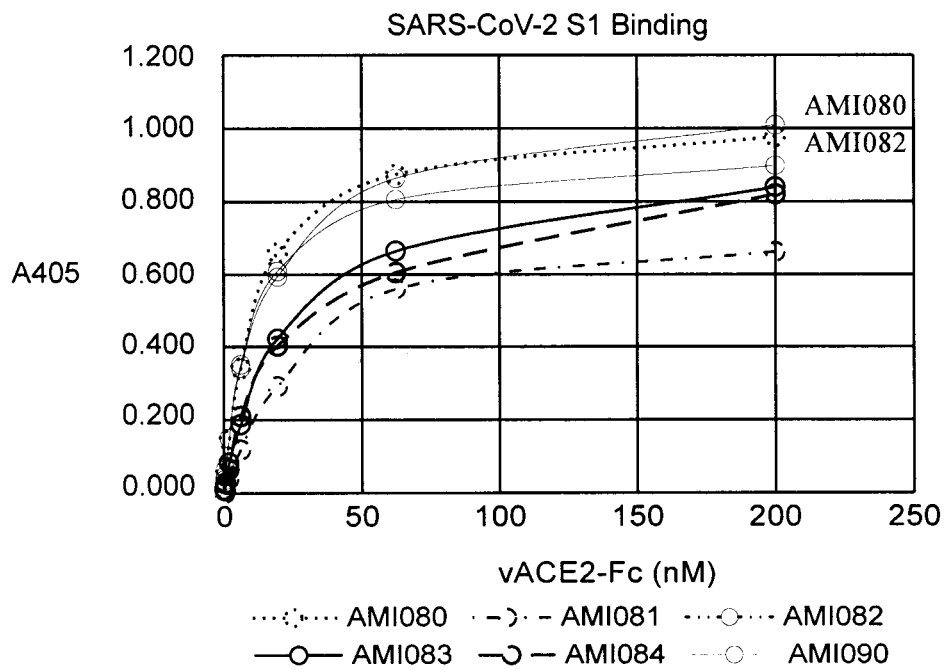
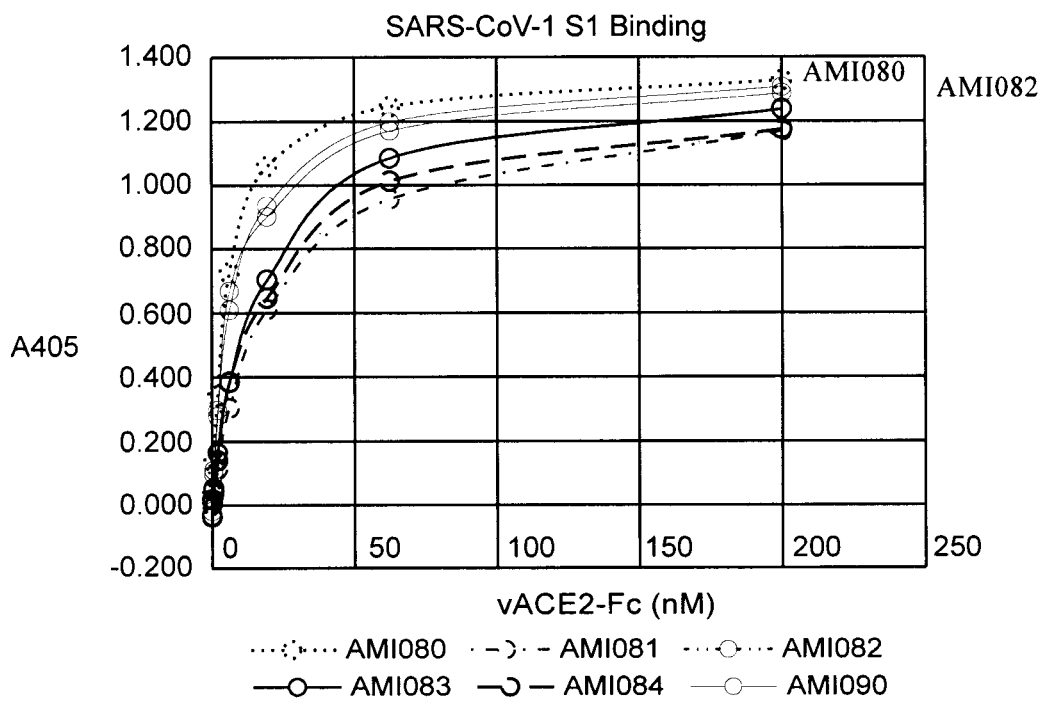
FIG. 16A

MERS-CoV S1 Binding

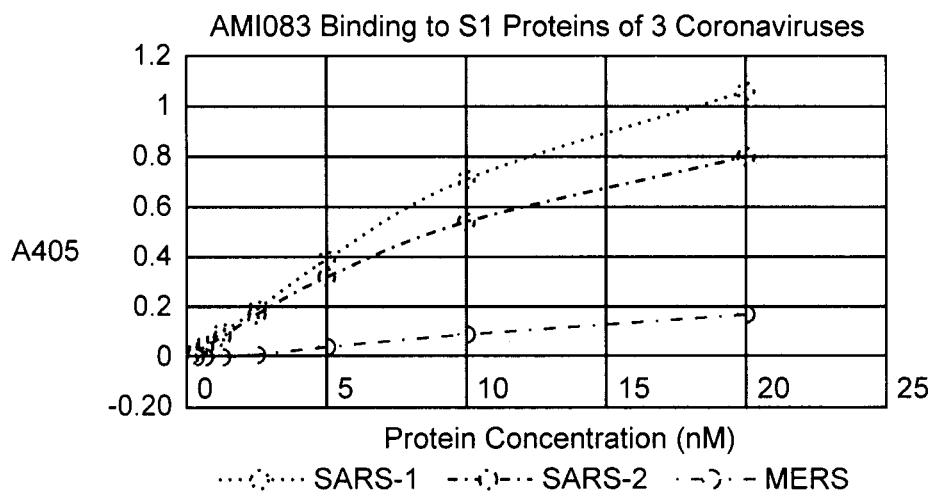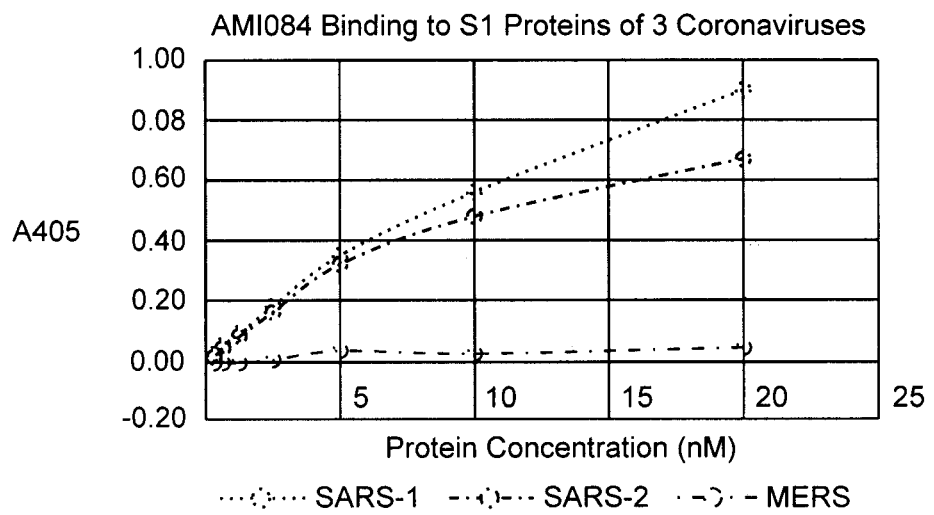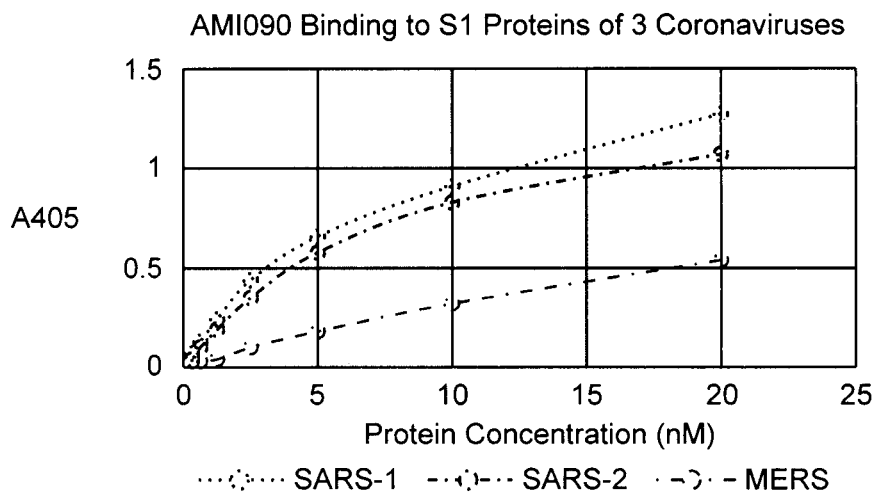
FIG. 17B

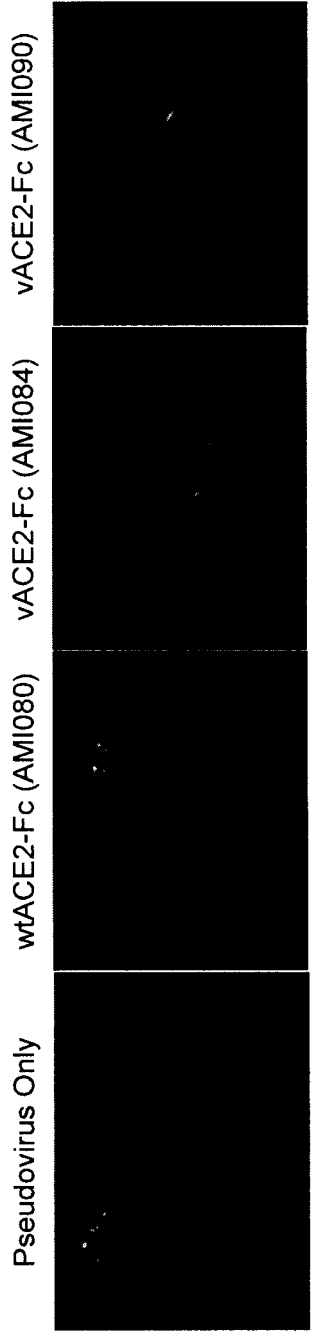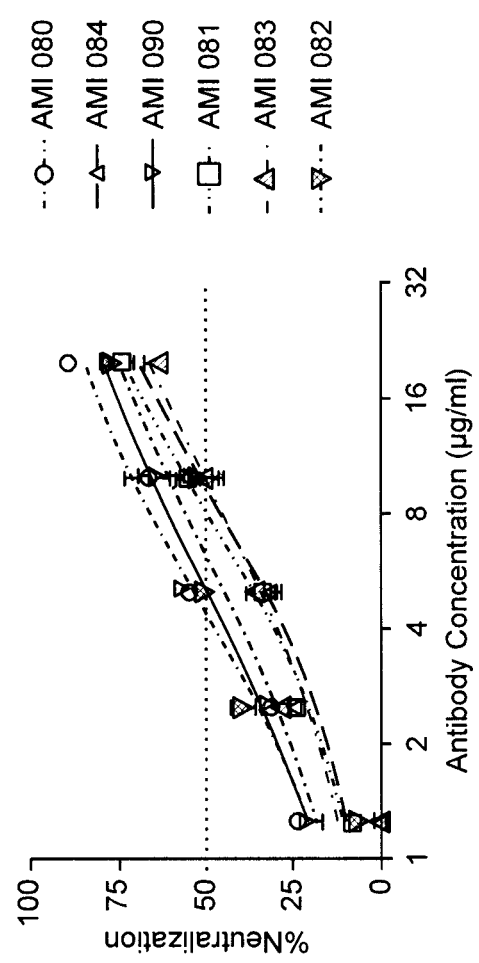
FIG. 19

Lane1. 20-067 5AMI089 ACE2-WT
Lane2. 20-057 5AMI082 (H374A-E402Q)
Lane3. 20-058 5AM1083 (E375-402Q)
Lane4. 20-059 5AMI084 (H374A-E375-402Q)
Lane5. 20-084 5AMI085 (H374A-E375Q)
Lane 6. 20-085 5AMI081 (E402Q-G466D)
Lane7. 20-086 5AMI090 (E402Q)
Lane8. 2GFP

CATALYSIS DEACTIVATED ANGIOTENSIN-CONVERTING ENZYME 2 (ACE2) VARIANTS AND THEIR USES

BACKGROUND

Human angiotensin converting-enzyme 2 (ACE2) is widely expressed on cell surfaces of various tissues, with the highest level detected in digestive tissues such as small intestine, colon, duodenum, gallbladder, heart muscle, airway, lung, and lower levels in other tissues. ACE2 is a peptidase that catalyzes removing of a C-terminal amino residue (Phe8) of angiotensin II into angiotensin 1-7 to maintain the balance of angiotensin II and angiotensin 1-7. It has a multiplicity and complexity of physiological roles that revolve around its several types of functions: a negative regulator of the renin-angiotensin system and facilitator of amino acid transport.

Another biological role of ACE2 has been confirmed as a specific receptor for several (3 group coronaviruses including severe respiratory syndrome (SARS) coronavirus (SARS-CoV-1) (Hofman et al, 2004, TRENDS in Microbiology, 12 (10), 2004; Jia, H. P. et al, 2005, J. Virol. 79(23), 14614-14621; Wang et al, 2008, Cell Research, 18:290-301) and a low pathogenic coronavirus of HCoV-NL63, a member in α-coronavirus group (Hofmann et al, 2005, PNAS, 102, 7988-7993). Very recently human ACE2 has been determined as the specific receptor for the causative agent for the World pandemic CoVID-19, SARS-CoV-2 (Wang et al., 2020, Cell, 181, 894-904; Zhao et al., 2020, Cell Host & Microbe, 28, 1-16). Binding of viral spike protein (S) of viral envelope to ACE2, the viral receptor, starts a virus replication cycle, causing host cell damage and viral transmission. The SARS-CoV-2 caused millions of patients seriously affected and died Worldwide. Control of virus binding to its receptor is a very important strategy to terminate COVID-19 prevalence.

SARS-CoV 1 and 2 virions bind their receptors of the host cells, the ACE2 ectodomain through the viral envelope spike protein (S1). The consequent entry into cytosol is by an acid dependent proteolytic cleavage of S protein by cathepsin, TMPRRS2 or other proteases followed by the fusion of viral and cell membranes. Viral genomic RNA (gRNA) is released from nucleocapsid. Synthesis of replicase using gRNA template takes place. This is a very important step what the replicase catalyzes the synthesis of genomic and subgenomic RNA fragments. Subgenomic RNA (sgRNA) is used for the synthesis of structural proteins that are packed together with gRNA template which is replicated using the negative stranded RNA (−RNA) in the intermediate. Following viral gRNA are replicated, structural proteins, S, E, & M are translated and translocated into the endoplasmic reticulum (ER) in ER-Golgi intermediate compartment (ERGIC) where mature virions are formed. Release of newly formed virus particles takes place after maturation complete. During the entire process angiotensin converting enzyme 2 (ACE2) plays a critical role in the replication cycle of SARS-CoV-1, SARS-CoV-2 and HCoV-NL63 respectively. Circulating ACE soluble receptor wild type or variant mutants, whether fused or not block SARS-CoV-1 and SARS-CoV-2 binding to its receptor on host cell surface. Therefore, viral infection and the disease are prevented and treated. In addition, ACE2 is important to regulate normal biological functions of many types of tissues/organs. It is confirmed critical to cardiovascular diseases, Gut Dysbiosis, inflammation, lung diseases, diabetic cardiovascular complications, kidney disorders. More information of ACE2 can be found in the review (Gheblawi et al, 2020, Circulation Research, 126: 1457-1475).

In controlling COVID-19, several approaches taken place include a. development vaccine using inactivated virus particles (inactivated vaccine), b. recombinant spike protein or message RNA (mRNA), c. recombinant virus receptor binding domain of spike protein (RBD) of the viral spike protein, d. recombinant human antibody cocktails etc. The challenges of the approaches reside in the low protection or no protection when viral spike mutation occurs naturally at the prevalence, transmission from human to human, human to animals or vs versus.

Since discovery of ACE2 as SARS-CoV receptor, no mutation is detected for the virus binding indicating a stable and specific target for the viral disease presentation and treatment. Initial efforts are made to use it as the virus decoy receptor for COVID-19. However, once ACE2 is directly administrated to a subject, as a virus-receptor blocker. Other functions of ACE2 are also introduced and thus may cause unnecessary activity associated with renin-angiotensin system (RAS).

SUMMARY OF INVENTION

The present invention provides an isolated extracellular domain (ECD) polypeptide of angiotensin converting enzyme 2 (ACE2) with one or more mutations that cause the loss of ACE2 catalytic activity (herein referred as ACE2-vECD) while retaining the binding activity to the viral spike protein, wherein the viral protein is spike protein of coronaviruses. In some embodiments, the present invention provides using a wild type ACE2 (herein referred as ACE2-ECD).

In one embodiment, the mutation that causes the loss of ACE2 enzymatic activity is located near N terminal region covering amino acid sequences from 361-410 wherein the region has a catalytic center.

In one embodiment, the N-terminal catalytic center comprise a motif of HEXXH . . . E. The position ranges from H374E375XXH378 . . . E402.

The catalytic region comprises one of more mutations that stops the enzyme catalytic activities.

The mutants of the present invention continue to connect with viral protein including but not limited to proteins from SARS-CoV 1, SARS-Cov2, MERS-CoV-1, and HCoV-NL63.

The present invention provides an isolated extracellular domain polypeptide of an angiotensin converting enzyme 2 (ACE2) with one or more mutations that cause loss of ACE2 enzyme catalytic activity, wherein the loss of enzymatic activity is caused by the loss of binding to a divalent metal ion. The divalent metal ion is selected from the group consisting of $Zn^{2+}$, $Co^{2+}$, and $Mn^{2+}$.

In one embodiment, the mutation is selected from the group consisting of positions H374, E375, H378, E402 and one or more combination thereof. These amino acid residues constitute the catalytic center of ACE2. The mutation would result in the loss of ACE2 binding to divalent metal ions, i.e. $Zn^{2+}$, $Co^{2+}$, and $Mn^{2+}$. The loss of metal ion binding activity makes the ACE2 an apoenzyme and loses its catalytic activity.

In another embodiment, the mutation sited in the R273, H345, H505, H515, P346 amino acid residues at the N-terminal half of the ACE2 extracellular domain may also result in the loss of enzyme activity but retain binding capacity to coronavirus spike proteins.

The present invention provides ACE-vECD mutations or variants that enhance binding affinity of ACE2-vECD to S1 protein of the viruses.

In one embodiment, an ACE2-ECD or ACE2-vECD variant is connected to human IgG1 Fc region. Therefore, the ACE2-ECD and ACE2-vECD variants become ACE2-ECD-Fc or ACE2-vECD-Fc variants. The present invention provides at least one or more mutations outside the catalytical region together with mutations in the catalytical region. It could be one or more mutations by one of the skilled in the art to decide to reach the result of deactivating the enzymatic activity of ACE2-vECD variants/mutants while enhancing the binding affinity of such an enzyme to the S1 protein. The example of the peptides included but not limited to the sequences in Table 1.

In yet another embodiment, the ACE2-ECD comprises SEQ ID NOs: 1, 2, 29 or ACE2-vECD comprises a polypeptide selected from the group consisting of SEQ ID:SEQ ID Nos: 3, 4, 5, 6, 7, 8, 9, 10, 11, 12, 13, 14, 15, 16, 17, 18, 19, 20, 21, 22, 23, 24, 25, 26, 27 and 28.

In one embodiment, the ACE2-vECD-Fc or their fusion proteins bind a virus whose native receptor is not ACE2.

The virus includes but not limited to SARS-CoV-1, SARS-CoV-2, MERS-CoV-1 and NL63.

The present invention provides a fusion protein comprising the isolated mutated ACE2 polypeptide further fused to a peptide or a polynucleotide or a small molecule at N or C terminal of mutated polypeptide to form a fusion protein, wherein the peptide or a polynucleotide or a small molecule is capable of binding to a receptor of an immune system associated cells such as lymphocyte, macrophages etc.

In another embodiment, such mutated sites are used for screening an agonist or an antagonist.

In one embodiment, the polynucleotide is a DNA or RNA.

In another embodiment, a small molecule is screen against the catalytic domain or against the mutant proteins as a drug screening system.

In another embodiment, the peptide is a ligand binding to the Fc binding receptor (FcγR) on immune cells such as lymphocytes. The lymphocytes are selected from group consisting of T cells, B cells, natural killer cells.

In one embodiment, the peptide is a Fc domain of human IgG antibodies (FcY).

In another embodiment, the ACE2 polypeptide with one or more mutations that can cause loss of ACE2 enzymatic activity while retaining the same or higher binding affinity to a viral protein comparing to the wild type ACE2 or the ACE2 existing in a subject, wherein such a subject can be a human being. The mutations can be within the catalytic region or outside catalytic region of the ACE2 polypeptide. Mutations can be two, three, four or five mutations on a polypeptide.

The present invention provides an isolated polynucleotide encoding a wild type ACE2, ACE2-ECD, mutated ACE2, or ACE-vECD.

In one embodiment, the wild type ACE2-ECD comprises SEQ ID NOs: 1, 2, 29.

In another embodiment, an ACE2-vECD variant or mutant comprises a polypeptide selected from the group consisting of SEQ ID Nos: 3, 4, 5, 6, 7, 8, 9, 10, 11, 12, 13, 14, 15, 16, 17, 18, 19, 20, 21, 22, 23, 24, 25, 26, 27, 28 and combinations thereof, or a combination with other selected amino acid mutants.

The present invention provides an isolated polynucleotide encoding a wild type, mutated, or mutated fusion protein ACE2, and ACE2-vECD is fused to an Fc.

The present invention provides an isolated polynucleotide encoding a wild type ACE2-ECD comprising SEQ ID NOs: 1, 2 or 29.

The present invention provides an isolated polynucleotide encodes a mutated ACE2-vECD selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27 and 28.

The present invention further provides an isolated wild type ACE2-ECD polynucleotide comprising SEQ ID Nos: 65 and 71.

The present invention further provides an isolated mutated ACE2-vECD polynucleotide comprise SEQ ID Nos: SEQ ID NOs: 64, 66, 67, 68, 69, 70, 72, 73, 74, 75, 76, 77, 78, 79, 80 or 81.

In one embodiment, the wild type ACE2-ECD polynucleotide encodes a polypeptide comprising SEQ ID NOs:1, 2, or 29.

In another embodiment, the mutated ACE2-vECD polynucleotide encodes a polypeptide comprising SEQ ID NO: 3, SEQ ID NO: 4, SEQ ID NO: 10, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO:25, SEQ ID NO:26, SEQ ID NO:27 or SEQ ID NO:28.

The present invention provides an isolated angiotensin converting enzyme 2 (ACE2) polypeptide with one or more mutations that cause the loss of ACE2 enzymatic activity, wherein such ACE2 polypeptide retains the same or higher binding affinity comparing to the wild type ACE2 against its binding partners.

In one embodiment, the increased/enhanced binding affinity is caused by mutations in the catalytic region of ACE2. In another embodiment, the mutations are in a region outside the catalytic region.

In yet another embodiment, the mutations comprise sites at K26, T27, L79, N330, H374, E375, H378, A386, A387, E402, G466, L795 and combinations of any two, three, four, five, six, seven or more mutations thereof.

In yet another embodiment, the mutation is selected from the group consisting of positions K26R, T27Y, L79S, N330F, H374A, E375Q, H378R, A386V, A387L, E402Q, G466D, L795H, and combinations of two, three, four, five, six, seven or more mutations thereof.

The polypeptide retains the same or higher binding affinity relative to the wild type ACE2 against its binding partners.

The polypeptide retains the same or higher binding affinity relative to the wild type ACE2 against its binding partners and sequences above may further fuse to a peptide or a polynucleotide or a small molecule at N or C terminal of mutated polypeptide to form a fusion protein, wherein the peptide is capable of binding to a receptor of an immune system associated cells.

In yet another embodiment, the binding affinity of the ACE2-vECD mutants or variant to MERS is higher than the affinity of wild type ACE2, or wild type ACE2-ECD. The affinity increase can be 150%, 200%, 300%, 400%, 500%, 600% or 700% more than the affinity of the wild-type thereof.

In one embodiment, the delivery of an expression vector comprises a polynucleotide encoding wild type ACE2, ACE2-ECD, ACE2 mutants, ACE-vECD or fusion protein thereof.

In one embodiment, the vector is selected from a viral vector or a non-viral vector.

The viral vector can comprise AAV, adenoviral, lentiviral, HSV (viral vector production using insect system, mammalian systems), wherein the AAV vector can be one or more of AAV1, AAV2, AAV3, AAV4, AAV5, AAV6, AAV7, AAV8, AAV9, AAV10, AAV11, AAV12, and any combination thereof.

The nonviral vector of can comprise a plasmid, a nanoparticle, a liposome, PEI derived or a colloid golden particle.

The present invention also provides a host cell comprising an expression vector of the mutated ACE2 or ACE2-vECD or the fusion proteins thereof, as described herein.

In one embodiment, the host cell can be selected from the group consisting of prokaryotic cells or eukaryotic cells. The prokaryotic cells can be bacterial cells, and the eukaryotic cells can be selected from group consisting of mammalian and nonmammalian cell lines. Examples of cells of mammalian origin include CHO, NS0, BHK-21.

In another embodiment, the present invention provides a composition comprising the polypeptide, fusion protein, vector/expression vector or host cell as described herein.

In one embodiment, the present invention provides a pharmaceutical composition comprising the polypeptide, fusion protein, vector/expression vector or host cell as described herein, and a pharmaceutical acceptable carrier.

In one embodiment, the administration of the pharmaceutical composition is via nasal, oral, airway, otic, subcutaneous, intramuscular, intravenous, or intrathecal.

The present invention also provides a vaccine composition comprising the expression vector of ACE2, wild type or ACE2 mutants or ACE2-vECD or ACE2-vECD-Fc as protein therapeutics or vector mediated particles, viral or nonviral vector.

The present invention provides a method for making a mutated polypeptide by synthesis or expressed in a host cell.

In one embodiment, the composition or the pharmaceutical composition is used to treat viral infection such as coronavirus infection including but not limited to alpha or beta coronavirus infection, SARS-CoV-1, SARS-CoV-2, MERS-CoV-1 and NL63.

In yet another embodiment, the present invention provides a method of preventing from viral infection or a prophylaxis treatment in a healthy subject by injecting a pharmaceutic composition of wild type ACE2, ACE2 mutants/ACE2-vECD or fusion proteins thereof as described herein, which includes but limited to ACE2-vECD-Fc.

The present invention provides a method for screening a compound, comprising a) contacting a population of transfected cells with mutated genes with a plurality of test agents in a high throughput screen for a time and under conditions that permit the test agent to affect ACE2 enzyme activity; and b) selecting a test agent if it caused a statistically significant increase or reduction in the level of ACE2 enzyme activity and binding affinity compared to pre-contact levels. The test agents can be either agonists or antagonists for ACE2.

In one embodiment, the contacting is in vitro or in vivo.

BRIEF DESCRIPTION OF THE DRAWINGS

FIG. 3 shows Human Angiotensin-converting Enzyme 2 Amino Acid Sequence.

FIG. 4 shows ACE2-ECD-Fc (Wildtype) sequence.

FIGS. 5A and 5B show a summary of amino acid composition (Wildtype) of a polypeptide of the present disclosure.

Figure 8:
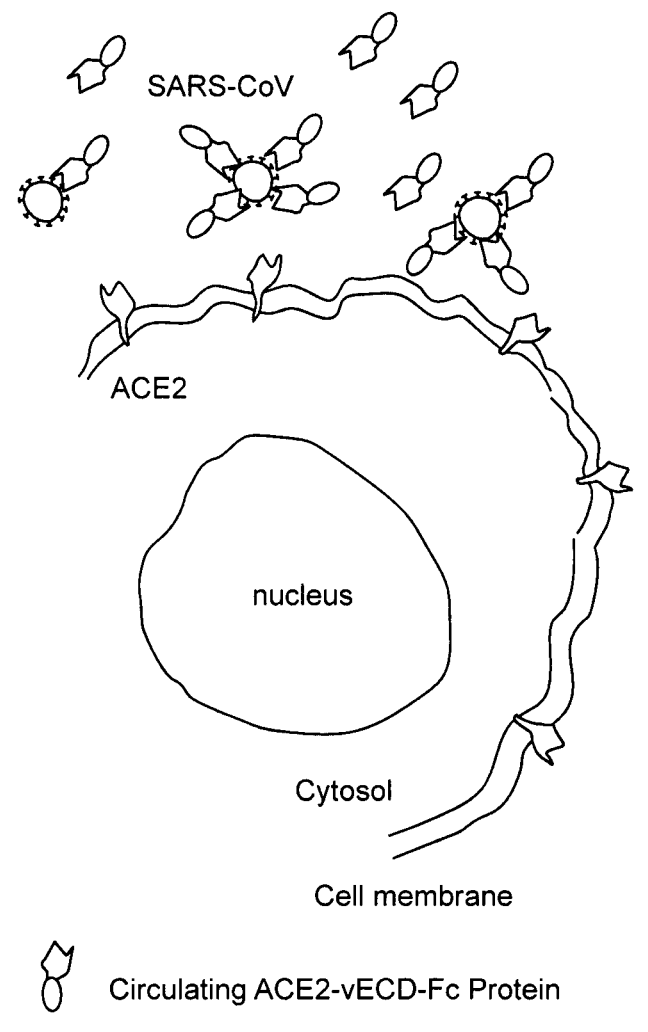

FIG. 8 is a diagram showing soluble ACE2-vECD-Fc binding to viral particles.

FIG. 9 shows ACE2 variant extracellular domain (ACE2-vECD) Blast search using fully substituted ECD as query sequence.

FIG. 10 shows the sequence of ACE2-vECD-Fc (with mutation(s) on ECD).

FIGS. 15A and 15B show assay results of certain polypeptides of the present disclosure, demonstrating ACE2 activity of ACE2-vECD-Fc variant was completely depleted.

FIG. 16A shows ELRLA assay results demonstrating ACE2-Fc variants bind to S1 Proteins of β-coronaviruses.

FIG. 16B shows binding curves indicating ACE2-Fc variants bind to SARS-CoV-2 B117 (N501Y) S1 Protein receptor Binding Domain (RBD) as detected by ELRLA.

FIGS. 17A and 17B show binding curves indicating ACE2-Fc and vACE2-Fc bind to Three S1 Proteins, as detected by ELISA.

FIG. 19 shows fluorescent microscopy images and assay demonstrating the neutralization of SARS-COV-2 S1 protein packed GFP-pseudovirus particles.

DETAILED DESCRIPTION

Definitions

Figure 1:
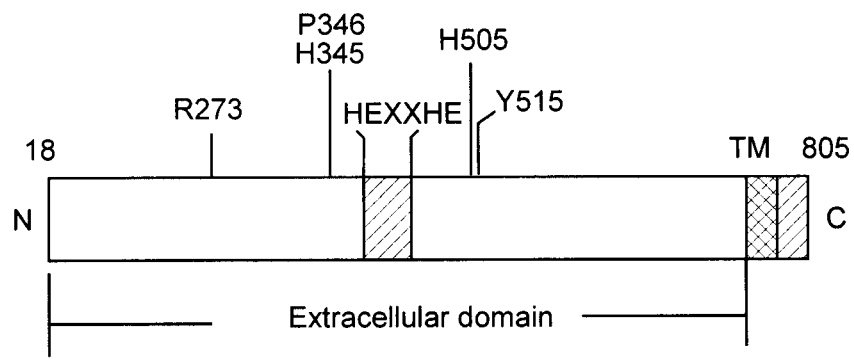
FIG. 1 is a diagram showing Human ACE2 Structure, which is a type I integral membrane carboxyl peptidase of 805 amino acids that contains one HEXXHE zinc-binding consensus sequence.

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Binding affinity: is the strength of the binding interaction between a single biomolecule (e.g. protein or DNA) to its ligand/binding partner (e.g. drug or inhibitor). Binding affinity is typically measured and reported by the equilibrium dissociation constant (KD), which is used to evaluate and rank order strengths of bimolecular interactions. The smaller the KD value, the greater the binding affinity of the ligand for its target. The larger the KD value, the weaker the target molecule and ligand are attracted to and bind to one another.

Binding region/binding center: the active site is the region of an enzyme where substrate molecules bind and undergo a chemical reaction. The active site consists of amino acid residues that form temporary bonds with the substrate (binding site) and residues that catalyzes a reaction of that substrate (catalytic site).

Catalytic activity: the increase in the rate of a specified chemical reaction caused by an enzyme or other catalyst under specified assay conditions.

Catalytic region or catalytic center: In general, this is the site on an enzyme that catalyzes the enzymatic conversion from its substrate(s) into product(s). The conversion is enzyme reaction. In ACE2, the catalytic center is formed by several amino acid residue and a divalent ion, for example, $Zn^{2+}$, $Co^{2+}$, and $Mn^{2+}$.

Effective amount as used herein means an amount effective at dosages and for periods of time necessary to enhance the level of ACE2.

Fc binding receptor A Fc receptor is a protein found on the surface of certain cells—including, among others, B lymphocytes, follicular dendritic cells, natural killer cells, macrophages, neutrophils, eosinophils, basophils, human platelets, and mast cells—that contribute to the protective functions of the immune system.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Modified: In the context of the present disclosure, a "modified" ACE2 polynucleotide or polypeptide sequence that comprises at least one nucleic acid or amino acid substitution, deletion or insertion compared to the wild type sequence (such as compared to the ACE2 wild type relative to ACE2 mutated type).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Pharmaceutically acceptable carrier: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

Preventing, treating or ameliorating a disease: "Preventing" a disease (viral infection) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding mutated ACE2) has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Treatment or treating: as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

Vaccine: is a composition that provides protection against a pathogenic infection (e.g., protozoal, viral, or bacterial infection), cancer or other disorder or treatment for a pathogenic infection, cancer or other disorder. Protection against a pathogenic infection, cancer or other disorder will either completely prevent infection or the tumor or other disorder or will reduce the severity or duration of infection, tumor or other disorder if subsequently infected or afflicted with the disorder. Treatment will cause an amelioration in one or more symptoms or a decrease in severity or duration. For purposes herein, a vaccine results from infusion of injection (either concomitantly, sequentially or simultaneously) of an antigen and a composition of matter produced by the methods herein. As used herein, amelioration of the symptoms of a particular disorder by administration of a particular composition refers to any lessening, whether permanent or temporary, lasting or transient that can be attributed to or associated with administration of the compositions of matter described herein.

Vaccination regimen means a treatment regimen wherein a vaccine comprising an antigen and/or any of the gene therapy-vectors (alone or in combination) described herein, as an adjuvant, is administered to a subject in combination, simultaneously, in either separate or combined formulations, or sequentially at different times separated by minutes, hours or days, but in some way act together to provide the desired enhanced immune response to the vaccine in the subject as compared to the subject's immune response in the absence of a composition in accordance with the invention.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

ACE2 Polypeptide and its Mutation and its Fusion Protein

ACE2 is a type I integral membrane carboxyl peptidase of 805 amino acid residues with its lead sequence, its mature protein with 788 amino acid residues that contains an extracellular domain of 725 amino acid residues, a short stretch of 21 amino acid residues of transmembrane domain and an intracellular domain of 44 amino acid residues. Within the extracellular domain, a "HE-XX-H-E" metal ion-binding consensus sequence, a motif of H374E375XXH378 . . . E402 is confirmed the catalytic essential sequences (FIG. 1). Specific sequence examples are listed in Table 1.

TABLE 1

Summary of Some Mutations of the Metal ion Binding Motif of ACE2 Catalytic Center

| | 361 ------------HExxH------------------------E-------410 |
|---|---|
| SEQ ID NO: 2 | ctkvtmddfl tahhemghiq ydmayaaqpf llrnganegf heavgeimsl |
| SEQ ID NO: 3 | ctkvtmddfl tahhemghiq ydmayaaqpf llrnganegf hQavgeimsl |
| SEQ ID NO: 4 | ctkvtmddfl tahAemghiq ydmayaaqpf llrnganegf hQavgeimsl |
| SEQ ID NO: 5 | ctkvtmddfl tahhemgAiq ydmayaaqpf llrnganegf hQavgeimsl |
| SEQ ID NO: 6 | ctkvtmddfl tahAemghiq ydmayaaqpf llrnganegf heavgeimsl |
| SEQ ID NO: 7 | ctkvtmddfl tahhemgAiq ydmayaaqpf llrnganegf heavgeimsl |
| SEQ ID NO: 8 | ctkvtmddfl tahAemgAiq ydmayaaqpf llrnganegf heavgeimsl |
| SEQ ID NO: 9 | ctkvtmddfl tahhQmghiq ydmayaaqpf llrnganegf hQavgeimsl |
| SEQ ID NO: 10 | ctkvtmddfl tahAQmghiq ydmayaaqpf llrnganegf hQavgeimsl |
| SEQ ID NO: 11 | ctkvtmddfl tahhQmgAiq ydmayaaqpf llrnganegf hQavgeimsl |
| SEQ ID NO: 12 | ctkvtmddfl tahAQmgAiq ydmayaaqpf llrnganegf hQavgeimsl |

TABLE 1-continued

Summary of Some Mutations of the Metal ion
Binding Motif of ACE2 Catalytic Center

```
SEQ ID NO: 13 ctkvtmddfl tahAQmghiq ydmayaaqpf llrnganegf heavgeimsl
SEQ ID NO: 14 ctkvtmddfl tahhQmgAiq ydmayaaqpf llrnganegf heavgeimsl
SEQ ID NO: 15 ctkvtmddfl tahAQmgAiq ydmayaaqpf llrnganegf heavgeimsl
```

The present invention is to mutate (substitution) at least one or more of amino acid residues, H, E, in the H374E375XXH378 . . . E402 metal ion binding motif, the only one metal ion binding motif in the extracellular domain of ACE2, and its technically ACE2 vECD.

The mutation of the metal ion binding motif depleted completely the endopeptidase activity ACE2 but maintains its specificity and affinity for coronavirus binding comparing to the wild type.

Total sequence of human ACE2 extracellular domain from N-terminus contains 725 amino acid residues (18-742 a.a.) (FIG. 3, Table 2), which is predicted with a molecule weight of 83596 Da with an extinction coefficient of 16140 M-1CM-1. The estimated pI is 5.26. Human "ACE2" herein is a glycoprotein and the molecular weight will be varying at some level with the glycosyation status. The extracellular domain (ECD) of human ACE2 amino acid sequence is shown in SEQ ID NO:1.

In another embodiment, the mutations on the ACE2 polypeptide comprise sites at K26, T27, L79, N330, H374, E375, H378, A386, A387, E402, G466, L795 and combinations of any two, three, four, five, six, seven or more mutations thereof. The mutation is select from the group consisting of positions K26R, T27Y, L79S, N330F, H374A, E375Q, H378R, A386V, A387L, E402Q, G466D, L795H, two, three, four, five, six, seven and more combination thereof.

TABLE 2

Summary of the amino acid composition of human wt-ACE2 (18-742).
Amino Acid Percents

| | |
|---|---|
| Alanine | 6.362% |
| Arginine | 3.873% |
| Asparagine | 6.777% |
| Aspartic acid | 5.394% |
| Cysteine | 1.107% |
| Glutamic acid | 7.469% |
| Glutamine | 4.979% |
| Glycine | 4.979% |
| Histidine | 2.213% |
| Isoleucine | 4.288% |
| Leucine | 9.682% |
| Lysine | 5.809% |
| Methionine | 3.458% |
| Phenylalanine | 4.841% |
| Proline | 4.841% |
| Serine | 6.224% |
| Threonine | 4.841% |
| Tryptophan | 2.905% |
| Tyrosine | 4.426% |
| Valine | 5.533% |

An ACE2 molecule contains one g-atom of zinc per mole of protein. Zinc ion, the cofactor for the enzyme, is essential to the catalytic activity of ACE and ACE2. ACE2 is a critical member of the renin angiotensin system important in regulating heart function and blood pressure homeostasis. Use of chelators such as EDTA completely deactivate the enzyme by removing the zinc ion from the catalytic center to form zinc-free apoenzyme. Spiking metal-free apoenzyme solution with Zn 2+, Co 2+, or Mn2+resulted in restoration of metalloenzyme activity. The activities of the metalloenzymes follow the order Zn2+greater than C2+or greater than Mn2+. However, addition of metal ion —Fe2+, Ni2+, Cu2+, Cd2+, and Hg2+fail to restore activity. The protein binds Zn 2+more firmly than it does Co2+or Mn2+.

Human ACE2 has 6 predicted N-linked glycosylation sites and they are asparagine (N) residues at positions of N53, N90, N104, N332, N432 and N546. In mammalian and human cells, the carbohydrates of the membrane proteins are sialylated. At least one of these sialic acid moieties of the glycosylated asparagine residues contribute to coronavirus binding. The natural substrate of ACE2 is angiotensin II, a short peptide molecule. The crystal structure studies indicated that these residues are not involved in the catalysis of converting of angiotensin II into angiotensin 1-7 (Wang, Q. H. et all, 2020).

Figure 2:
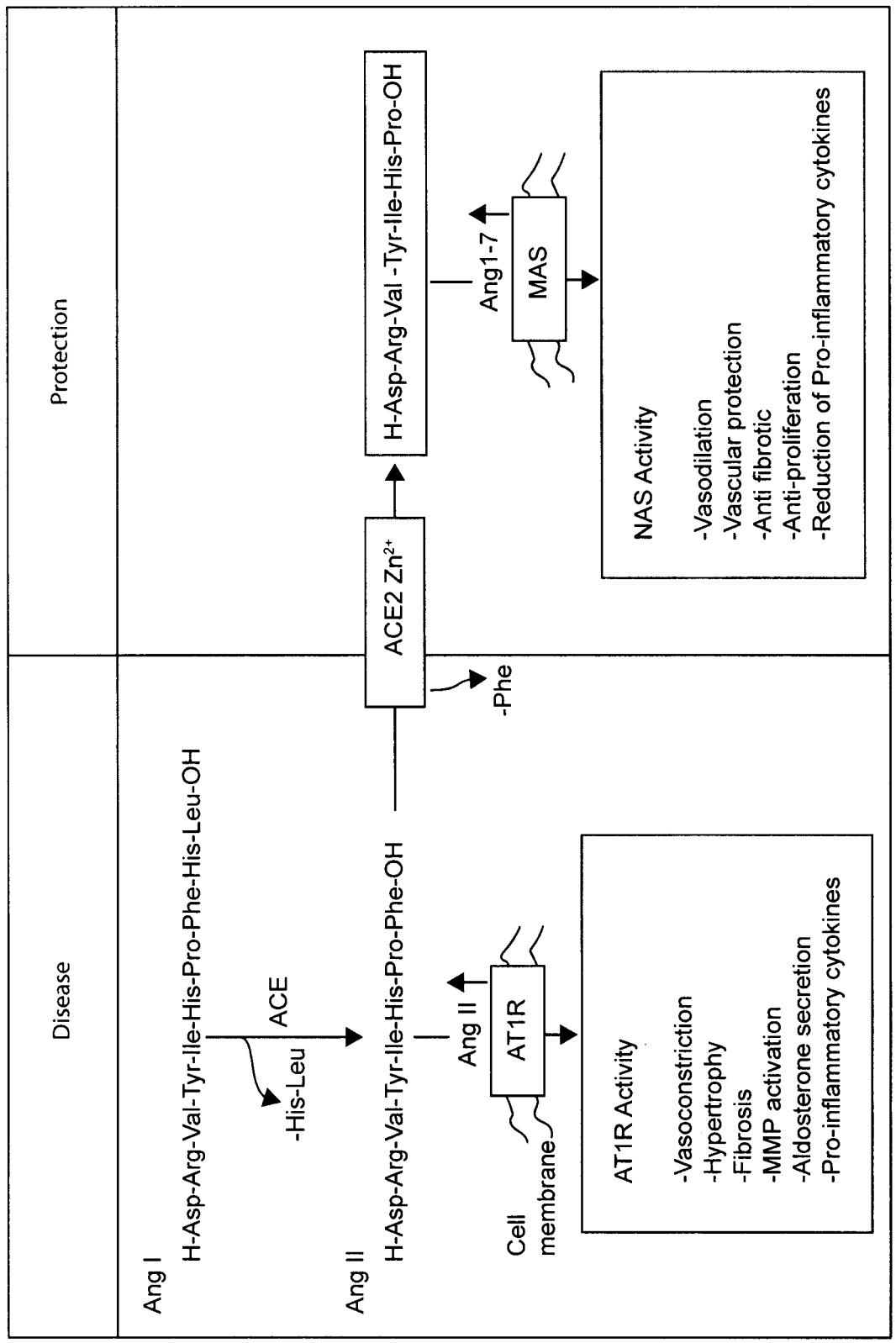
FIG. 2 is a diagram of ACE2 biological activities.
Figure 5A:
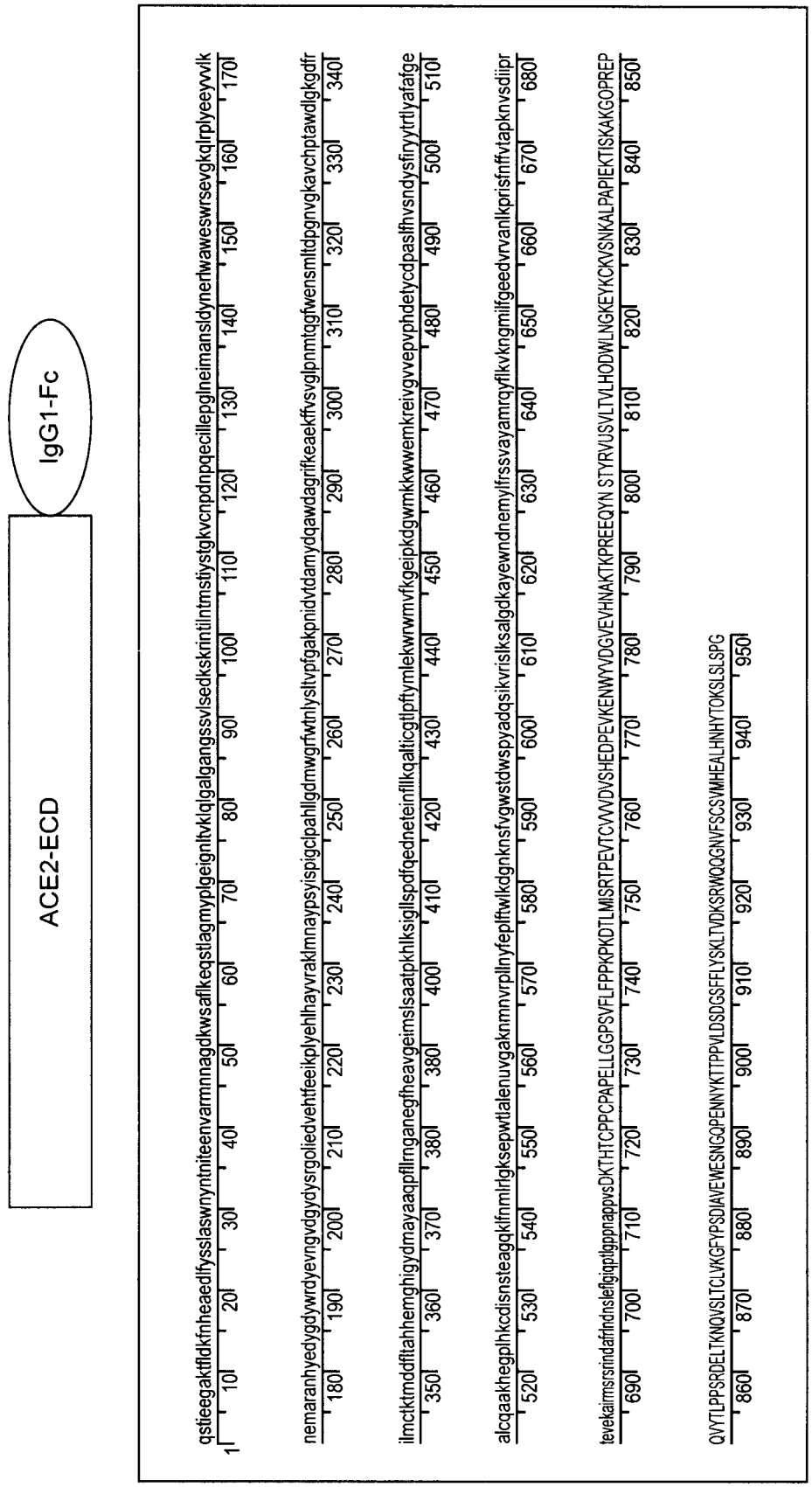

Human angiotensin I (Ang I) I is a short peptide of 10 amino acid residues, H-Asp-Arg-Val-Tyr-Ile-His-Pro-Phe-His-Leu-OH (single lettered as DRVYIHPFHL). Ang I is cleaved to Ang II by the angiotensin-converting enzyme (ACE) or non-angiotensin-converting enzyme-dependent conversion of Ang I to Ang II. Human chymase efficiently converts the 10-mer Ang I to the 8-mer hormone Ang II by splitting the Phe8-His9 bond in Ang I, becoming H-Asp-Arg-Val-Tyr-Ile-His-Pro-Phe—or DRVYIHPF). Ang II is further cleaved by a carboxyl peptidase (exopipetidase) to remove the C-terminal Phe (F) residue, becoming Ang1-7. The biochemical reactions and biological functions of Ang I, Ang II and Ang1-7 are summarized in FIG. 2. Under normal conditions, the activity of ACE2 is well balanced via physiological and biochemical regulations. Changes in the balance would cause diseased conditions. In the case of SARS-COV-2 or SARS-COV-1 infection, host cell surface ACE2 molecules are used up by the virus particles. The ACE2 depleted phenomenon is manifested.

While using wild type ACE2 decoy receptor to treat SARS-COV-2 infection, dosing high levels of ACE2 protein preparation could result in a significant increase of enzyme that catalyzes the conversion of Ang II into Ang 1-7 and possibly lead to depletion of Ang II. There may be possible adverse effects due to significant reduction of Ang II.

In particular examples, the mutated ACE2 sequence comprises sequences are summarized in Table 3:

TABLE 3
Summary of Mutants and Their Fc Fusion Proteins

| Sequence ID. | Amino acid mutation | Protein Sequence |
|---|---|---|
| AMI074 | G466D | CTKVTMDDFLTAHHEMGHIQYDMAYAAQPFLLRNGANEGFHEAVGEIMSL SAATPKHLKSIGLLSPDFQEDNETEINFLLKQALTIVGTLPFTYMLEKWR WMVFKD (SEQ ID NO: 16) |
| AMI080 | ACE2-WT | CTKVTMDDFLTAHHEMGHIQYDMAYAAQPFLLRNGANEGFHEAVGEIMSL (SEQ ID NO: 2) |
| AMI081 | E402Q, G466D | CTKVTMDDFLTAHHEMGHIQYDMAYAAQPFLLRNGANEGFHQAVGEIMSL SAATPKHLKSIGLLSPDFQEDNETEINFLLKQALTIVGTLPFTYMLEKWR WMVFKD (SEQ ID NO: 17) |
| AMI082 | H374A, E402Q | CTKVTMDDFLTAHAEMGHIQYDMAYAAQPFLLRNGANEGFHQAVGEIMSL (SEQ ID NO: 4) |
| AMI083 | E375, 402Q | CTKVTMDDFLTAHHQMGHIQYDMAYAAQPFLLRNGANEGFHQAVGEIMSL (SEQ ID NO: 18) |
| AMI084 | H374A, E375Q, E402Q | CTKVTMDDFLTAHAQMGHIQYDMAYAAQPFLLRNGANEGFHQAVGEIMSL (SEQ ID NO: 10) |
| AMI085 | E374A, E375Q | CTKVTMDDFLTAHAQMGHIQYDMAYAAQPFLLRNGANEGFHEAVGEIMSL (SEQ ID NO: 19) |
| AMI089 | WT in AAV5 | CTKVTMDDFLTAHHEMGHIQYDMAYAAQPFLLRNGANEGFHEAVGEIMSL (SEQ ID NO: 2) |
| AMI090 | E402Q | CTKVTMDDFLTAHHEMGHIQYDMAYAAQPFLLRNGANEGFHQAVGEIMSL (SEQ ID NO: 3) |
| AMI121 | L79S, N330L, H374A, H378R, A386V,, E402Q | L79S . . . N330L . . . CTKVTMDDFLTAHAEMGRIQYDMAYVAQPFLLRNGANEGFHQAVGEIMSL (SEQ ID NO: 20) |
| AMI122 | N330L, H374A, H378R, A386V, E402Q | N330L . . . CTKVTMDDFLTAHAEMGRIQYDMAYVAQPFLLRNGANEGFHQAVGEIMSL (SEQ ID NO: 21) |
| AMI123 | T27Y, L79S, N330F, H374A, A387L, E402Q | T27Y . . . L79S . . . N330F . . . CTKVTMDDFLTAHAEMGHIQYDMAYALQPFLLRNGANEGFHQAVGEIMSL (SEQ ID NO: 22) |
| AMI124 | T27Y, L79S, N330F, H374A, H378R, A387L, E402Q | T27Y . . . L79S . . . N330F . . . CTKVTMDDFLTAHAEMGRIQYDMAYALQPFLLRNGANEGFHQAVGEIMSL (SEQ ID NO: 23) |
| AMI125 | H374A, H378A, A387L, E402Q | CTKVTMDDFLTAHAEMGAIQYDMAYALQPFLLRNGANEGFHQAVGEIMSL (SEQ ID NO: 24) |
| AMI126 | H374A, H378R, A387L, E402Q | CTKVTMDDFLTAHAEMGRIQYDMAYALQPFLLRNGANEGFHQAVGEIMSL (SEQ ID NO: 25) |
| AMI127 | H374A, A387L, E402Q | CTKVTMDDFLTAHLEMGHIQYDMAYALQPFLLRNGANEGFHQAVGEIMSL (SEQ ID NO: 26) |
| AMI128 | K26R, H374A, A387L, E402Q | K26R . . . CTKVTMDDFLTAHAEMGHIQYDMAYALQPFLLRNGANEGFHQAVGEIMSL (SEQ ID NO: 27) |
| AMI129 | H374L, H378R, A387L, E402Q | CTKVTMDDFLTAHLEMGRIQYDMAYALQPFLLRNGANEGFHQAVGEIMSL (SEQ ID NO: 28) |

According to the characteristics of ACE2 catalytic center, at least one or more than one mutation, substitution, deletion or alanine replacement could result into complete or drastic depletion of its activity. This is the fundamental theory lay inside of the invention for using full length of enzyme molecule for binding without its catalytical activity. Such usage could be but not limited to binding viruses, i.e., SARS-CoV1, SARS-CoV-2, MERS-CoV or the emerging coronaviruses etc.

Figure 6:
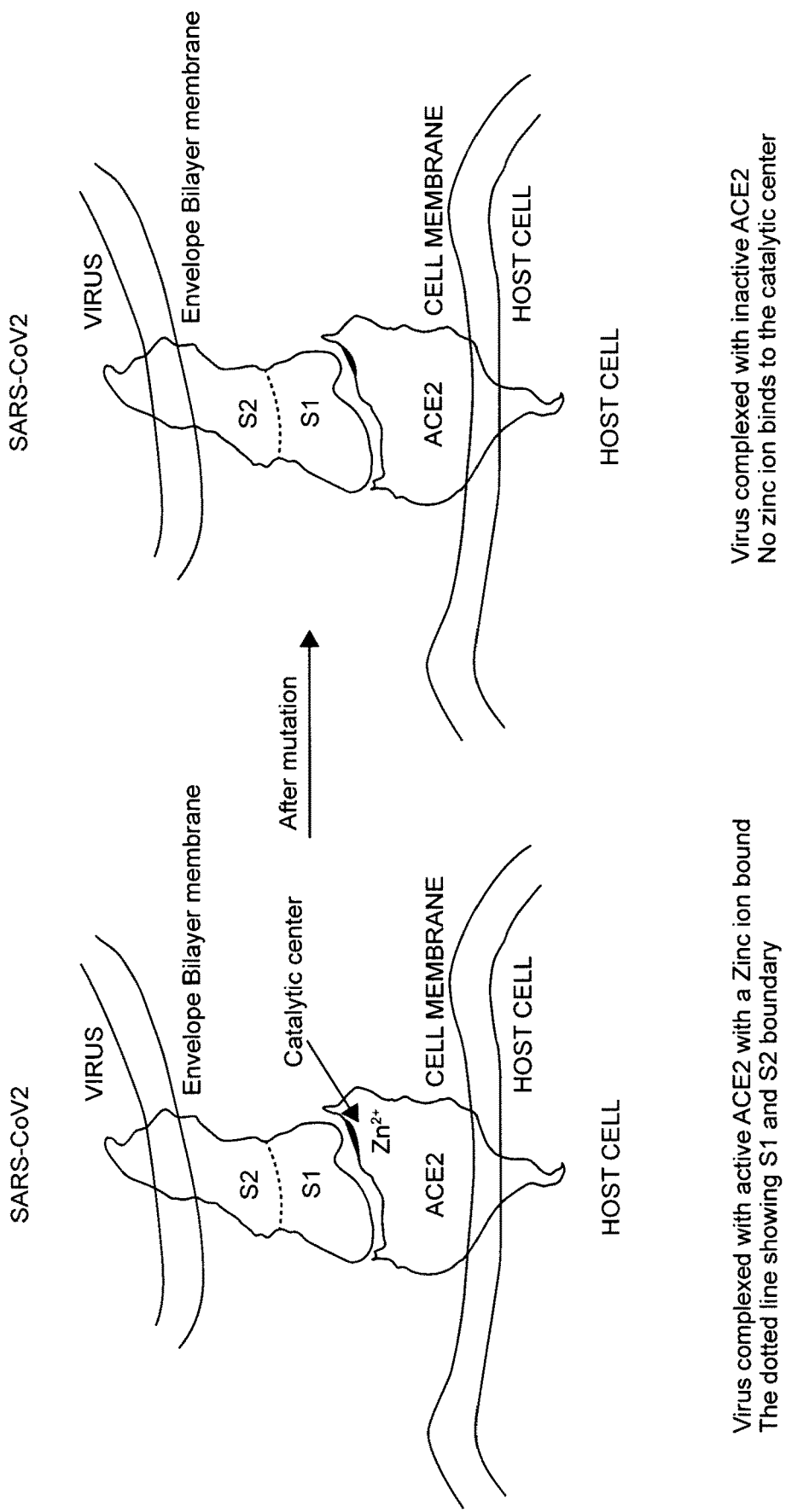
FIG. 6 is a diagram illustrating loss of ACE2 enzyme activity by mutating Zinc ion binding site.
Figure 7:
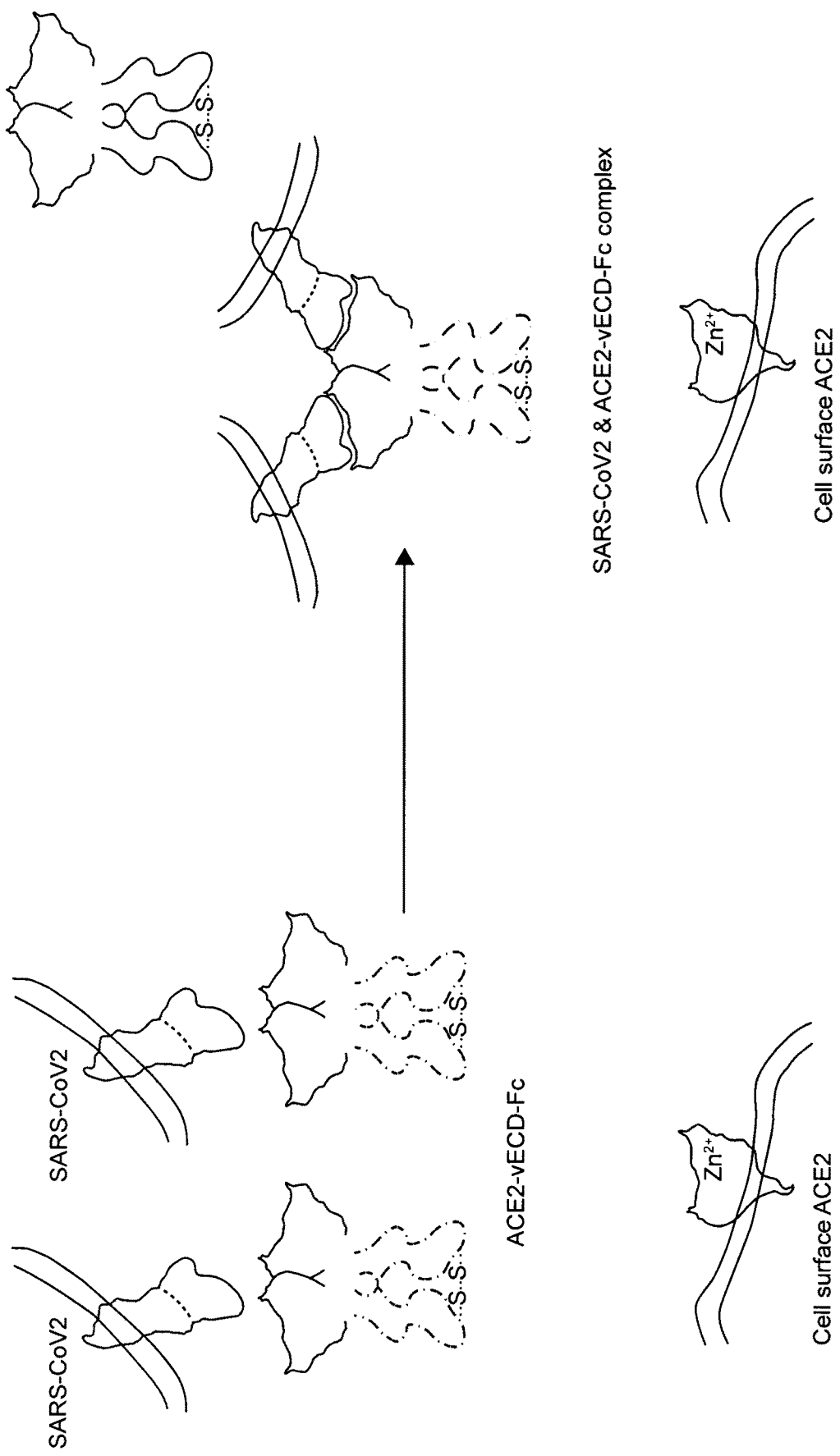
FIG. 7 is a diagram showing that ACE2-vECD-Fc binds virus particles.

In additional to the metal ion binding motif, there are several critical amino acid residuals contribute to the enzymatic activity. The key residual arginine 273 (R273) of ACE2 contributes to substrate recognition via a salt bridge and a hydrogen bond. Removal of this Arg273 abolished the enzymatic activity. The residue histidine 345 (H345) of ACE2 stabilizes substrate-enzyme intermediate and Histidine 505 also contributes significantly, removal of His505 resulted in 300-fold reduction of enzyme activity. Other residues are also important to the enzyme activity such as proline 346 (P346) and histidine 515 (H515). Based on the descriptions above to mutate the residues in the metal ion binding motif, complete abolishment of enzyme activity is able to be achieved by mutation of one and/or more than one of these residues, R273, H345, P346, H505, H515 in ACE2 molecule. (Nicola E. Clarke et al, Handbook of Proteolytical Enzymes, chapter 100, pp 499-504, 3rd eds, 2013). For this reason, it is naturally to believe that mutation of residual arginine 273 (R273) of ACE2 could also lead to a significant reduction or depletion of enzyme activity because it contributes positive charge of the R to the salt bridge to substrate-enzyme intermediate.

ACE2 variants or mutants may be used in methods of the invention. Changes which result in production of a chemically equivalent or chemically similar amino acid sequence are included within the scope of the invention. Polypeptides having sequence identity to ACE2 catalytic regions are tested to ensure that they are suitable for use in the methods of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids, which have similar chemical properties as the replaced amino acids. The invention includes sequences where conservative substitutions are made that do not destroy compound activity.

Polypeptides comprising one or more d-amino acids are contemplated within the invention. Also contemplated are polypeptides where one or more amino acids are acetylated at the N-terminus. Those with skill in the art recognize that a variety of techniques are available for constructing polypeptide mimetics with the same or similar desired compound activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

The invention also includes hybrids and polypeptides, for example where a nucleotide sequence is combined with a second sequence.

The invention also includes methods of using polypeptide fragments of ACE2 which may be used to confer compound activity if the fragments retain activity.

The invention also includes polypeptides and fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 or 250 to 500 amino acids. Fragments may include sequences with one or more amino acids removed, for example, C-terminus amino acids in a compound sequence.

Particularly, The ACE2 polypeptide has a binding affinity enhanced at the mutated catalytic sites. In one embodiment, the binding affinity of the ACE2-vECD mutants or variant to MERS is higher than the affinity of wild type ACE2, or wild type ACE2-ECD. The affinity is 150%, 200%, 300%, 400%, 500%, 600% or 700% more than the binding affinity thereof In another embodiment, ACE2 polypeptide retains the same or higher binding affinity comparing to the wild type ACE2 against its binding partners.

In another embodiment the increase/enhanced of binding affinity is caused by mutations outside catalytic region. Some examples of mutations are in the Table 3.

ACE2 Polypeptide and its Fusion

The present invention provides a fusion protein of extracellular domain of 723 amino acid residues (ACE-vECD) after mutation process being fused to human IgG (for example, IgG1 Fc or IgG4) Fc domain via N-terminal or C-terminal fusion in the format of ACE2-vECD-Fc (FIG. 4).

Once the ACE2 portion of the ACE2-Fc molecule binds to its specific virus, the Fc portion can exert its biological function such as complement activation and Fc receptor positive cells to attack the complex.

The composition of the ACE2 ECD-Fc and ACE2 vECD-Fc variants are engineered as the ACE extracellular domain is fused to either the N-terminus or c-terminus of human IgG1 Fc fragment. The example of the wild type ACE2 derived Fc fusion protein molecular analysis of ACE2-ECD-Fc is shown in the following (FIG. 4, FIG. 5A, 5B, Table 4):

TABLE 4

| Molecular Analysis of ACE2-ECD-Fc | |
|---|---|
| Results | |
| Protein Name | Not Identified |
| Molecular weight | 108.998 kDa |
| Extinction coefficient | 196410M$^{-1}$ cm$^{-1}$ |
| Amino Acid Percents | |
| Alanine | 5.585% |
| Arginine | 3.683% |
| Asparagine | 6.322% |
| Aspartic acid | 5.269% |
| Cysteine | 1.475% |
| Glutamic acid | 7.271% |
| Glutamine | 4.742% |
| Glycine | 4.847% |
| Histidine | 2.424% |
| Isoleucine | 3.688% |
| Leucine | 9.273% |
| Lysine | 6.428% |
| Methionine | 2.845% |
| Phenylalanine | 4.426% |
| Proline | 6.006% |
| Serine | 6.849% |
| Threonine | 5.374% |
| Tryptophan | 2.634% |
| Tyrosine | 4.32% |

The mutated ACE2-vECD or ACE-vECD-Fc can include modifications at additional residues so long as the protein retains enzymatic SARS-COV binding activity while depleting the divalent metal ion bind activity (FIG. 6). For example, the mutated ACE2 can include substitutions at other residues in the HEXXE region, such residues include positions H374, E375, H378, E402 of the ACE2 ECD. Once ACE2 lost its catalysis function, it becomes a binder of coronaviruses that stop viral infection and transmission (FIG. 7 and FIG. 8). (set forth as SEQ ID NO: 1 as wild type ACE2 ECD).

The present invention provides a nucleic acid molecule that encodes various ACE2 mutants, or ACE2-vECD (FIG. 9 and FIG. 10).

In some examples, the nucleic acid molecule encodes a wild type ACE2, mutated ACE2/ACE2-vECD variants, or its fusion protein thereof having an amino acid sequence at least 80%, at least 85%, at least 90%, at least 95%, at least 96%, at least 97%, at least 98% or at least 99% identical to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28 or 29.

In particular examples, the polypeptide of the ACE2-vECD comprises or consists of SEQ ID NOs: 3, 4, 5, 6, 7, 8, 9, 10, 11, 12, 13, 14, 15, 16, 17, 18, 19, 20, 21, 22, 23, 24, 25, 26, 27 or 28.

In particular examples, the polypeptide of the wild type ACE2-ECD comprises or consists of SEQ ID NOs: 1, 2 or 29.

In a particular example, the polynucleotide of wild type ACE2-vECD comprises or consists of SEQ ID Nos: 65 or 71.

In non-limiting examples, the isolated polynucleotide comprises or consist of any nucleotide sequence of SEQ ID NO: 64, 65, 66, 67, 68, 69, 70, 71, 72, 73, 74, 75, 76, 77, 78, 79, 80 or 81;

In another example, the isolated polynucleotide comprises or consist of any nucleic acid sequence encoding SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28 or 29.

Also provided herein are vectors comprising any isolated nucleic acid molecules encoding mutated ACE2 amino acid sequences. In some embodiments, the nucleic acid molecule encoding the mutated ACE2/ACE2-vECD, is operably linked to a promoter to drive the ACE2 or ACE2 protein expression. In some examples, the ACE2 polynucleotide is at least 80%, at least 85%, at least 90%, at least 95%, at least 96%, at least 97%, at least 98% or at least 99% identical to nucleotides encoding SEQ ID NO 1, 2, 3, 4, 5, 6, 7, 8, 9, 10, 11, 12, 13, 14, 15, 16, 17, 18, 19, 20, 21, 22, 23, 24, 25, 26, 27, 28 or 29.

Vectors and Manufacturing:

Wild type ACE2, ACE2-vECD or ACE2-vECD-Fc are expressed and manufactured using mammalian cell culture systems such as Chinese hamster ovarian (CHO), baby hamster kidney (BHK) cells and purified to homogeneity, administered to human body as a prevention and/or for urgent treatment of coronavirus infectious diseases such as SARS, MERS and COVID-19 or variants. The basic cloning and molecular biology method are known in the art and can be found in the reference (Green, M. R. et al, 2012, Molecular Cloning: A Laboratory Manual, *Fourth Edition*, Cold Spring Harbor Laboratory Press Bookstore A Division of CSHL).

Figure 11:
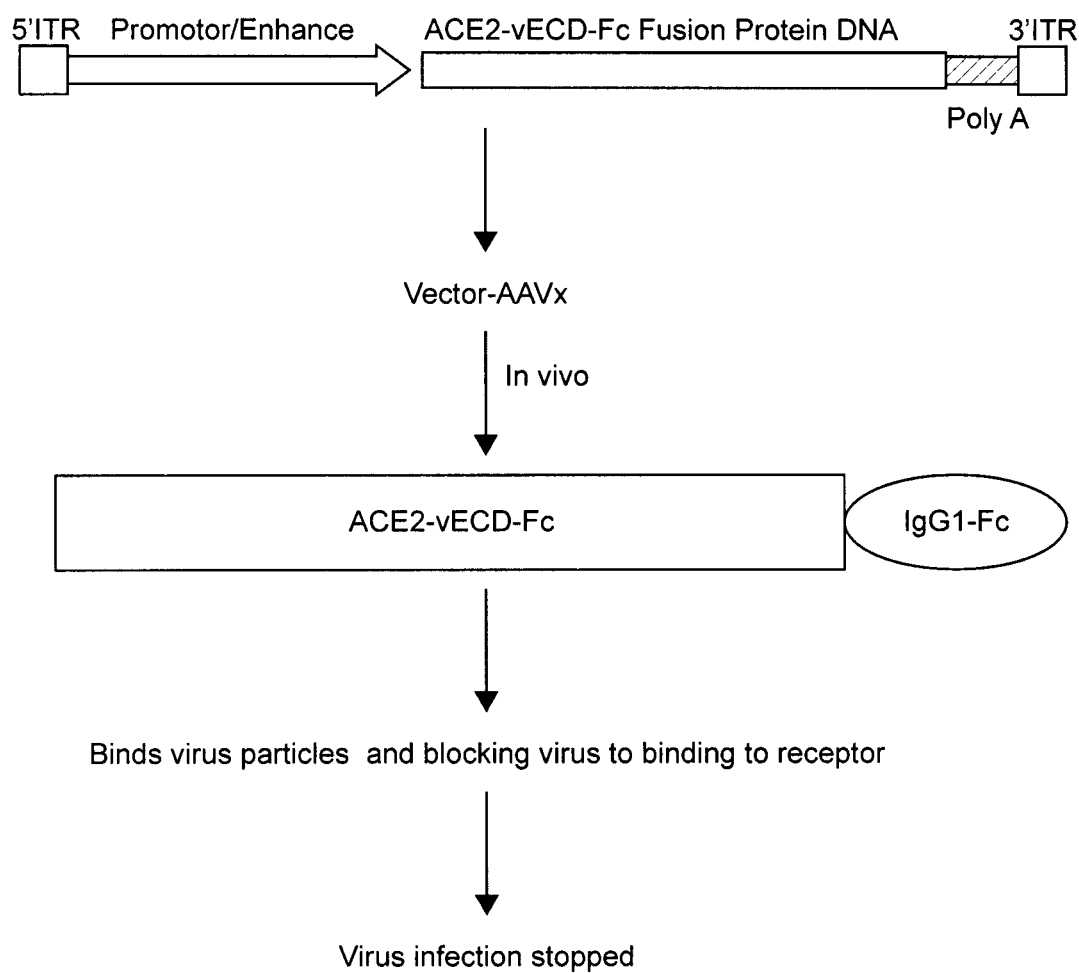
FIG. 11 shows the structure of a viral vectorized ACE2-vECD-Fc (AAV-ACE2-vECD-Fc)

Wild type ACE2, ACE2-vECD or ACE2-vECD-Fc are further vectorized for delivery to human body for long acting expression of the gene of interest. The vector design and production process are simply described in FIG. 11.

Vectors includes but not limited to retrovirus, adenovirus, adeno-associated virus, herpes virus, pox virus, human foamy virus (HFV), and lentivirus. All viral vector genomes have been modified by deleting some areas of their genomes so that their replication becomes deranged and it makes them more safe, but the system has some problems, such as their marked immunogenicity that causes induction of inflammatory system leading to degeneration of transduced tissue; and toxin production, including mortality, the insertional mutagenesis; and their limitation in transgenic capacity size. During the past few years some viral vectors with specific receptors have been designed that could transfer the transgenes to some other specific cells, which are not their natural target cells (retargeting).

Nonviral systems comprise all the physical and chemical systems except viral systems and generally include either chemical methods, such as cationic liposomes and polymers, or physical methods, such as gene gun, electroporation, particle bombardment, ultrasound utilization, and magnetofection. Such method is more importantly less induction of immune system and no limitation in size of transgenic DNA compared with viral system have made them more effective for gene delivery than nonviral delivery systems to date.

The Wild type ACE2, ACE-vECD or ACE2-vECD-Fc coding DNA fragment will be also cloned into gene delivery system using viral vector described herein above or non-viral vectors. A polynucleotide encoding the ACE2 or its mutants/variants can be cloned in a vector for expression its polypeptide for manufacturing purpose. Such vector can also be used for gene therapy purpose. When an AAV vector is used, the vector can include inverted terminal repeats (ITRs). In some embodiments, the AAV vector comprises a nucleotide sequence at least 80%, at least 85%, at least 90%, at least 95%, at least 96%, at least 97%, at least 98% or at least 99% identical to nucleotides AAV.

In some examples, the vector comprises a nucleotide sequence at least 80%, at least 85%, at least 90%, at least 95%, at least 96%, at least 97%, at least 98% or at least 99% identical to nucleotides AAV vectors.

In some embodiments, the vector is an AAV vector. The AAV serotype can be any suitable serotype for delivery of transgenes to a subject. In some examples, the AAV vector is a serotype 8 AAV (AAV8). In other examples the AAV vector is a serotype 1, 2, 3, 4, 5, 6, 7, 9, 10, 11 or 12 vector (i.e., AAV1, AAV2, AAV3, AAV4, AAV5, AAV6, AAV7, AAV9, AAV10, AAV11 or AAV12). In yet other examples, the AAV vector is a hybrid of two or more AAV serotypes (such as, but not limited to AAV2/1, AAV2/7, AAV2/8 or AAV2/9). The selection of AAV serotype will depend in part on the cell type(s) that are targeted for gene therapy.

Present invention provides a vector is transfected or infected into a host cell for expression. Such host cell can produce polypeptide. Alternatively, such a host cell can be used for cell therapy purpose.

The present invention provides isolated host cells comprising the nucleic acid molecules or vectors disclosed herein. For example, the isolated host cell can be a cell (or cell line) appropriate for production of recombinant AAV (rAAV). In some examples, the host cell is a mammalian cells, such as a CHO, HeLa, HEK-293, BHK, Vero, RD, HT-1080, A549, Cos-7, ARPE-19, or MRC-5 cell.

Viral vector carrying ACE2-vECD-Fc can be produced in any eukaryotic cell culture system such as mammalian cell, insect cell and yeast cells.

The method also relates to a method for producing a stock of recombinant virus by producing virus suitable for gene therapy comprising DNA encoding ACE2. This method preferably involves transfecting cells permissive for virus replication (the virus containing the nucleic acid molecule) and collecting the virus produced.

The invention also includes a transformed cell containing the vector and the recombinant ACE2 or ACE2-vECD nucleic acid molecule sequences.

Treatment and Immunization

The present invention provides using ACE2 vECD as virus-receptor blocker, a molecule exerts no ACE2 enzymatic activity. By this approach, the unwanted biological consequences will not cause unwanted effect from the administration of the ACE2 therapeutics such recombinant protein, DNA, mRNA or vector mediated treatment. In one embodiment, a wild type ACE2 is also used herein.

In one embodiment, as a virus-receptor interaction blocker, when a virus enters into body and encount the soluble form of ACE vECD protein, it competes binding of virus against host cell surface ACE2 molecules, the virus receptor, and prevent host ACE2 binding to virus and therefore. Virus replication process is terminated. Binding of soluble cell surface ACE2 is rescued and normal biological of cells are maintained.

Further provided are recombinant AAV (rAAV) comprising a nucleic acid molecule disclosed herein. In some embodiments, the rAAV is rAAV5. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes (such as, but not limited to AAV2/1, AAV2/7, AAV2/8 or AAV2/9).

Compositions comprising a rAAV disclosed herein and a pharmaceutically acceptable carrier are also provided by the present disclosure. In some embodiments, the compositions are formulated for intravenous or intramuscular administration. Suitable pharmaceutical formulations for administration of rAAV can be found, for example, in U.S. Patent Application Publication No. 2012/0219528 (herein incorporated by reference).

As provided herein ACE2-vECD or ACE2-vECD-Fc is a soluble receptor for coronaviruses. The invention of ACE2-vECD or ACE2-vECD-Fc fusion protein can specifically bind to spike protein of (SARS) coronavirus (SARS-CoV-1), Middle East Respiratory syndrome (MERS) coronavirus (MERS-CoV) and the current World pandemic CoVID-19, SARS-CoV-2 and HCoV-NL63.

The ACE2 or ACE2-vECD polypeptides are used for the treatment of cardiovascular disease, high blood pressure, myocardia infarction (MI), fibrosis, inflammation, More should be listed.

The invention can be used for treatment and administered to treat infection caused by any of these emerging coronaviruses and other further related viruses; The bound virus can be cleared by Fc receptor positive immune cells.

Further provided are methods of treating a subject diagnosed with viral infection, comprising selecting a subject with such infection and administering to the subject a therapeutically effective amount of a rAAV (or a composition comprising a rAAV) disclosed herein.

The present invention of AAV-ACE2-vECD or AAV-ACE2-vECD-Fc can transduce non immune cells according to serotype of AAV vector used, such as AAV5 can transduce hepatocytes, muscle, epithelium cells. This is very important for those whose immune response is low and immunity can be built by non-immune cells that has been transduced by vectors such as AAVx-ACE2-vECD-Fc vector.

In one embodiment, such composition of vector can sustainably express ACE2-vECD-Fc fusion protein for multiple years, thus providing a long-lasting protection against virus infection.

Methods of preventing or prophylaxis treatment in a healthy subject by using compositions with rAAV/ACE2-vECD, ACE2, ACE-vECD are also provided by the present disclosure. In some embodiments, the methods include administering to the subject a therapeutically effective amount of a rAAV (or a composition comprising a rAAV) disclosed herein. In some embodiments, the subject with a viral infection. Such infection can be SARS-Cov1, SARC-Cov-2, MERS-Cov1 or HCoV-NL63. Thus, in some examples, the method includes selecting a subject with different viral infections.

Mutation of the zinc ion binding motif completely abolishes the ACE2 enzyme activity, the protein molecules, ACE2-ECD-Fc, ACE2-vECD-Fc and the vectors (viral or non-viral) carrying these types of DNA fragment and its protein products functions only as neutralization antibodies and no enzyme function. Therefore, it is safe to use these products.

In addition, changes of some relevant amino acid residuals at the N-terminus or near for zinc binding motif significantly enhanced SARS-CoV-1, SARS-CoV-2 and MERS-CoV 51 protein binding to ACE2 receptors.

Methods and compositions for administering ACE2 (including in gene therapy) to isolated cell or an animal are explained, for example, in U.S. Pat. Nos. 5,672,344, 5,645,829, 5,741,486, 5,656,465, 5,547,932, 5,529,774, 5,436,146, 5,399,346, 5,670,488, 5,240,84, 6,322,536, 6,306,830 and 6,071,890 and US Patent Application No. 20010029040 which are incorporated by reference in their entirety.

The methods and compositions can be used in vivo or in vitro. The invention also includes compositions (preferably pharmaceutical compositions for gene therapy). The compositions include a vector containing ACE2. The carrier may be a pharmaceutical carrier or a host cell transformant including the vector. Vectors known in the art include but are not restricted to retroviruses, adenoviruses, adeno associated virus (AAV), herpes virus vectors, such as vaccinia virus vectors, HIV and lentivirus-based vectors, or plasmids. The invention also includes packaging and helper cell lines that are required to produce the vector. Methods of producing the vector and methods of gene therapy using the vector are also included with the invention.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

An immunogenic or immunological composition may also be formulated in the form of an oil-in-water emulsion. The oil-in-water emulsion may be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers may be non-ionic surfactants, such as esters of sorbitan, mannide (e.g., anhydromannitol oleate), glycerol, polyglycerol, propylene glycol, sucrose, trehalose, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant may be a mixture of emulsifier(s), micelle-forming agent, and oil such as that which is commercially available under the name Provax® (IDEC Pharmaceuticals, San Diego, Calif.).

The immunogenic compositions of the invention may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO4)2, AlNa (SO4)2, AlNH(SO4)2, silica, alum, Al(OH)3, Ca3(PO4)2, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34.sup.th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that may be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-alpha., IFN-beta., and IFN-gamma. (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or alpha-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which may be administered either as proteins or in the form of DNA, on the same expression vectors as those encoding the antigens of the invention or on separate expression vectors.

The immunogenic compositions may be designed to introduce the nucleic acids or expression vectors to a desired site of action and release it at an appropriate and controllable rate. Methods of preparing controlled-release formulations are known in the art. For example, controlled release preparations may be produced by the use of polymers to complex or absorb the immunogen and/or immunogenic composition. A controlled-release formulation may be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or PEI derived or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-gamma. ELISPOT assays, IL-2 ELISPOT assays, intracellular cytokine assays, and other immunological detection assays, e.g., as detailed in the text "Antibodies: A Laboratory Manual" by Ed Harlow and David Lane.

In some embodiments, the rAAV is administered at a dose of about $1\times10^6$ to about $1\times10^{15}$ vector genome(vgvg)/kg. In some examples, the rAAV is administered at a dose of about $1\times10^{11}$ to about $8\times10^{13}$ vg/kg or about $1\times10^{12}$ to about $8\times10^{13}$ vg/kg. In other examples, the rAAV is administered at a dose of about $1\times10^{13}$ to about $6\times10^{13}$ vg/kg. In specific non-limiting examples, the rAAV is administered at a dose of at least about $1\times10^{10}$, at least about $5\times10^{10}$, at least about $1\times10^{11}$, at least about $5\times10^{11}$, at least about $1\times10^{12}$, at least about $5\times10^{12}$, at least about $1\times10^{13}$, at least about $5\times10^{13}$, or at least about $1\times10^{14}$ vg/kg. In other non-limiting examples, the rAAV is administered at a dose of no more than about $1\times10^{10}$, no more than about $5\times10^{10}$, no more than about $1\times10^{11}$, no more than about $5\times10^{11}$, no more than about $1\times10^{12}$, no more than about $5\times10^{12}$, no more than about 1×1013, no more than about 5×1013, or no more than about 1×1014 vg/kg. In one non-limiting example, the rAAV is administered at a dose of about 1×1012 vg/kg. In another non-limiting example, the rAAV is administered at a dose of about 1×1011 vg/kg. The rAAV can be administered in a single dose, or in multiple doses (such as 2, 3, 4, 5, 6, 7, 8, 9 or 10 doses) as needed for the desired therapeutic results. The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, inhale, spray, drinking, or intake, intradermal injection, intravenous intraperitoneal (IP) and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes may be oral, intranasal or by any other suitable route. Delivery also be accomplished via a mucosal surface such as the anal, vaginal or oral mucosa. In some embodiments of the methods disclosed herein, the AAV is administered via oral, nasal, otic, subcutaneous, intramuscular, intravenous, or intrathecal.

Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks. In a most advantageous embodiment, the interval is about 16 weeks or about 53 weeks.

The immunization regimes typically have from 1 to 6 administrations of the immunogenic composition but may have as few as one or two or four. The methods of inducing an immune response may also include administration of an adjuvant with the immunogens. In some instances, annual, biannual or other long interval (5-10 years) booster immunization may supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens. In the event that the viral vectors express US2-11 they may be used repeatedly while expressing different antigens derived from different pathogens.

Screening Assays:

The present invention provides a method to screen an agonist or antagonist against the wild type ACE2, ACE2 vECD or its fusion protein. The agonist or anta compound comprises a) contacting a population of transfected cells with mutated genes with a plurality of test agents in a high throughput screen for a time and under conditions that permit the test agent to affect ACE2 enzyme activity; and b) selecting a test agent if it caused a statistically significant increase or reduction in the level of ACE2 enzyme activity and binding affinity compared to pre-contact levels.

The invention also includes screening assays for detecting ACE2 activators, which may be used to treat disease including but limited to viral diseases. These assays are in vitro or in vivo. In a preferred embodiment, the invention includes an endothelial, kidney, lung or heart cell assay for evaluating whether a candidate compound is capable of increasing ACE2 expression or activity. Cells are cultured in the presence of at least one compound whose ability to activate expression or activity is sought to be determined and the cells are measured for an increase in the level of ACE2 expression or activity. Another aspect of the invention involves an ACE2 knock-out mouse for identifying compounds that may overcome the effects of loss of ACE2. In another embodiment, the expression of the ACE2 gene may be increased by administering an agent that increases ACE2 gene expression including any agents identified using the screening assays in this application.

Polypeptides and small organic molecules are tested in these assays. The invention includes all compounds that are identified with the screening methods of the invention and which are suitable for administration to animals in pharmaceutical compositions.

WORKING EXAMPLES

1. Example Designing, Molecular Cloning of Wildtype ACE2 ECD and ACE2-vECD, and their Mutants Gene Mutagenesis and Cloning A series of ACE2 mutants were created by fusing a human antibody heavy chain secretion signal peptide at the 5'-end and IgG1 Fc fragment at the 3'-end of the protein. The wild type ACE2-Fc protein sequence was reverse translated into DNA sequence using the SnapGene program (GSL Biotech, San Diego, Calif.) with *Homo sapiens* codon output. The ACE2-Fc DNA sequence was further modified manually to adjust the GC content and sent to Twist Bioscience (South San Francisco, Calif.) for synthesis as three overlapping DNA fragments.

For construction vectors, all primers were designed by one of the skilled in the art and the names are listed in the Table 5.

The constructs were made and as described in Table 3. To construct AMI074-pFB-CMV-SV40intron-Vh-ACE2-

G449D-Fc, plasmid AMI063-pFB-CMV-hGH_intron-hCOMP-Ang1 was cut with EcoRI to isolate the backbone fragment. The CMV promoter-SV40 intron fragment (748 bps) was PCR amplified with primers A120 and A121 and AMI060 as template. The 5'-ACE2 fragment (1517 bps) was PCR amplified with primers A056 and A145, the middle ACE2 fragment (840 bps) with primers A146 and A147, and the 3'-ACE2 fragment (660 bps) with primers A148 and A122 using the synthesized DNA fragments as templates. A second round of PCR was performed to join the CMV-SV40 intron fragment with the 5'-ACE2 fragment together with primers A120 and A145, the middle and the 3'-ACE2 fragments were joined with another PCR reaction using primers A146 and A122. These two joined PCR fragments were purified and cloned into the EcoRI sites of plasmid AMI063 using the NEBuilder HiFi DNA Assembly Kit (New England Biolabs, Ipswich, Mass.). AMI080-pSV40prom-DHFR-NeoR-CMV-ACE2-Fc was created by PCR amplifying the CMV-SV40-intron-ACE2-pA fragment from plasmid AMI074 with primers A098 and A161 and ligated into the SalI and MluI sites of AMI069. To create AMI081-pFB-CMV-SV40intron-Vh-ACE2_E402Q-G449D-Fc, plasmid AMI074 was cut with SfoI to isolate the backbone fragment. A 540 bp-ACE2 fragment with desired mutations was PCR amplified with primers A162 and A163, and AMI074 as template. The PCR fragment was purified and cloned into the SfoI sites with the NEBuilder HiFi DNA Assembly Kit. Plasmid AMI081-pFB-CMV-SV40intron-Vh-ACE2_E402Q-G466D-Fc was cut with BamHI and FseI to remove the mutated portion of ACE2 and replace with wt-ACE2 fragment from AMI080-pSV40prom-DHFR-NeoR-CMV-ACE2-Fc to create AMI089-pFB-CMV-SV40intron-Vh-ACE2-Fc. To clone AMI090-pFB-CMV-SV40in-Vh-ACE2_E385Q-Fc, plasmid AMI081 was cut with AleI and FseI to isolate the backbone fragment. A 5'-ACE2 fragment was amplified with primers A156 and A170, and a 3'-ACE2 fragment was amplified with primers A169 and A158, and plasmid AMI081 as template. A second round PCR was used to join both PCR fragments together which was then cloned into the AleI and FseI sites using the NEBuilder HiFi DNA Assembly Kit. To clone AMI082-pFB-CMV-SV40intron-Vh-ACE2_H357A-E385Q-Fc, plasmid AMI090 was cut AleI and FseI to isolate the backbone fragment. An ACE2 fragment was amplified with primers A156, A157, and A158 and plasmid AMI090 as template. The ACE2 PCR fragment was cloned into the AleI and FseI of AMI090 to created clone AMI082-pFB-CMV-SV40intron-Vh-ACE2_H357A-E385Q-Fc. The ACE2 fragment between AleI and FseI was PCR amplified with primers A156, A159, and A158 and plasmid AMI090 as template to incorporate the desired E358-385Q mutations and cloned into AMI090 to create AMI083-pFB-CMV-SV40intron-Vh-ACE2_E358-385Q-Fc. The ACE2 fragment between AleI and FseI was PCR amplified with primers A156, A160, and A158 and plasmid AMI090 as template to incorporate the desired E358-385Q+H357A mutations and cloned into AMI090 to create AMI084-pFB-CMV-SV40intron-Vh-ACE2_E358-385Q+H357A-Fc. The ACE2 fragment between AleI and FseI was PCR amplified with primers A156, A160, and A158 and plasmid AMI089 as template to incorporate the desired H357A+385Q mutations and cloned into AMI089 to create AMI085-pFB-CMV-SV40intron-Vh-ACE2_H357A+385Q-Fc.

A second panel of ACE2 mutant plasmids in Table 3 from AMI121 to AMI129 were constructed using the AMI082 plasmid as backbone. Briefly, all the mutant sequences were synthesized by Twist Biosciences as two overlapping DNA fragments. The 5'-fragment was PCR amplified with primers A056 and A385 and the 3'-fragment was amplified with primers A386 and A158. The two PCR fragments of each mutant were purified and joined together with primers A056 and A158. The joined PCR fragments were purified again and cloned into the AflII and FseI sites of AMI082 with the NEBuilder HiFi DNA Assembly Kit to create each mutant plasmid. The mutated sequences were verified with DNA sequencing analysis using primers A024, A145, A169, and A148.

The plasmid constructs with desired ACE2-vECD-Fc variant mutations used in this project are listed in Table 1 and Table 3 and all primers used for PCR and DNA sequencing are listed in Table 5. The full ACE2 coding DNA sequences of all constructs are listed below.

Following the procedure described above, the DNA constructs encoding the rest of the mutant proteins of ACE2-vECD or ACE2-vECD-Fc fusion proteins were cloned, characterized by DNA sequencing and the DNA sequences listed are those encoding the ACE2-vECD-Fc fusion proteins only.

TABLE 5

The sequence ID of oligo nucleotides of the primers used in molecular cloning

| Primer ID | DNA sequence |
|---|---|
| A024 | 5'-ATCCAGCCTCCGGACTCTAGAGTTAACTGGTAAGTTTAGT-3' (SEQ ID NO: 33) |
| A056 | 5'-GTTGCCTTTACTTCTAGGCCTGCCGCCACCatgGAGTTCGGCCTGAGCTGGCTGTTCCT-3' (SEQ ID NO: 34) |
| A074 | 5'-AACAGCTATGACCATG-3' (SEQ ID NO: 35) |
| A098 | 5'-ATGTACGGGCCAGATATACGCGTTCGTTACATAACTTACGGTAAA-3' (SEQ ID NO: 36) |
| A120 | 5'-TGATTATTGACTAGTATCTGCGTTACATAACTTACGGTAA-3' (SEQ ID NO: 37) |
| A121 | 5'-ACTCcatGGTGGCGGCAGGCCTAGAAGTAAAGGCAACATC-3' (SEQ ID NO: 38) |
| A122 | 5'-ATAAAGATATTTTATTTTCGAATTCTCAGC-3' (SEQ ID NO: 39) |
| A123 | 5'-CTGTTCTACCAGAGCAGCCTGGCCA-3' (SEQ ID NO: 40) |
| A124 | 5'-CTGGGAGAACAGCATGCTGACCGAC-3' (SEQ ID NO: 41) |
| A125 | 5'-AGAGCATCAAGGTGAGAATCAGCCT-3' (SEQ ID NO: 42) |
| A126 | 5'-CGGCCAGCCCGAGAACAACTACAAG-3' (SEQ ID NO: 43) |
| A145 | 5'-TCGTGGGGCACGGGCTCCACCACGC-3' (SEQ ID NO: 44) |
| A146 | 5'-GCGTGGTGGAGCCCGTGCCCCACGA-3' (SEQ ID NO: 45) |
| A147 | 5'-TGGGGGGGAACAGGAACACGCTGGG-3' (SEQ ID NO: 46) |

TABLE 5-continued

The sequence ID of oligo nucleotides of the primers used in molecular cloning

| Primer ID | DNA sequence |
|---|---|
| A148 | 5'-GCGGCCCCAGCGTGTTCCTGTTCCC-3' (SEQ ID NO: 47) |
| A156 | 5'-GAATCCTGATGTGCACCAAGGTGACCATGGACGACTTCC-3' (SEQ ID NO: 48) |
| A157 | 5'-GGTGACCATGGACGACTTCCTGACCGCCCACGCCAGATGGGCCACATC-3' (SEQ ID NO: 49) |
| A158 | 5'-GCATGTTGAACAGCTTCT-3' (SEQ ID NO: 50) |
| A159 | 5'-GACCATGGACGACTTCCTGACCGCCCACCACCAGATGGGCCACATCCAG-3' (SEQ ID NO: 51) |
| A160 | 5'-GACCATGGACGACTTCCTGACCGCCCACGCCCAGATGGGCCACATCCAG-3' (SEQ ID NO: 52) |
| A161 | 5'-CGCCAAGCTCTAGCTAGAGGTCGACGCGGCCGCTCGGTCCGCAC-3' (SEQ ID NO: 53) |
| A162 | 5'-TTCCTGCTGAGAAACGGCGCCAACGAGGGCTTCCACcAGGCCGTGGGCG-3' (SEQ ID NO: 54) |
| A163 | 5'-GGGGTCTCACGTTCATGTTC-3' (SEQ ID NO: 55) |
| A169 | 5'-GAGATGGATGGTGTTCAAGGGCGAGATCCCCAAGGACCAG-3' (SEQ ID NO: 56) |
| A170 | 5'-CTGGTCCTTGGGGATCTCGCCCTTGAACACCATCCATC-3' (SEQ ID NO: 57) |
| A385 | 5'-CCGAAGGGCACGGTCAGGCTGTACA-3' (SEQ ID NO: 58) |
| A386 | 5'-TGTACAGCCTGACCGTGCCCTTCGG-3' (SEQ ID NO: 59) |

The plasmid constructs with desired ACE2 mutations used in this project are listed in Table 3 and the full ACE2 coding DNA sequences of all constructs are listed above. All primers used for PCR and DNA sequencing are listed in Table 5.

All constructs were first cloned into our mammalian proprietary expression vector and final vectors are listed in above Table 4.

2. Example: Transient Expression of the Constructs in Mammalian Cell Culture System Human HEK293 cells were cultured in DMEM medium (Thermo fisher) with 10% FBS (ATCC Manassas, Va.) in a CO2 incubator at 37° C. For maintenance passage, cells were split 1:10 twice a week. For transfection, cells were seeded on 10-cm cell culture dish (Corning, N.Y.) at 2×10⁶ cells/dish in 10 mL media overnight. Fourteen µg plasmid DNA and 22 µL of Lipofectamine 3000 were each diluted in 0.5 mL of Opti-medium and mixed together. After incubation at room temperature for 5 min, the mixture was added to the cells dropwise and incubated at 37° C. in the CO2 incubator for 48 hours. Medium was harvested for further experiments.

HEK293 cells were seeded onto 10 cm tissue culture dishes at a density 2×10⁶ 1 day prior to transient transfection. Each transfection of ACE2-ECD-Fc (wt) or ACE2-vECD-Fc variant plasmid was performed using 14 µg/dish DNA with Lipofectamine 3000 reagent (Invitrogen, Carlsbad, Calif.) following the manufacturer's protocol. Cell culture supernatants were collected and analyzed for protein expression by western blot, at 48 hour post-transfection. All transfections were performed in triplicate in at least three independent experiments.

Figure 12:
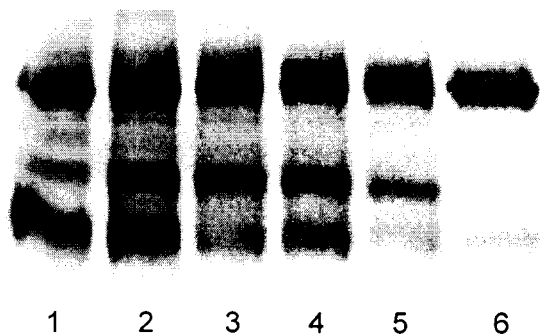
FIG. 12 shows western blot results of ACE2-Fc variants/mutants.

ACE2-ECD-Fc (wt) or ACE2-vECD-Fc variant proteins were determined by the SDS-PAGE and Western blot analysis. HEK293 cell media (supernatants) collected 48 hours from plasmid transfection or 72 hours from AAV5-ACE2 transduction were used for Western blot analysis. A total volume of 30 µL of cell supernatants was mixed with 10 ul of 4×loading buffer and loaded onto the NuPAGE 10% Tris-Glycine gels (Invitrogen) for electrophoresis. Proteins were subsequently transferred onto PVDF membranes using X Cell II™ Blot Module (Invitrogen, Carlsbad, Calif., USA). Membranes were treated with casein blocker in PBS (Thermo Scientific, Waltham, Mass., USA) for at least one hour at room temperature and probed with the goat anti-human IgG1 Fc antibody biotin conjugate (Abcam, Cambridge, UK) followed by incubation with streptavidin conjugated with horseradish peroxidase (Abcam). Proteins were detected using the ECL™ Western blotting kit (Amersham) and photos recorded with iBright™ CL1500 Imaging System (Invitrogen, Carlsbad, Calif.). (FIG. 12).

3. Example: Purification of ACE2-ECD-Fc (WT) and ACE2-vECD-Fc Variants

ACE2-ECD-Fc (wt) or ACE2-vECD-Fc variant proteins expressed were purified from HEK293 cell culture harvests by protein A affinity column chromatography (Mabselect™)

Figure 13:
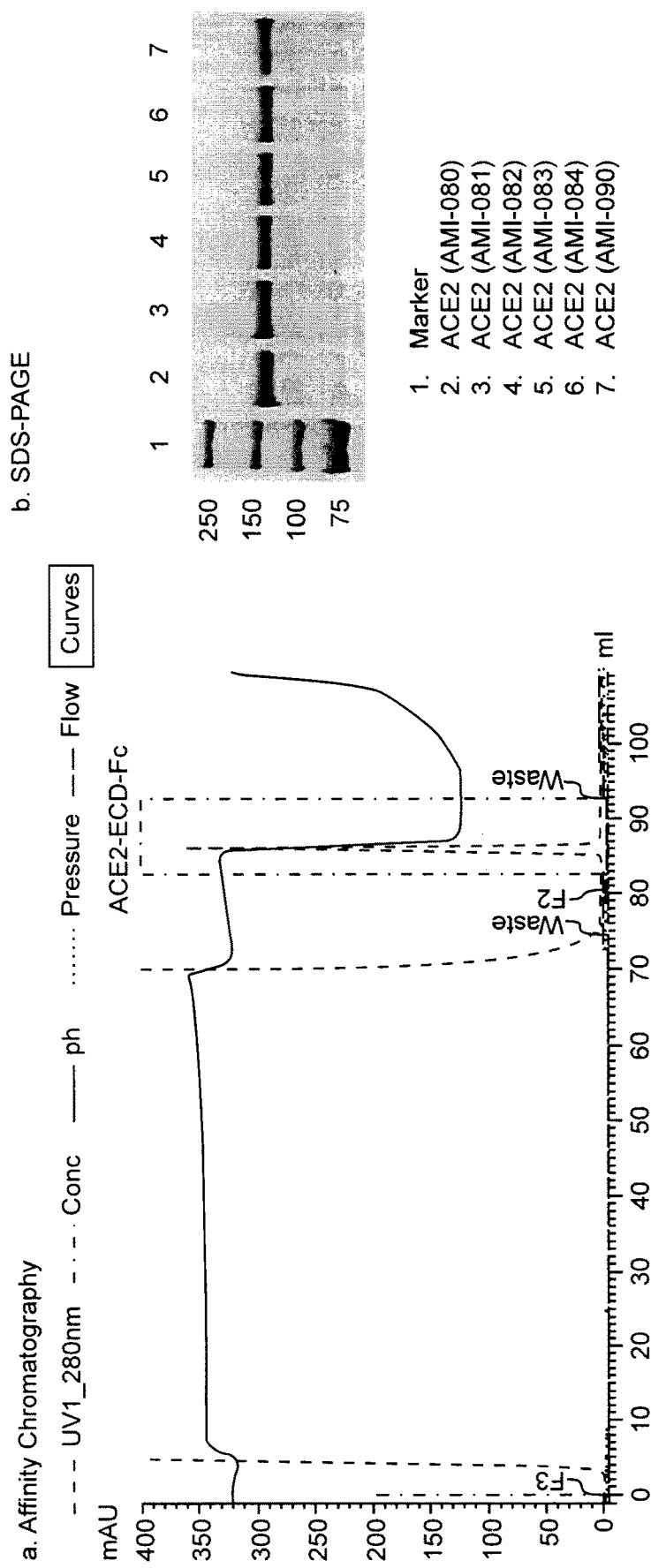
FIG. 13 shows affinity chromatography and SDS-PAGE assays of ACE2-Fc Variant Preparations in accordance with some embodiments of the present disclosure.

The culture supernatants were filtered through 0.2 µm syringe filter (Millipore) For purification of secreted ACE2 from each filtered culture, HiTrap™ 1 mL MabSelect™ Protein A column (GE Health Care Lifesciences, Marlborough, Mass. 01752) was used respectively. The column chromatogram showed a sharp peak of eluted off the column when pH reached 3-4.0 ((a) in FIG. 13). Chromatography Protein concentration of each preparation was determined by the BCA protein assay and results are listed in Table 6 (Thermo scientific, Hayward, Calif.). Protein size of each construct is as expected ((b) FIG. 13).

TABLE 6

Summary of Purified ACE2-ECD-Fc and ACE2-vECD-Fc proteins from HEK 293 Cell Culture Supernatant

| Protein code | HEK293 Cell Culture Harvest (mL) | MabsSelect Protein A Eluate (mL) | Final Product Volume (mL) | Protein concentration (mg/mL) |
|---|---|---|---|---|
| 293_AMI080 | 80 | 1.0 | 1.0 | 0.34 |
| 293_AMI081 | 56 | 1.0 | 1.0 | 0.25 |
| 293_AMI082 | 77 | 1.0 | 1.0 | 0.25 |
| 293_AMI083 | 98 | 1.0 | 1.0 | 0.30 |
| 293_AMI084 | 98 | 1.0 | 1.0 | 0.25 |
| 293_AMI090 | 84 | 1.0 | 1.0 | 0.27 |

4. Example: Enzymatic Activity Determination of ACE-vECD-Fc Fusion Proteins

The enzymatic activity of the affinity column chromatographic purified ACE2 ECD-Fc fusion protein variants were measured according to Fenxia Xiao and Kevin B. Burns (Ref: Measurement of angeiotension converting enzyme 2 activity in biological fluid (ACE2), chapter 8, Hypertension: Methods and Protocols, Methods in Molecular Biology, vol.

1527, Rhian M. Touyz and Ernesto L. Schiffrin (eds.), DOI 10.1007/978-1-4939-6625-7_8, © Springer Science+ Business Media LLC 2017). The mechanism of the measurement is based on the hydrolysis of an intramolecularly quenched fluorogenic ACE2 substrate, in the presence or absence of ACE2 specific inhibitor MLN-4760 (Merck Millipore Calbiochem™ ACE2 inhibitor, MLN-4760), which is a highly potent ACE2 inhibition with IC50=440 pM. The specificity of ACE2 ECD-Fc fusion protein is determined by the inhibition of fluorogenic signal measured at filter pair excitation 330 nm and emission 450 nm with ACE2 inhibitor MLN-4760, when the wild type ACE2 ECD-Fc fusion protein is used. In the meantime, the ACE2 ECD-Fc mutant protein enzyme activity was tested in presence and absence of ACE2 inhibitor MLN-4760 when both wildtype and mutant protein were tested simultaneously.

The ACE2 enzyme assay was performed in an enzyme assay buffer, 50 mM 2-(N-morpholine) ethanesulfonic acid (MES), 300 mM NaCl, 10 µM ZnCl2, pH 6.81. The ACE2 fluorogenic substrate synthetic peptide molecule, Mca-Ala-Pro-Lys(Dnp)-OH (AnaSpec, cat. #60757, San Jose, Calif., USA). The substrate was dissolved in 1% NH4OH to 15 mM. The substrate solution was aliquoted at 10 µL per vial and stored at −80° C. Protease inhibitor N-ethylmaleimide (NEM, (MilliporeSigma Cat. 34115-5GM, St Louis, Mo., USA) was 100 mM in Milli Q water and phenylmethylsulfonyl fluoride (PMSF) was 100 mM in 100% ethanol. ACE2 inhibitor MLN-4760 (Merck MilliporeCalbiochem, San Diego, Calif., USA, Catalog Number: 530616) was 10 µM in Milli Q water. The assay buffer/substrate mix is made freshly according to the following Table 7.

TABLE 7

ACE2 Enzyme Activity Assay

| Component (stock solution) | Vol (µL) | Concentration in buffer mix | Final concentration in reaction mix |
|---|---|---|---|
| ACE2 substrate (15 mM in 1% NH4OH) | 1 | 15 µM | 10.5 µM |
| NEM (100 mM in Milli-Q H2O) | 10 | 1 mM | 0.7 mM |
| PMSF (100 Ethanol) | 10 | 1 mM | 0.7 mM |
| Assay buffer | 979 | | |
| Total | 1000 | | |

In a reaction mix of 100 µL, 70 µL of assay buffer/substrate mix was added and therefore the final concentration buffer ingredients were 35 mM MES, 210 mM NaCl, 7 µM ZnCl2. The final concentration of ACE2 substrate, protease inhibitors were 10.5 µM and 0.7 mM separately.

Wild type ACE2 ECD-Fc (AMI080) and five mutant ACE2 ECD-Fc proteins (AMI081, AMI082, AMI083, AMI084 and AMI085) were purified described previously.

These assays were performed in a 96-well microtitration plate. For each protein, it was diluted in sterile phosphate buffered saline (PBS, HyPure™, GE Healthcare, Hyclone Laboratories, Logan, Utah) at range of 500, 100, 20, 10, 5, 2.5 ng/mL 3.13, and 1.56 nM separately. The sampling scheme is shown in the following Table 8. Two wells of blank control were set with the assay.

TABLE 8

Concentration of ACE2 ECD-Fc protein in each assay

| Reaction well | Diluted ACE2-Fc (ng/mL) | wtACE2-Fc (µl/well) | Milli Q H2O or inhibitor (µl/well) | ACE2 substrate/ buffer mix (µl/well) | Final ACE2-Fc, ng/mL |
|---|---|---|---|---|---|
| 1 | 3333.3 | 15 | 15 | 70 | 500 |
| 2 | 666.6 | 15 | 15 | 70 | 100 |
| 3 | 333.3 | 15 | 15 | 70 | 20 |
| 4 | 166.7 | 15 | 15 | 70 | 10 |
| 5 | 83.33 | 15 | 15 | 70 | 5 |
| 6 | 41.67 | 15 | 15 | 70 | 2.5 |

The reaction was carried out in a dark 96-well plate and each protein was tested in duplicate. After all reactants and buffer mix were added, mixed thoroughly and immediately sealed and wrapped with aluminum foil. The plate was placed on a shake platform with gentle shaking at 140 rpm at ambient temperature for 16-20 hr.

The plate was read for relative fluorescence unit (RFU) with a fluorometer, fmax (Molecular Device, Sunnyvale, Calif., USA) with the excitation wavelength of 355 nm and emission wavelength of 460 nm. The data was averaged of the duplicate readings. The following are the plots of RFU against protein concentration of each individual ACE2 ECD-Fc protein.

Figure 14:
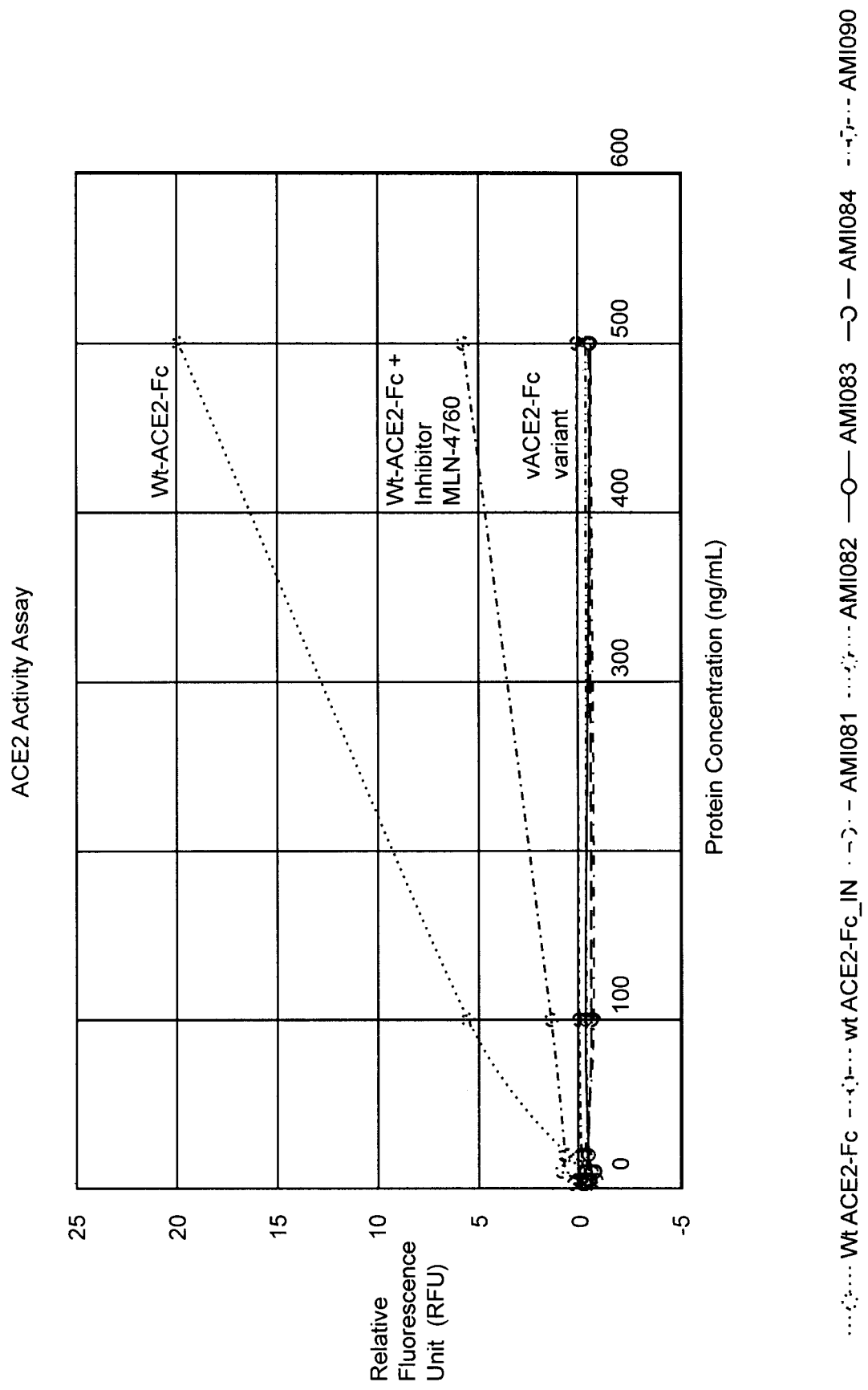
FIG. 14 shows assay results of certain polypeptides of the present disclosure.
Figure 15B:
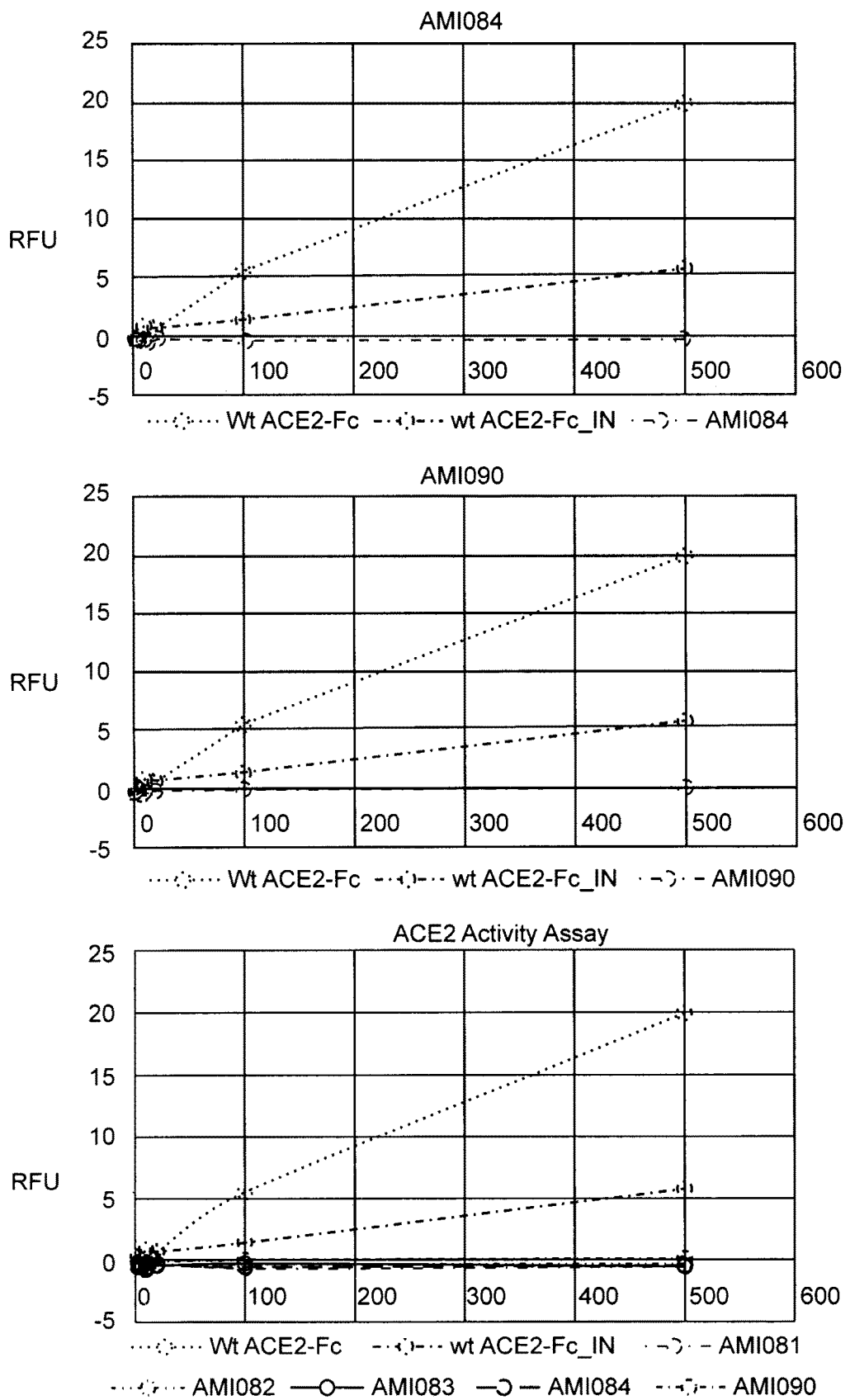

As shown in FIG. 14, Wild type wtACE2 ECD-Fc is enzymatically active, the relative fluorescence unit (RFU) increased with protein concentration added to the reactions. RFU was significantly reduced in the presence of ACE2 inhibitor MLN 4760. The ACE2 enzyme assay is specific because the reaction can be inhibited by ACE2 specific inhibitor 0.73 µM. It is highly reproducible, inter assay CV is 3.6% and intra assay CV is 1-6%. Mutation of one or more than amino acid residues in the Zinc-binding motif depleted ACE2 enzyme activity. Any mutant ACE2-Fc has no enzyme activity (Apoenzyme). While all mutant ACE2 ECD-Fc proteins did not give significant RFU, indicating the enzyme activity of ACE2-vECD-Fc variant protein was depleted by mutation either a single amino acid residue, AMI090 with only a single mutation of E402Q, it lost catalytical activity for more than 99.9%. For better view of the catalytical activity of each ACE2-vECD-Fc protein, the enzyme reaction results are shown individually in FIG. 15A, 15B and sequence mutation correlation to the enzyme activity is shown in Table 9.

TABLE 9

Summary Results of ACE2 Enzyme Activity of the Wildtype and Mutant Fc Fusion Protein

| Clone ID | Residue Mutated | Mutated Sequence | Enzyme activity (RFU) @ 500 ng/mL |
|---|---|---|---|
| AMI080 | ACE2-Fc wt | CTKVTMDDFLTAHHEMGHIQYDMAYAAQPFLERNGANEGFHEAVGEIMSL | 19.97 ± 0.11 |
| AMI081 | ACE2_E402Q-G466D-Fc | CTKVTMDDFLTAHHEMGHIQYDMAYAAQPFLERNGANEGFHQAVGEIMSL . . . D466 | −0.59 ± 0.08 |
| AMI082 | ACE2_H374A-E402Q-Fc | CTKVTMDDFLTAHAEMGHIQYDMAYAAQPFLERNGANEGFHQAVGEIMSL | −0.32 ± 0.03 |
| AMI083 | ACE2_E375_402Q-Fc | CTKVTMDDFLTAHHQMGHIQYDMAYAAQPFLERNGANEGFHQAVGEIMSL | −0.55 ± 0.09 |
| AMI084 | ACE2_H374A-E375_402Q-Fc | CTKVTMDDFLTAHAQMGHIQYDMAYAAQPFLERNGANEGFHQAVGEIMSL | −0.48 ± 0.06 |
| AMI090 | ACE2_E402Q-Fc | CTKVTMDDFLTAHHEMGHIQYDMAYAAQPFLERNGANEGFHQAVGEIMSL | 0.11 ± 0.04 (0.5%) |

The data shown demonstrated that mutation of any sinble residue in the catalytic center, the zinc binding motif, depleted the enzyme activity.

The activity depleted ACE2-vECD showed no enzyme activity after fusion to Fc.

5. Example: Binding of ACE2-ECD-Fc Protein to Spike Proteins of Coronavirus by Enzyme Linked Receptor-Ligand Assay (ELRLA)

The binding of 3 coronavirus spike proteins to each of ACE2-ECD-Fc or ACE2-vECD-Fc was determined by enzyme linked receptor-ligand assay (ELRLA).

All buffers were made in sterile M.Q water or sterile PBS (Cat: SH30529.03, GE Healthcare Life Science, Logan, Utah). A 96 well microplate, each was coated 50 µL/well with 10 nM and 20 nM of spike protein 1 (S1) of SARS-CoV-1, SARS-CoV-2 or MERS-CoV diluted individually in sodium carbonate buffer (50 mM NaCO$_3$, NaHCO$_3$, pH 9.6). The S1 proteins are purchased from Sino Biological (SARS-CoV-1 S1 cat #40150-V08B1, SARS-CoV-2 S1 cat #40591-V08H, MERS-CoV S1 protein cat #: 40069-V08H, Beijing, China). The microplate was tightly sealed and incubated at 2-8° C. for 12 hours and was washed with phosphate buffered saline (10 phosphate buffer, 150 mM NaCl, pH 7.2, 0.01% Tween 20, PBS-T) for 3 times and blocked with blocking buffer (1% BSA in PBST) at 37° C. for 2 hr. After washing serially diluted ACE2-ECD-Fc or ACE2-vECD-Fc variant protein, 20 nM, 10 nM, 5 nM, 2.5 nM, 1.25 nM, 0.63 nM and 0.313 nM, was added in duplicate each well at 50 µL/well. The plates were sealed and incubated at 37° C. for 60 min. The plates were washed with PBS-T 3 times. To each well 50 µL of goat anti-human IgG Fc-biotin conjugate (Abcam cat. ab98618, Cambridge, Mass.) was diluted 1:10000 in PBS-T-0.5% (w/v) BSA followed by incubation at 3° C. for 60 min. The microplates were washed 3 times with PBS-T and then 1:15000 diluted streptavidin horseradish peroxidase (HRP) was added at 50 µL/well and incubated at 37° C. for 60 min. The microplates were washed 3 times with PBS-T and 1 time with PBS to remove the remaining Tween 20. The reaction was developed with 100 µL/well of 1-Step™ ABTS substrate (Thermo Scientific REF 37615, Rockford, CA) at 37° C. for 30 min and stopped with 50 µL/well of 2% (w/v) SDS. The plates were read at 405 nm using VERSAmax Microplate Reader (Molecular Device, Sunnyvale, Calif.). The results were shown in FIG. 16A. From the binding assay, the SARS-CoV-2 spike protein bound to the wildtype AMI080 (ACE2-ECD-Fc) and the variant of AMI082 (ACE2-vCECD-Fc, H274A, E402Q) and AMI090 (ACE2-vECD-Fc, E402Q) with very similar binding profile (FIG. 16A) but the affinity and Ymax values were changed.

Figures 16A, 16B:
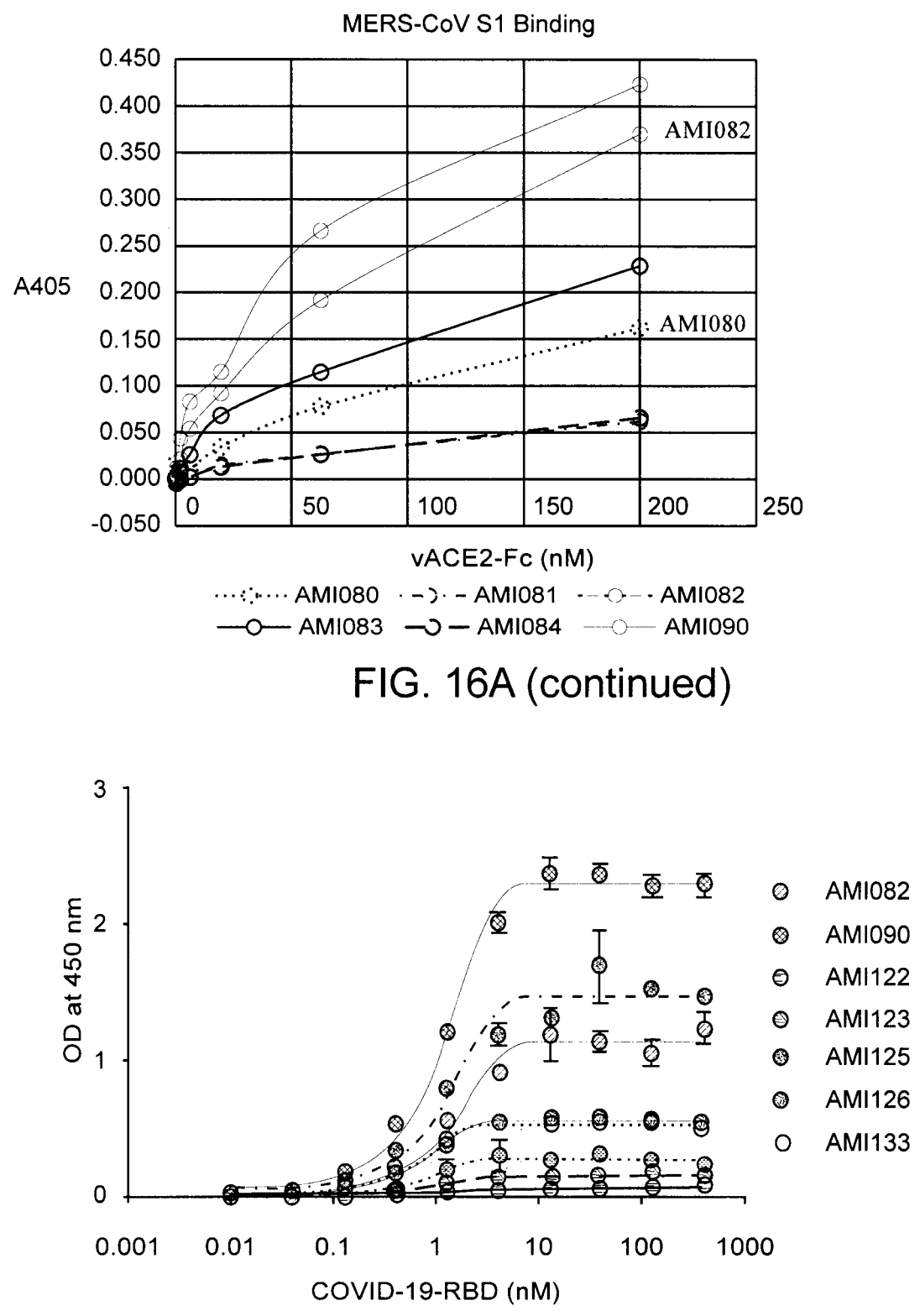

To our surprise, the MERS-CoV S1 protein hardly bound the wildtype ACE2-ECD-Fc but the mutant AMI090 and AMI082 showed >200% and >150% of increase in binding affinity than that of the wildtype (FIG. 16A).

Figure 17A:
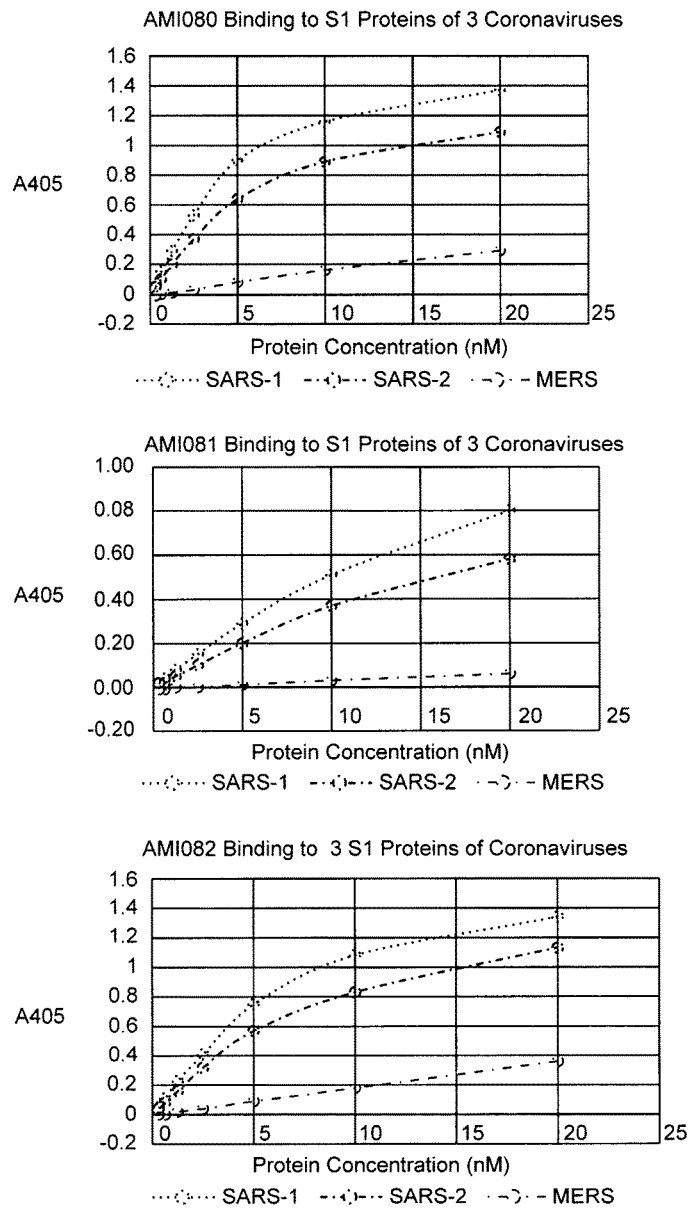

To more clearly demonstrate the individual ACE2-ECD-Fc or ACE2-vECD-Fc reacting with SARS-CoV-1, SARS-CoV-2 and MERS-CoV S proteins, 20 nM of each S1 protein was coated and assayed exactly as in procedure, each construct protein reactivity with the three ligands is plotted in FIG. 17A, 17B.

Based on the ELALA and enzyme analytical data combined together, we can conclude that results of the mutants AMI082 and AMI090 retaining bind capacity to viral spike proteins demonstrated that the amino acid H374 and E402 do not affect binding of SARS-CoV-1 and SARS-CoV-2 S1 proteins to their cognate receptors on host cells. The other residues E375 and H378 are both important to the binding (FIG. 16A).

In the case of MERS-CoV, the mutation of H374A and E402Q enhanced significantly the virus S1 protein binding to ACE2-vECD-Fc (AMI090 and AMI082), about 500 and 800% respectively when compared the values of their maximum reaction (Ymax value). AMI083 also showed about 200% increase in binding, while the other mutations showed hardly binding to ACE2. Therefore, we predicted the mutants ACE2-vECD-Fc (AMI090 and AMI082) can be also used for blocking MERS-CoV infection.

From these data we have discovered the relationship among the amino acid residuals, ACE2 catalytic activity and coronavirus binding properties. We summarize the findings in Table 10.

TABLE 10

Summary Results of ACE2 Enzyme and Coronavirus S1 Protein Binding of the Wildtype and Mutant Fc Fusion Protein

| Clone ID | Residue Mutated | Mutated Sequence | Enzyme activity (RFU) @ 500 ng/mL | S1 Binding (%) | | |
|---|---|---|---|---|---|---|
| | | | | SARS-CoV-2 | SARS-CoV-1 | MERS-CoV |
| AMI080 | ACE2-Fc wt | CTKVTMDDFLTAHHEMGHIQYDMAYAAQPFL LRNGANEGFHEAVGEIMSL | 19.97 ± 0.11 | 100 | 100 | 100 |
| AMI081 | ACE2_E402Q-G466D-Fc | CTKVTMDDFLTAHHEMGHIQYDMAYAAQPFL LRNGANEGFHQAVGEIMSL . . . D466 | -0.59 ± 0.08 | 35 | 35 | 17 |
| AMI082 | ACE2_H374A-E402Q-Fc | CTKVTMDDFLTAHAEMGHIQYDMAYAAQPFL LRNGANEGFHQAVGEIMSL | -0.32 ± 0.03 | 100 | 100 | 496 |
| AMI083 | ACE2_E375_402Q-Fc | CTKVTMDDFLTAHHQMGHIQYDMAYAAQPFL LRNGANEGFHQAVGEIMSL | -0.55 ± 0.09 | 55 | 55 | 239 |
| AMI084 | ACE2_H374A-E375_402Q-Fc | CTKVTMDDFLTAHAQMGHIQYDMAYAAQPFL LRNGANEGFHQAVGEIMSL | -0.48 ± 0.06 | 61 | 61 | 19 |
| AMI090 | ACE2_E402Q-Fc | CTKVTMDDFLTAHHEMGHIQYDMAYAAQPFL LRNGANEGFHQAVGEIMSL | 0.11 ± 0.04 (0.5%) | 103 | 103 | 764 |

The binding affinity was estimated following Hill equation (Mohameedyaseen Syedbasha et al, J. Visual. Exp. 2016, 1109: 4-10) and results are shown in Table 11 and Table 12 respectively for their binding to SARS-COV-2 S1 and SARS-COV-1 S1 proteins.

TABLE 11

Binding Affinity of vACE2-Fc to SARS-COV-2 S1 Protein

| ACE2-Fc Variant | AMI 080(wt) | AMI 081 | AMI 082 | AMI 083 | AMI 084 | AMI 090 |
|---|---|---|---|---|---|---|
| $Y_{max}$ | 1.326 | 1.168 | 1.306 | 1.237 | 1.174 | 1.286 |
| $EC_{50}$ | 0.663 | 0.584 | 0.653 | 0.6185 | 0.587 | 0.643 |
| KD (nM) | 10.50 | 3.31 | 0.22 | 1.43 | 0.83 | 0.34 |
| df* | 1 | 3x | 48x | 7x | 13x | 31x | df* KD difference of variant ACE2-Fc to that of the wildtype ACE2-Fc

The variant ACE2-Fc AMI082 and AMI090 showed approximately 30-50-fold higher affinity than the wildtype ACE2-Fc AMI080 protein in binding to SARS-COV-2 S1 protein (Table 11). The increased binding affinity could mean the tighter interaction between ACE-2 and SARS-COV-2 virus particles.

In the meantime, ACE2-Fc Variants were also evaluated for their binding to S1 protein of SARS-COV-1 using the same assay procedure. The results are shown enhancement of binding affinity of AMI082 and AMI090 over the wildtype ACE2-Fc by 13-fold (Table 12).

TABLE 12

Binding Affinity of vACE2-Fc to SARS-COV-1 S1 Protein

| ACE2-Fc Variant | AMI 080 (wt) | AMI 081 | AMI 082 | AMI 083 | AMI 084 | AMI 090 |
|---|---|---|---|---|---|---|
| $Y_{max}$ | 1.326 | 1.168 | 1.306 | 1.237 | 1.174 | 1.286 |
| $EC_{50}$ | 0.663 | 0.584 | 0.653 | 0.6185 | 0.587 | 0.643 |
| KD (nM) | 5.17 | 3.09 | 0.37 | 1.93 | 1.15 | 0.41 |
| df* | 1 | 2x | 14x | 3x | 4x | 13x | df* KD difference of variant ACE2-Fc to that of the wildtype ACE2-Fc

To further determine the binding affinity of these ACE-Fc variant proteins to SARS-COV-2 variants, purified proteins of virus receptor binding domain (RBD) of SARS-COV-2 B117 (N501Y) (Sino biologics cat #: 40592-V08H82). The plates were coated with vAC2-Fc proteins at 10 nM and the SARS-COV-2 B117 (N501Y) RBD protein was tested in duplicates at concentration of 0.01, 0.04, 0.13, 0.40, 1.27, 4.07, 13.02, 39.01, 125 and 400 nM. The binding affinity was estimated following Hill equation (Mohameedyaseen Syedbasha et al, J. Visual. Exp. 2016, 1109: 4-10) and results are shown in FIG. 16B and Table 13. Among these ACE2-Fc variant proteins, AMI090, AMI126, and AMI133 had a very similar KD, <1 nM. AMI090 had the highest Ymax value (FIG. 16B)

similar binding profile as the wt ACE2 ECD-Fc protein. The less mutated protein preparations are assumed to be able to bind to the S1 proteins of these coronaviruses as well.

Figure 18:
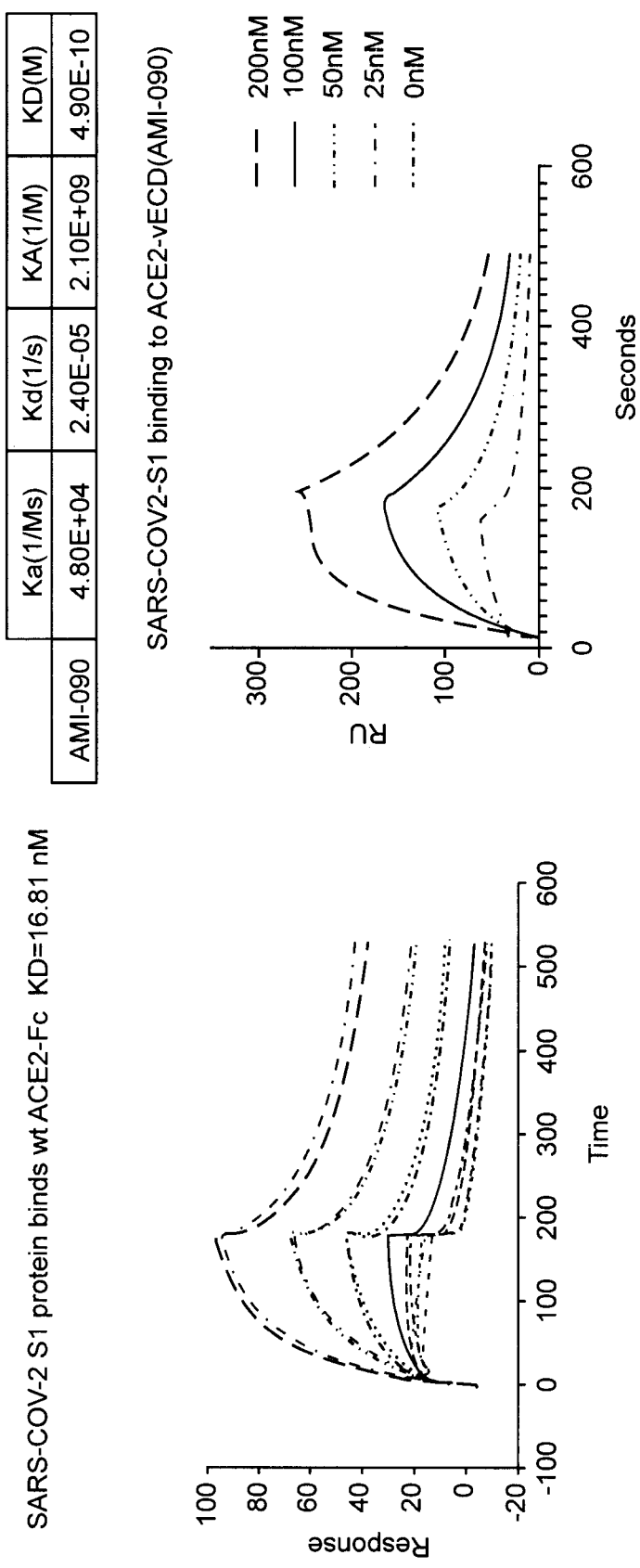
FIG. 18 shows affinity analysis results on certain polypeptides of the present disclosure using BiaCore 3000.

Results: the purified ACE2-Fc protein preparation bound to spike protein S1 of SARS-CoV-2 determined by BiaCore 3000 (FIG. 18). The purified variant ACE2-vECD-Fc proteins are under testing. The binding affinity (KD) of Wildtype ACE2-Fc, AMI080 was 16.81 nM while the variant ACE2-Fc protein AMI090 was 0.49 nM, indicating an increase in binding via Biacore assay.

7. Example: In Vitro Neutralization of SARS-Cov-2 Pseudovirus Particles

The in vitro viral neutralization screening assay was performed using SARS-CoV-2 pseudovirus, SARS-CoV-2

TABLE 13

Binding Affinity of vACE2-Fc to SARS-COV-2 B117 (N501Y) S1 Receptor Binding Domain (RBD)

| ACE2-Fc Variant | AMI082 | AMI090 | AMI122 | AMI123 | AMI124 | AMI125 | AMI126 | AMI133 | AMI135 |
|---|---|---|---|---|---|---|---|---|---|
| $Y_{max}$ | 1.146 | 2.294 | 0.071 | 0.161 | 0.145 | 1.476 | 0.564 | 0.536 | 0.285 |
| $EC_{50}$ | 1.3 | 1.1 | 1.2 | 0.9 | 8.2 | 1.3 | 0.7 | 0.5 | 1.2 |
| KD (nM) | 1.20 | 0.6 | 1.9 | 2.5 | 9.4 | 2.1 | 0.6 | 0.5 | 1.2 |

In a qualitative binding assays, the ACE2-Fc variants AMI080, AMI082 and AMI090 was evaluated for binding to various SARS-COV-2 mutants. It clearly shown in the test that the E484K variant reacted to the ACE2-Fc proteins strongly than other variants (Table 14).

S1 lentiviral vector expressing the green fluorescent protein (GFP) when it binds human ACE2 (hACE2) protein, the SARS-CoV-2 receptor on the cell surface of the stably transfected HEK293 cells (293T-hACE2). This is a safe and

TABLE 14

Qualitative analysis of binding of ACE2-Fc proteins to Various SARS-COV Spike Protein

| Variant Name | Mutation | Initial detected | Binding AMI080 | AMI082 | AMI090 |
|---|---|---|---|---|---|
| COVID-COV-2 S1 protein | Wildtype | Wuhan, China/2019 | + | + | + |
| SARS-COV-2 S1 protein | D614G | + | + | + | + |
| SARS-COV-2 (N501Y) S1 RBD | N501Y | UK | + | + | + |
| SARS-COV-2 S1 RBD (K417N) | K417N | + | + | + | + |
| SARS-COV-2 S1 RBD (E484K) | E484K | Africa | ++ | ++ | ++ |
| SARS-COV-1 S1 protein | Wildtype | China/2003 | + | + | + |
| MERS-CoV S1 protein | Wildtype | Saudi Arabia/2012 | + | + | + |

6. Example: Binding to Virus Antigen with Spike Proteins of Coronavirus by Surface Plasmon Resonance (SPR)

To determine the binding capacity of wt ACE2-ECD-Fc and mutant protein to the Spike 1 proteins of coronaviruses, surface plasmon resonance (SPR) method was employed. The wt ACE2-ECD-Fc or mutant ACE2-vECD-Fc (AMI084) was bound to Sensor chip protein A (GE Healthcare now Cytiva, cat 29-1275-57, Uppsala, Sweden) at 5 µg/mL in phosphate buffered saline with 0.01% Tween 20 (PBS-T). The S1 protein of SARS-CoV-2, the ACE2-ECD-Fc protein was able to bind to protein ligand on the chip via the $IgG_1$ Fc region. SARS-CoV-1 and MERS-CoV were obtained from Sino biligicals (Beijing, China). The S1 proteins were diluted in PBS-T at final concentration of 200, 100, 50, 25, 12.5, 6.25, 3.13 and 1.56 nM. The program was operated as binding kinetics using BiaCore 3000 instrument. The observed apparent binding affinity indicated that the recombinant wt ACE2-ECD-Fc and mutant ACE2-vECD-Fc were able to bind to S1 protein of SARS-Cov-2, SARS-CoV-1 and MERS-CoV separately. AMI084 with 3 mutations of amino acid in catalytic center of ACE2 will show specific screening method for evaluation of compound, antibody or soluble receptor of the virus.

Briefly a gelatin-coated 96-well plate was seeded with $1.5 \times 10^4$ 293 T-hACE2 cells (CMV-hACE2) per well and cultivated at 37° C., 5% $CO_2$ and 95% humidity for overnight. ACE2-ECD-Fc or ACE2-vECD-Fc variant protein was diluted individually in PBS at 1:2 serial at 20, 10, 5, 2.5, 1.25, 0.625, and 0.313 µg/mL in a a separate 96-well "setup" plate and each sample was tested I duplicates. The pseudovirus stock was diluted into approximately 1 million infectious forming unit (IFU) per mL ($10^6$ IFU/mL). The diluted pseudovirus solution of 60 µL was added to all wells containing ACE2 variant proteins and the pseudovirus plus cell control wells. The plate was mixed thoroughly and incubated at 37° C. for 1 hr. Carefully a 100 µL mixture from each well of the setup plate containing the antibody and virus dilutions was added the wells to replace the medium in corresponding wells of the HEK293T-hACE2 cells plate. Finally Trans plus™ (Alstem, Cat #V050, Richmond, CA) was added to a final concentration of 1× in each well per vendor's manual. The plate was incubated at 37° C. for 48-60 hours before reading for fluorescence. The fluorescence foci were counted in each well.

Figure 20:
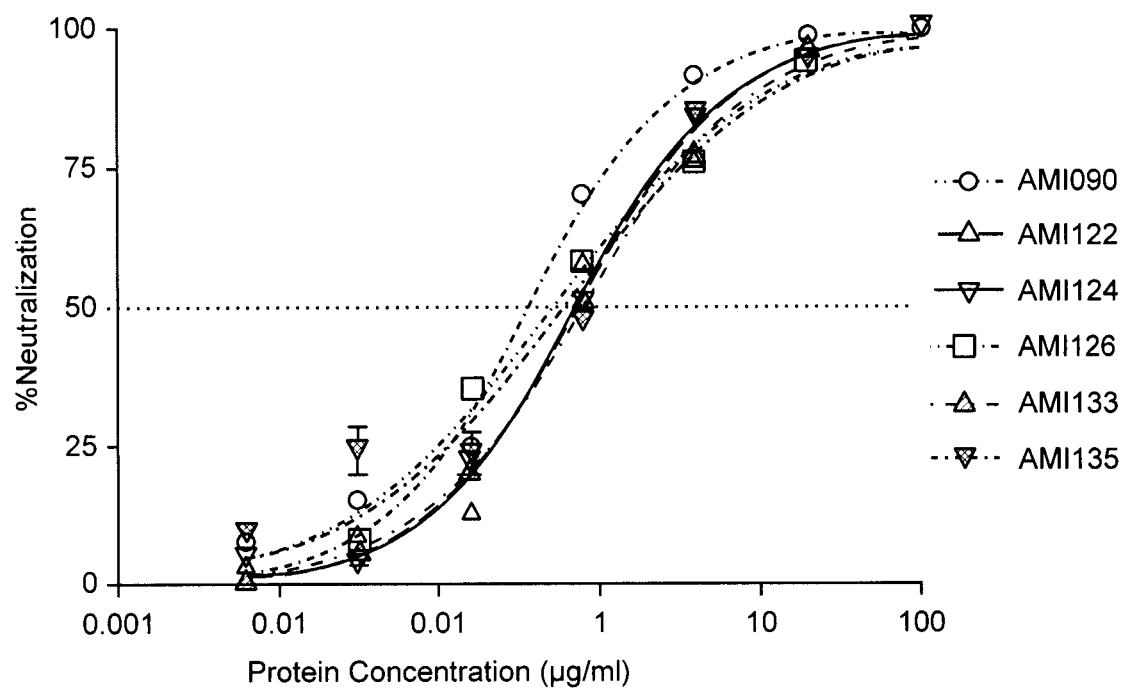
FIG. 20 shows neutralization of SARS-COV-2 S1 protein packed GFP-pseudovirus particles.
Figure 21:
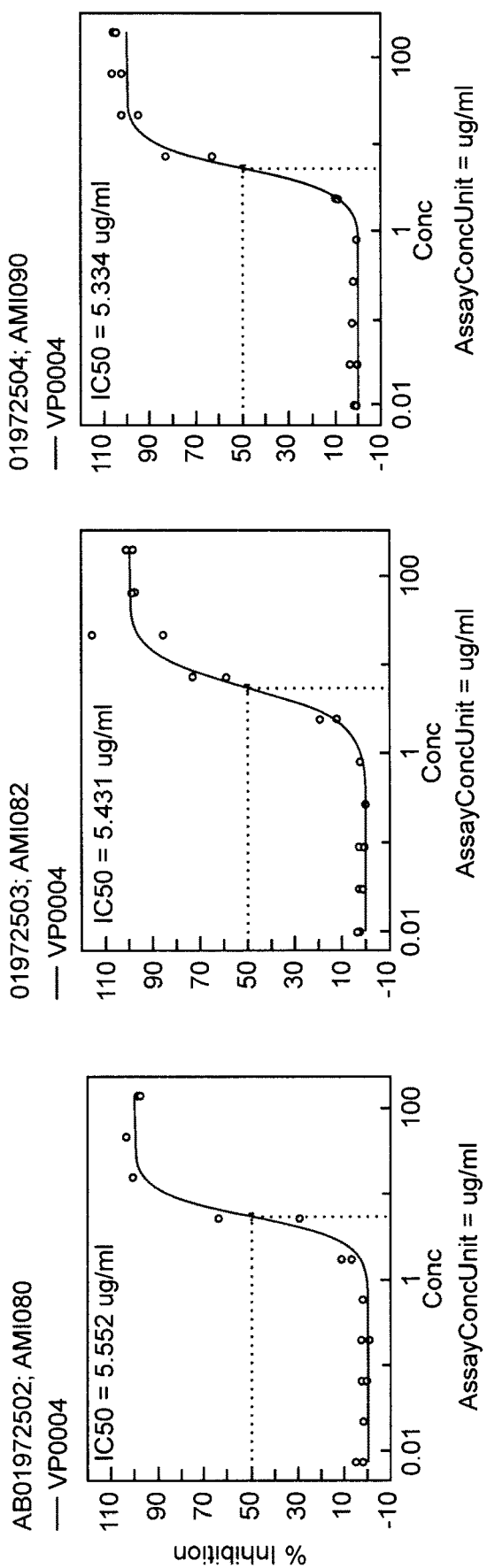
FIG. 21 shows neutralization of SARS-COV-2 wildtype virus (USA-WA1/2020) by variants of ACE-Fc fusion proteins of embodiments of the present disclosure.

The output of the assay is that 293T-hACE2 cells showed green fluorescent foci (GFF) in the absence of blocking or neutralization agents and no GFF was seen when specific neutralization reagent is present (FIG. 19). Neutralization of SARS-CoV-2 psuedovirus results are in FIG. 20 and FIG. 20. The 50% neutralization concentration is estimated about 5 µg/mL for ACE2-ECD-Fc, ACE2-vECD-Fc (AMI082) and ACE2-vECD-Fc (AMI090) respectively. The other three constructs, ACE2-vECD-Fc (AMI081), ACE2-vECD-Fc (AMI083 and ACE2-vECD-Fc (AMI084) is estimated at 10 µg/mL (FIG. 20).

8. Example: Efficacy of In Vitro SARS-CoV-2 Neutralization by $TCID_{50}$ Assay

The virulent neutralization assays were performed in Southern Research Institute (2000 Ninth Avenue South, Birmingham, Ala. 35205). The neutralization of SARS-CoV-2 by the selected ACE2-ECD-Fc (wildtype AMI080) or vACE2-ECD-Fc variant proteins (AMI082 and AMI090) were performed using Vero6 cell culture infected with virulent strain of SARS-CoV-2 (strain name: USA-WA1/2020, SARS-CoV-2).

The proteins, the gene plasmid DNA encoding the wild-type ACE2-ECD-Fc (AMI080), ACE2-vECD-Fc(AMI082) and vACE2-ECD-Fc (AMI090) were produced by transfecting monolayer cultures of HEK293 cells with AMI080, AMI082 and AMI090 plasmid DNA preparations separately. Protein preparations are summarized in Table 15.

TABLE 15

| Name | Length (aa) | Concentration, mg/mL | Molarity (μM) | Buffer |
|---|---|---|---|---|
| AMI080 | 949 | 0.87 | 3.99 | PBS, pH 7.0-7.2 |
| AMI082 | 949 | 1.20 | 5.51 | PBS, pH 7.0-7.2 |
| AMI090 | 949 | 1.20 | 5.50 | PBS, pH 7.0-7.2 |

Procedures for SARS-COV-2 coronavirus Cytopathic Effect (CPE) reduction assay (neutralization) is described below.

The first step is to dilute the ACE2-Fc proteins. AMI080, AMI02 and AMI090 were serially diluted in PBS are transferred into wells of an empty ECHO plate (stock plate) separately. The ACE2-Fc proteins were diluted 2-fold by transferring 40 μL of each stock sample into an adjacent well containing 40 μL PBS and mixing. This process was repeated to create 8 more wells of serially diluted sample, each well containing a 3-fold diluted sample of the previous well. A 90 nL aliquot for each sample is dispensed into corresponding wells of assay ready plates using an ECHO555 acoustic liquid handling system. The final assay concentration range was 200 to 0.01 μg/mL at 3-fold serial dilution. PBS is added to control wells to maintain a consistent assay concentration of 0.3% in all wells.

The second step was to measure antiviral effect of compounds:

Vero E6 cells were grown in MEM supplemented with 10% HI FBS and harvested in MEM, 1% Pen/Strep supplemented with 2% HI FBS on the day of assay. Assay ready plates pre-drugged with test compounds, AMI080, AMI082 and AMI00 were prepared in the BSL-2 lab by adding 5 μL assay media to each well. The plates and cells are then passed into the BSL-3 facility. Cells were batch inoculated with SARS CoV-2 (USA_WA1/2020; M.O.I.~0.002) which resulted in ~5% cell viability 72 hours post infection. A 25 μL aliquot of virus inoculated cells (4000 Vero E6 cells/well) was added to each well in columns 3-24 of the assay plates. The wells in columns 23-24 contained only virus infected cells for the 0% CPE reduction controls. Prior to virus inoculation, a 25 μL aliquot of cells was added to columns 1-2 of each plate for the cell only 100% CPE reduction controls. After incubating plates at 37° C./5% CO2 and 90% humidity for 72 hours, 30 μL of Cell Titer-Glo (Promega) is added to each well. Luminescence was read using a BMG CLARIOstar plate reader following incubation at room temperature for 10 minutes to measure cell viability. Plates are sealed with a clear cover and surface decontaminated prior to luminescence reading. To gain confidence of neutralization assays, several small viruses inhibitory Method for Measuring Cytotoxic Effect of ACE2-Fc Protein Preparations:

The cytotoxicity of ACE2-Fc protein, AMI080, AMI082 and AMI090 was assessed in a BSL-2 counter screen as follows: host cells in media were added in 25 μl aliquots (4000 cells/well) to each well of assay ready plates prepared with test proteins as above. Cells only (100% viability) and cells treated with hyamine at 100 μM final concentration (0% viability) serve as the high and low signal controls, respectively, for cytotoxic effect in the assay. PBS was maintained at a constant concentration for all wells as dictated by the dilution factor of stock these protein concentrations. After incubating plates at 37° C./5% $CO_2$ and 90% humidity for 72 hours, 30 μl Cell Titer-Glo (Promega) was added to each well. Luminescence was read using a BMG PHERAstar plate reader following incubation at room temperature for 10 minutes to measure cell viability.

Data Analysis:

For all assays the raw data from plate readers are imported into ActivityBase where values are associated with compound IDs and test concentrations.

For the antiviral CPE reduction assay, raw signal values are converted to % CPE reduction by the following formula:

% CPE reduction=100×(test protein value−mean value infected cell controls)/(mean value uninfected cell controls−mean value infected cell controls).

For the cell viability assay measuring compound cytotoxicity, % cell viability is calculated as follows:

% viability=100*(test protein value−mean low signal control)/(mean high signal control−mean low signal control).

The concentration of 50% inhibition of virus infection ($IC_{50}$) and the concentration causing 50% cytotoxicity ($CC_{50}$) were calculated from a four-parameter logistic fit of data using the Xlfit module of ActivityBase with top and bottom constrained to 100 and 0%, respectively. The analyzed data of SARS-COV-2 (USA-WA1/2020) are shown in FIG. 21, which indicate effective neutralization of SARS-COV-2 (USA-WA1/2020) achieved by the wildtype and the enzyme decoupled ACE2-Fc variants, AMI082 and AMI090.

The $IC_{50}$ of the three proteins were 5.55, 5.43 and 5.33 μg/mL for ACE2-Fc protein AMI080, AMI082 and AMI090 respectively. No significant difference was observed for the three constructs, thought the variant ACE2-Fc AMI082 and AMI090 showed 30-50-fold increase in affinity (KD) of S1 protein receptor binding assays.

9. Example: Production of Delivery Vectors of ACE2-ECD-Fc and ACE2-vECD-Fc Using Adeno Associated Viral Vector (AAV)

AAV5 is selected in the present invention because AAV5 is able to transduce airway epithelia cells, AAV5 by using sinus, nose, and/or lung delivery methods and other serotypes of AAV can also be used dependent on the target tissues or cells to be delivered. Several animal species including rats, cats, guinea pigs, hamsters, mice, mink, sheep, rabbits will be used.

AAV6 has a tendency to transduce lung cells preferentially. For this test, we start with AAV5 to produce vectors for delivery purposes.

The SF9 derived insect cell line, V432A cells were cultured in corning storage bottles at 28° C. in ESF AF medium (Expression Systems) supplemented with 100 units/ml penicillin and 100 µg/ml streptomycin (Corning). The cells were split 1:4 once the cell density reaches $7 \times 10^6$ cells/ml for maintenance.

Recombinant baculovirus (rBVs) were generated according to Invitrogen's protocol (Carlsbad, Calif.). Briefly, the constructed plasmids were used to transform DH10Bac and recombinant bacmid DNAs were isolated. The bacmid DNAs were transfected into V432A cells to generate rBVs. The rBVs were quantified with QPCR method.

AAV vector production, purification, and quantification—V432A cells were cultured to $7 \times 10^6$ cells/ml and diluted 1:1 with fresh ESF AF media. About 200 virus per cell of rBV containing the designated rep-cap genes and 100 virus per cell of rBV containing the DNA sequences encoding ACE2-ECD-Fc or ACE2-vECD-Fc variant proteins was added separately to infect the V432A cells for 3 days at 28° C. in shaker incubator. The infected V432A cells were harvested by centrifugation at 3,000 rpm for 10 min. Cell pellets were lysed in SF9 lysis buffer (50 mM Tris-HCl, pH7.8, 50 mM NaCl, 2 mM MgCl$_2$, 1% Sarkosyl, 1% Triton X-100, and 140 units/ml Benzonase®, Millipore, Burlington, Mass.). Genomic DNA was digested by incubation at 37° C. for one hour. At the end of incubation, sodium chloride was added to adjust the salt concentration of the lysate to about 1M to further dissociate the AAV vectors from cell matrix. Cell debris was removed by centrifugation at 8,000 rpm for 30 min. The cleared lysates were loaded onto CsCl step-gradient and subjected to ultracentrifugation at 28,000 rpm for 20 hours in swing bucket rotors. The viral band was drawn through a syringe with an 18-gauge needle and loaded onto a second CsCl and subjected to linear-ultracentrifugation at 65,000 rpm for 20 hours. Then the viral band was drawn and passed through two PD-10 desalting columns (GE HealthCare) to remove the CsCl and detergents and at the same time exchanged to Buffer B (1×PBS, 0.1M Sodium Citrate, and 0.001% pluronic F-68). Quantitative real-time PCR (qPCR) was performed to determine the AAV vector genome copy numbers with ITR primers and probe as below:

```
ITR-QPCR-F:
                                        (SEQ ID NO: 61)
5'-GGAACCCCTAGTGATGGAGTT-3'

ITR-QPCR-R:
                                        (SEQ ID NO: 62)
5'-CGGCCTCAGTGAGCGA-3'

ITR-FAM-2ITR-MGB:
                                        (SEQ ID NO: 63)
5'-CACTCCCTCTCTGCGCGCTCG-3'
```

SDS-PAGE and SimplyBlue-staining to verify the purity of AAV vectors—The AAV5 vectors were mixed with SDS-PAGE loading buffer (Invitrogen) and heated at 95° C. for 5 min. The vectors were then loaded onto a 10% SDS-PAGE gel and run at 100 volts until the dye reached the bottom of the gel. The gel was stained according to the manufacturer's protocol (Invitrogen).

In the experimentation, the AAV5-ACE2-ECD-Fc or AAV5-ACE2-vECD-Fc variant vector was produced and purified as described separately. The titer of each AAV5-ACE2-ECD-Fc or AAV5-ACE2-vECD-Fc variant vector was determined with primer pairs and probe selected from the ITR sequence as mentioned above. The titer, productivity and protein levels of these AAV vectors are shown in Table 16).

TABLE 16

Yields of AAV vectors determined with ITR-QPCR

| Lot no. | Vector name | AAV titer (vg/mL) | Total AAV Vol (mL) | Total Yield (vg) | Yield (vg/L) | Protein (µg/mL) |
|---|---|---|---|---|---|---|
| 20-067 | 5AMI089 ACE2-WT | 1.59E+13 | 4.6 | 7.33E+13 | 3.66E+14 | 286 |
| 20-057 | 5AMI082 (H374A-E402Q) | 2.09E+13 | 3.3 | 6.91E+13 | 2.30E+14 | 374 |
| 20-058 | 5AMI083 (E375-402Q) | 2.18E+13 | 4.3 | 9.38E+13 | 3.13E+14 | 419 |
| 20-059 | 5AMI084 (H374A-E375-402Q) | 1.67E+13 | 2 | 3.33E+13 | 1.11E+14 | 304 |
| 20-084 | 5AMI085 (H374A-E375Q) | 2.17E+13 | 5 | 1.08E+14 | 3.62E+14 | 541 |
| 20-085 | 5AMI081 (E402Q-G466D) | 2.76E+13 | 8 | 2.21E+14 | 1.10E+15 | 493 |
| 20-086 | 5AMI090 (E402Q) | 2.99E+13 | 12 | 3.58E+14 | 1.43E+15 | 494 |

SDS-PAGE and SimplyBlue Staining of AAV5 Vectors

Figure 22:
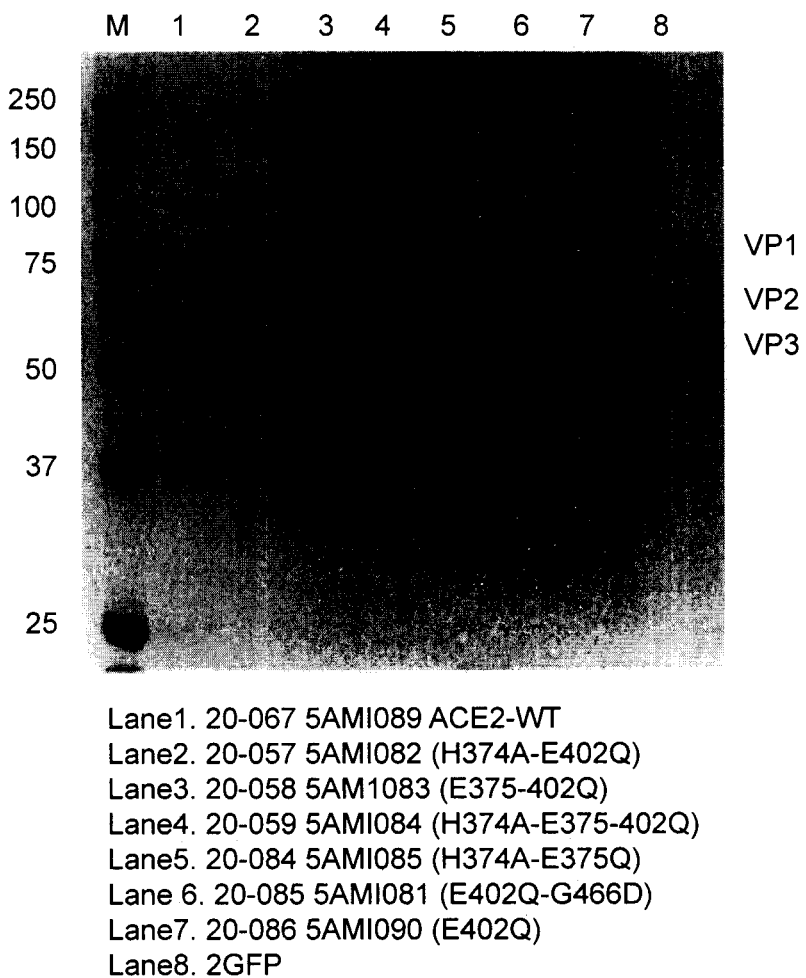
FIG. 22 shows staining assays of certain AAV vectors

The purity of AAV vectors is determined by SimplyBlue Staining assay. Briefly, 26 µl AAV samples were mixed with 10 µL of 4×loading buffer plus 4 µL 10×reducing reagent (Invitrogen), and incubate at 95° C. for 2 min. About 1E+11 vg of each AAV sample was loaded on each lane as indicated in the FIG. 22 description. A typical gel pattern was obtained with expected VP1, VP2 and VP3 component levels (FIG. 22).

ACE2-ECD-Fc and ACE2-vECD-Fc Expression by Recombinant AAV5 Vectors

The AAV5 vectors listed Table 11 were further evaluated for production of each construct protein using HEK293 cells. HEK293 cells were seeded at 1.5e+5 cells/well in 24-well plates and cultured overnight in 0.5 mL DMEM with 10% FBS. The next morning the cells were rinsed with serum-free DMEM and transduced with AAV5-ACE2 vectors at various titers in 0.5 mL serum-free DMEM with 20 µM etoposide. After overnight transduction, the inoculum was removed and replaced with 0.5 mL/well DMEM containing 10% FBS. After transduction for a total of 72 hours, cell media were collected, proteinase inhibitor added, and stored at ≤−65° C. before use.

The Expressed ACE2-vECD-Fc or ACE2-vECD-Fc Variants

HEK293 cell culture media (supernatants) collected 48 hours from plasmid transfection or 72 hours from AAV5-

ACE2 transduction were used for Western blot analysis. A total volume of 30 µl of cell supernatants was mixed with 10 ul of 4×loading buffer and loaded onto the NuPAGE 10% Tris-Glycine gels (Invitrogen) for electrophoresis. Proteins were subsequently transferred onto PVDF membranes using X Cell II™ Blot Module (Invitrogen, Carlsbad, Calif., USA). Membranes were treated with casein blocker in PBS (Thermo Scientific, Waltham, Mass., USA) for at least one hour at room temperature and probed with the goat anti-human IgG Fc antibody conjugated with biotin (Abcam, Cambridge, UK) followed by incubation with streptavidin conjugated with horseradish peroxidase (Abcam). Proteins were detected using the ECL™ Western blotting kit (Amersham) and photos recorded with iBright™ CL1500 Imaging System (Invitrogen).

Figure 23:
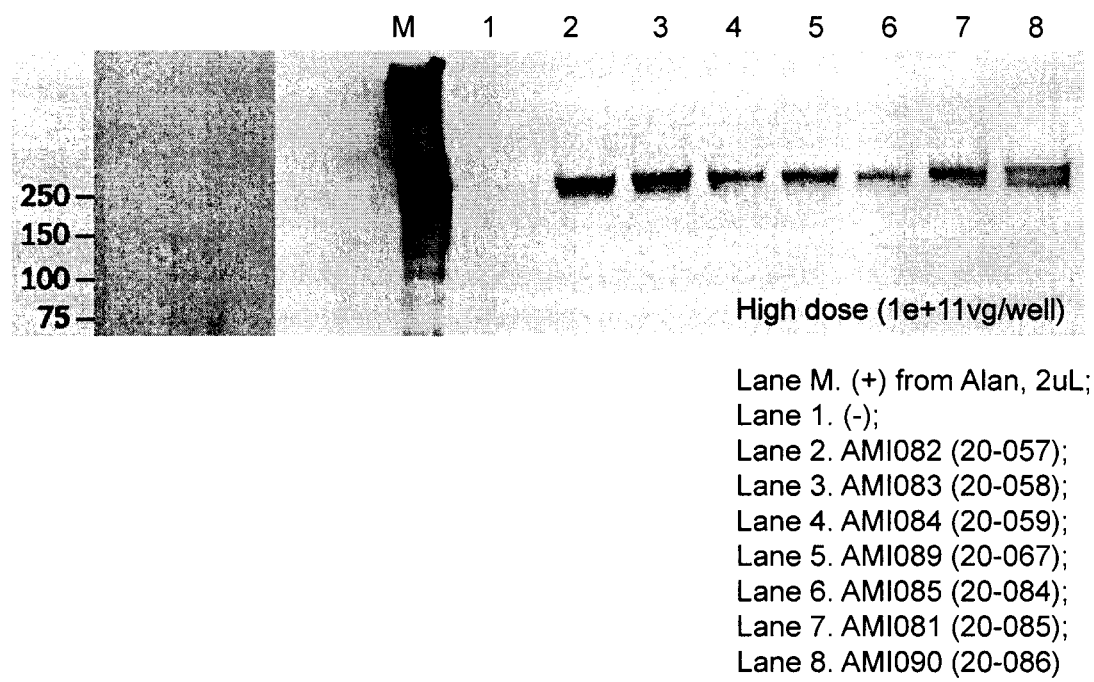
FIG. 23 shows SDS-PAGE and Western Blot of AAV5-ACE2-Fc and its variant from HEK293 Cells Culture Supernatant.

The western blot image showed a single and sharp band of about 250 kDa for each construct was detected using the non-reducing gel, indicating the vACE2-Fc constructs were expressed byHEK293 cells transduced with AAV5-ACE2-Fc viral vectors. In addition, a small portion of smaller sized protein, about 10-30%, was each in each lane implicated that the smaller protein is non glycosylated (FIG. 23).

Anti-Coronavirus Urgent Treatment

Treatment of coronavirus infection at urgent using recombinant ACE2-ECD-Fc or ACE2-vECD-Fc proteins.

The composition of the ACE2-ECD-Fc or ACE2-vECD-Fc are manufactured by recombination technologies as production process. The viruses include not limited to β group coronaviruses include severe respiratory syndrome (SARS) coronavirus (SARS-CoV-1), Middle East Respiratory syndrome (MERS) coronavirus (MERS-CoV) and recently the causative agents for the World pandemic CoVID-19, SARS-CoV-2 and low pathogenic of HCoV-NL63.

Generic Vaccine of SARS-CoV-1, SARS-CoV-2, MERS-CoV, and HCoV-NL63 Etc.

Prevention of coronavirus infection by injecting a single dose of AAV5-ACE2-vECD-Fc vector product which transduce many types of non-immune cells and producing sufficient level ACE2-vECD-Fc protein in vivo.

Once a virus particle enters into body, the ACE2-vECD-Fc functions as neutralization antibody, to bind viruses to form ACE2-vECD-Fc-SARS-CoV-2 complex which can be eliminated by both inert and active immune cells. This is in particularly valuable for elder people who immune function is low, and antibody cannot be bolstered when inactivated viral vaccine, RNA vaccine, cDNA vaccine and recombinant vaccines under development in the industry.

AAV can produce ACE2-vECD-Fc for many years at protective level. The approach is superior to any kind of vaccine is under development.

The ACE2-vECD-Fc DNA can be cloned into protein expression plasmid, used for transfection of mammalian cell line, yeast or other eumycotic expression system. The resultant cell line can be used for production of the ACE2-vECD-Fc protein product via large scale fermentation and a series of purification process steps. This product is used for urgent treatment of virus infection caused by SARS-CoV-1, SARS-CoV-2, MERS-CoV-1, or HCoV-NL63 infection, may be possible for future emerging coronavirus using the same receptor for entry. Furthermore, the virus: ACE2-vECD-Fc can be cleared through immune response pathways regulated by cells with $IgG_i$ receptors and ultimately terminate virus replication cycle.

The selected substitution mutants are cloned into adeno associated virus (AAV) packaging plasmid. The AAV carrying the gene of interest (GOI) ACE2-vECD-Fc is called AAV5-ACE2-vECD-Fc are manufactured and used for treatment and prevention from coronavirus infection.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

```
Sequence Listing
The extracellular domain (ECD) of human ACE2 amino acid sequence.
                                                                SEQ ID NO: 1
          qst ieeqaktfld kfnheaedlf yqsslaswny ntniteenvq 61   nmnnagdkws aflkeqstla qmyplqeiqn ltvklqlqal qqngssvlse dkskrlntil 121   ntmstiystg kvcnpdnpqe clllepglne imansldyne rlwaweswrs evgkqlrply 181   eeyvvlknem aranhyedyg dywrgdyevn gvdgydysrg qliedvehtf eeikplyehl 241   hayvraklmn aypsyispig clpahllgdm wgrfwtnlys ltvpfgqkpn idvtdamvdq 301   awdaqrifke aekffvsvgl pnmtqgfwen smltdpgnvq kavchptawd lgkgdfrilm 361   ctkvtmddfl tahhemghiq ydmayaaqpf llrnganegf heavgeimsl saatpkhlks 421   igllspdfqe dneteinfll kqaltivgtl pftymlekwr wmvfkgeipk dqwmkkwwem 481   kreivgvvep vphdetycdp aslfhvsndy sfiryytrtl yqfqfqealc qaakhegplh
```

-continued

```
541   kcdisnstea gqklfnmlrl gksepwtlal envvgaknmn vrpllnyfep lftwlkdqnk
601   nsfvgwstdw spyadqsikv rislksalgd kayewndnem ylfrssvaya mrqyflkvkn
661   qmilfgeedv rvanlkpris fnffvtapkn vsdiiprtev ekairmsrsr indafrindn
721   sleflgiqpt lgppnqppvs
``` ctkvtmddfl tahhemghiq ydmayaaqpf llrnganegf heavgeimsl    SEQ ID NO: 2 ctkvtmddfl tahhemghiq ydmayaaqpf llrnganegf hQavgeimsl    SEQ ID NO: 3 ctkvtmddfl tahAemghiq ydmayaaqpf llrnganegf hQavgeimsl    SEQ ID NO: 4 ctkvtmddfl tahhemgAiq ydmayaaqpf llrnganegf hQavgeimsl    SEQ ID NO: 5 ctkvtmddfl tahAemghiq ydmayaaqpf llrnganegf heavgeimsl    SEQ ID NO: 6 ctkvtmddfl tahhemgAiq ydmayaaqpf llrnganegf heavgeimsl    SEQ ID NO: 7 ctkvtmddfl tahAemgAiq ydmayaaqpf llrnganegf heavgeimsl    SEQ ID NO: 8 ctkvtmddfl tahhQmghiq ydmayaaqpf llrnganegf hQavgeimsl    SEQ ID NO: 9 ctkvtmddfl tahAQmghiq ydmayaaqpf llrnganegf hQavgeimsl    SEQ ID NO: 10 ctkvtmddfl tahhQmgAiq ydmayaaqpf llrnganegf hQavgeimsl    SEQ ID NO: 11 ctkvtmddfl tahAQmgAiq ydmayaaqpf llrnganegf hQavgeimsl    SEQ ID NO: 12 ctkvtmddfl tahAQmghiq ydmayaaqpf llrnganegf heavgeimsl    SEQ ID NO: 13 ctkvtmddfl tahhQmgAiq ydmayaaqpf llrnganegf heavgeimsl    SEQ ID NO: 14 ctkvtmddfl tahAQmgAiq ydmayaaqpf llrnganegf heavgeimsl    SEQ ID NO: 15

AMI074/G466D
CTKVTMDDF

AMI124                                                              SEQ ID NO: 23
CTKVTMDDFLTAHAEMGRIQYDMAYALQPFLLRNGANEGFHQAVGEIMSL

AMI125                                                              SEQ ID NO: 24
CTKVTMDDFLTAHAEMGAIQYDMAYALQPFLLRNGANEGFHQAVGEIMSL

AMI126                                                              SEQ ID NO: 25
CTKVTMDDFLTAHAEMGRIQYDMAYALQPFLLRNGANEGFHQAVGEIMSL

AMI127                                                              SEQ ID NO: 26
CTKVTMDDFLTAHLEMGHIQYDMAYALQPFLLRNGANEGFHQAVGEIMSL

AMI128                                                              SEQ ID NO: 27
CTKVTMDDFLTAHAEMGHIQYDMAYALQPFLLRNGANEGFHQAVGEIMSL

AMI129                                                              SEQ ID NO: 28
CTKVTMDDFLTAHLEMGRIQYDMAYALQPFLLRNGANEGFHQAVGEIMSL

ACE2-ECD-Fc (Wildtype)                                              SEQ ID NO: 29
  18    qst ieeqaktfld kfnheaedlf yqsslaswny ntniteenvq
  61    nmnnagdkws aflkeqstlaqmyplqeiqnltvklqlqalqqngssvlse dkskrlntil
 121    ntmstiystg kvcnpdnpqe clllepglne imansldyne rlwaweswrs evgkqlrply
 181    eeyvvlknem aranhyedyg dywrgdyevn gvdgydysrg qliedvehtf eeikplyehl
 241    hayvraklmn aypsyispig clpahllgdm wgrfwtnlys ltvpfgqkpn idvtdamvdq
 301    awdaqrifke aekffvsvgl pnmtqgfwen smltdpgnvq kavchptawd lgkgdfrilm
 361    ctkvtmddfl tahhemghiq ydmayaaqpf llrnganegf heavgeimsl saatpkhlks
 421    igllspdfqe dneteinfll kqaltivgtl pftymlekwr wmvfkgeipk dqwmkkwwem
 481    kreivgvvep vphdetycdp aslfhvsndy sfiryytrtl yqfqfqealc qaakhegplh
 541    kcdisnstea gqklfnmlrl gksepwtlal envvgaknmn vrpllnyfep lftwlkdqnk
 601    nsfvgwstdw spyadqsikv rislksalgd kayewndnem ylfrssvaya mrqyflkvkn
 661    qmilfgeedv rvanlkpris fnffvtapkn vsdiiprtev ekairmsrsr indafrlndn
 721    sleflgiqpt lgppnqppvs dkthtcppcpapellggpsvflfppkpkdtlmisr
        tpevtcvvvdvshedpevkfnwyvdgvevhnaktkpreeqynstyrvvsvltvlhqdwlngkeykckvsnkal
        papiektiskakgqprepqvytlppsrdeltknqvsltclvkgfypsdiavewesngqpennykttppvldsd
        gsffflyskltvdksrwqqgnvfscsvmh A024                                                                SEQ ID NO: 33
ATCCAGCCTCCGGACTCTAGAGTTAACTGGTAAGTTTAGT A056                                                                SEQ ID NO: 34
GTTGCCTTTACTTCTAGGCCTGCCGCCACCatgGAGTTCGGCCTGAGCTGGCTGTTCCT A074                                                                SEQ ID NO: 35
AACAGCTATGACCATG A098                                                                SEQ ID NO: 36
ATGTACGGGCCAGATATACGCGTTCGTTACATAACTTACGGTAAA A120                                                                SEQ ID NO: 37
TGATTATTGACTAGTATCTGCGTTACATAACTTACGGTAA A121                                                                SEQ ID NO: 38
ACTCcatGGTGGCGGCAGGCCTAGAAGTAAAGGCAACATC -continued

A122
ATAAAGATATTTTATTTTCGAATTCTCAGC
SEQ ID NO: 39

A123
CTGTTCTACCAGAGCAGCCTGGCCA
SEQ ID NO: 40

A124
CTGGGAGAACAGCATGCTGACCGAC
SEQ ID NO: 41

A125
AGAGCATCAAGGTGAGAATCAGCCT
SEQ ID NO: 42

A126
CGGCCAGCCCGAGAACAACTACAAG
SEQ ID NO: 43

A145
TCGTGGGGCACGGGCTCCACCACGC
SEQ ID NO: 44

A146
GCGTGGTGGAGCCCGTGCCCCACGA
SEQ ID NO: 45

A147
TGGGGGGGAACAGGAACACGCTGGG
SEQ ID NO: 46

A148
GCGGCCCCAGCGTGTTCCTGTTCCC
SEQ ID NO: 47

A156
GAATCCTGATGTGCACCAAGGTGACCATGGACGACTTCC
SEQ ID NO: 48

A157
GGTGACCATGGACGACTTCCTGACCGCCCACGCCGAGATGGGCCACATC
SEQ ID NO: 49

A158
GCATGTTGAACAGCTTCT
SEQ ID NO: 50

A159
GACCATGGACGACTTCCTGACCGCCCACCACCAGATGGGCCACATCCAG
SEQ ID NO: 51

A160
GACCATGGACGACTTCCTGACCGCCCACGCCCAGATGGGCCACATCCAG
SEQ ID NO: 52

A161
CGCCAAGCTCTAGCTAGAGGTCGACGCGGCCGCTCGGTCCGCAC
SEQ ID NO: 53

A162
TTCCTGCTGAGAAACGGCGCCAACGAGGGCTTCCACcAGGCCGTGGGCG
SEQ ID NO: 54

A163
GGGGTCTCACGTTCATGTTC
SEQ ID NO: 55

A169
GAGATGGATGGTGTTCAAGGGCGAGATCCCCAAGGACCAG
SEQ ID NO: 56

A170
CTGGTCCTTGGGGATCTCGCCCTTGAACACCATCCATC
SEQ ID NO: 57

A385
CCGAAGGGCACGGTCAGGCTGTACA
SEQ ID NO: 58

-continued

A386

(SEQ ID NO: 59)

TGTACAGCCTGACCGTGCCCTTCGG

ITR-QPCR-F:

(SEQ ID NO: 61)

5'-GGAACCCCTAGTGATGGAGTT-3'

ITR-QPCR-R:

(SEQ ID NO: 62)

5'-CGGCCTCAGTGAGCGA-3'

ITR-FAM-2ITR-MGB:

(SEQ ID NO: 63)

5'-CACTCCCTCTCTGCGCGCTCG-3'

Attachment: Complete DNA Sequences of Each ACE2-ECD-Fc or ACE2-vECD-Fc Variant

AMI074

SEQ ID NO: 64

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACGAGATGGGCCACATCCAGTACGACATGGCCTACGCCGCCCAGCCCTTCCTG

CTGAGAAACGGCGCCAACGAGGGCTTCCACGAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGaC

GAGATCCCCAAGGACCAGTGGATGAAGAAGTGGTGGGAGATGAAGAGAGAGATCG

TGGGCGTGGTGGAGCCCGTGCCCCACGACGAGACCTACTGCGACCCCGCCAGCCTG

TTCCACGTGAGCAACGACTACAGCTTCATCAGATACTACACCAGAACCCTGTACCAG

TTCCAGTTCCAGGAGGCCCTGTGCCAGGCCGCCAAGCACGAGGGCCCCCTGCACAA

GTGCGACATCAGCAACAGCACCGAGGCCGGCCAGAAGCTGTTCAACATGCTGAGAC

TGGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

-continued

```
CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI080                                                          SEQ ID NO: 65

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACGAGATGGGCCACATCCAGTACGACATGGCCTACGCCGCCCAGCCCTTCCTG
```

-continued

CTGAGAAACGGCGCCAACGAGGGCTTCCACGAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGG

CGAGATCCCCAAGGACCAGTGGATGAAGAAGTGGTGGGAGATGAAGAGAGAGATC

GTGGGCGTGGTGGAGCCCGTGCCCCACGACGAGACCTACTGCGACCCCGCCAGCCT

GTTCCACGTGAGCAACGACTACAGCTTCATCAGATACTACACCAGAACCCTGTACCA

GTTCCAGTTCCAGGAGGCCCTGTGCCAGGCCGCCAAGCACGAGGGCCCCCTGCACA

AGTGCGACATCAGCAACAGCACCGAGGCCGGCCAGAAGCTGTTCAACATGCTGAGA

CTGGGCAAGAGCGAGCCCTGGACCCTGGCCCTGGAGAACGTGGTGGGCGCCAAGAA

CATGAACGTGAGACCCCTGCTGAACTACTTCGAGCCCCTGTTCACCTGGCTGAAGGA

CCAGAACAAGAACAGCTTCGTGGGCTGGAGCACCGACTGGAGCCCCTACGCCGACC

AGAGCATCAAGGTGAGAATCAGCCTGAAGAGCGCCCTGGGCGACAAGGCCTACGA

GTGGAACGACAACGAGATGTACCTGTTCAGAAGCAGCGTGGCCTACGCCATGAGAC

AGTACTTCCTGAAGGTGAAGAACCAGATGATCCTGTTCGGCGAGGAGGACGTGAGA

GTGGCCAACCTGAAGCCCAGAATCAGCTTCAACTTCTTCGTGACCGCCCCCAAGAAC

GTGAGCGACATCATCCCCAGAACCGAGGTGGAGAAGGCCATCAGAATGAGCAGAA

GCAGAATCAACGACGCCTTCAGACTGAACGACAACAGCCTGGAGTTCCTGGGCATC

CAGCCCACCCTGGGCCCCCCCAACCAGCCCCCCGTGAGCGACAAGACCCACACCTG

CCCCCCCTGCCCCGCCCCCGAGCTGCTGGGCGGCCCCAGCGTGTTCCTGTTCCCCCC

CAAGCCCAAGGACACCCTGATGATCAGCAGAACCCCCGAGGTGACCTGCGTGGTGG

TGGACGTGAGCCACGAGGACCCCGAGGTGAAGTTCAACTGGTACGTGGACGGCGTG

GAGGTGCACAACGCCAAGACCAAGCCCAGAGAGGAGCAGTACAACAGCACCTACA

GAGTGGTGAGCGTGCTGACCGTGCTGCACCAGGACTGGCTGAACGGCAAGGAGTAC

AAGTGCAAGGTGAGCAACAAGGCCCTGCCCGCCCCCATCGAGAAGACCATCAGCAA

GGCCAAGGGCCAGCCCAGAGAGCCCCAGGTGTACACCCTGCCCCCCAGCAGAGACG

AGCTGACCAAGAACCAGGTGAGCCTGACCTGCCTGGTGAAGGGCTTCTACCCCAGC

GACATCGCCGTGGAGTGGGAGAGCAACGGCCAGCCCGAGAACAACTACAAGACCA

CCCCCCCCGTGCTGGACAGCGACGGCAGCTTCTTCCTGTACAGCAAGCTGACCGTGG

ACAAGAGCAGATGGCAGCAGGGCAACGTGTTCAGCTGCAGCGTGATGCACGAGGCC

CTGCACAACCACTACACCCAGAAGAGCCTGAGCCTGAGCCCCGGCTGA

AMI081

CAGAGCACCATCGAGGAGCAGGCCAAGACCTTCCTGGACAAGTTCAACCACGAGGC

SEQ ID NO: 66

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

```
GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACGAGATGGGCCACATCCAGTACGACATGGCCTACGCCGCCCAGCCCTTCCTG

CTGAGAAACGGCGCCAACGAGGGCTTCCACcAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGaC

GAGATCCCCAAGGACCAGTGGATGAAGAAGTGGTGGGAGATGAAGAGAGAGATCG

TGGGCGTGGTGGAGCCCGTGCCCCACGACGAGACCTACTGCGACCCCGCCAGCCTG

TTCCACGTGAGCAACGACTACAGCTTCATCAGATACTACACCAGAACCCTGTACCAG

TTCCAGTTCCAGGAGGCCCTGTGCCAGGCCGCCAAGCACGAGGGCCCCCTGCACAA

GTGCGACATCAGCAACAGCACCGAGGCCGGCCAGAAGCTGTTCAACATGCTGAGAC

TGGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA
```

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI082                                                          SEQ ID NO: 67

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCGAGATGGGCCACATCCAGTACGACATGGCCTACGCCGCCCAGCCCTTCCTG

CTGAGAAACGGCGCCAACGAGGGCTTCCACcAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGG

CGAGATCCCCAAGGACCAGTGGATGAAGAAGTGGTGGGAGATGAAGAGAGAGATC

GTGGGCGTGGTGGAGCCCGTGCCCCACGACGAGACCTACTGCGACCCCGCCAGCCT

GTTCCACGTGAGCAACGACTACAGCTTCATCAGATACTACACCAGAACCCTGTACCA

GTTCCAGTTCCAGGAGGCCCTGTGCCAGGCCGCCAAGCACGAGGGCCCCCTGCACA

AGTGCGACATCAGCAACAGCACCGAGGCCGGCCAGAAGCTGTTCAACATGCTGAGA

CTGGGCAAGAGCGAGCCCTGGACCCTGGCCCTGGAGAACGTGGTGGGCGCCAAGAA

CATGAACGTGAGACCCCTGCTGAACTACTTCGAGCCCCTGTTCACCTGGCTGAAGGA

CCAGAACAAGAACAGCTTCGTGGGCTGGAGCACCGACTGGAGCCCCTACGCCGACC

AGAGCATCAAGGTGAGAATCAGCCTGAAGAGCGCCCTGGGCGACAAGGCCTACGA

GTGGAACGACAACGAGATGTACCTGTTCAGAAGCAGCGTGGCCTACGCCATGAGAC

AGTACTTCCTGAAGGTGAAGAACCAGATGATCCTGTTCGGCGAGGAGGACGTGAGA

GTGGCCAACCTGAAGCCCAGAATCAGCTTCAACTTCTTCGTGACCGCCCCCAAGAAC

GTGAGCGACATCATCCCCAGAACCGAGGTGGAGAAGGCCATCAGAATGAGCAGAA

-continued

```
GCAGAATCAACGACGCCTTCAGACTGAACGACAACAGCCTGGAGTTCCTGGGCATC

CAGCCCACCCTGGGCCCCCCCAACCAGCCCCCCGTGAGCGACAAGACCCACACCTG

CCCCCCCTGCCCCGCCCCCGAGCTGCTGGGCGGCCCCAGCGTGTTCCTGTTCCCCCC

CAAGCCCAAGGACACCCTGATGATCAGCAGAACCCCCGAGGTGACCTGCGTGGTGG

TGGACGTGAGCCACGAGGACCCCGAGGTGAAGTTCAACTGGTACGTGGACGGCGTG

GAGGTGCACAACGCCAAGACCAAGCCCAGAGAGGAGCAGTACAACAGCACCTACA

GAGTGGTGAGCGTGCTGACCGTGCTGCACCAGGACTGGCTGAACGGCAAGGAGTAC

AAGTGCAAGGTGAGCAACAAGGCCCTGCCCGCCCCCATCGAGAAGACCATCAGCAA

GGCCAAGGGCCAGCCCAGAGAGCCCCAGGTGTACACCCTGCCCCCCAGCAGAGACG

AGCTGACCAAGAACCAGGTGAGCCTGACCTGCCTGGTGAAGGGCTTCTACCCCAGC

GACATCGCCGTGGAGTGGGAGAGCAACGGCCAGCCCGAGAACAACTACAAGACCA

CCCCCCCCGTGCTGGACAGCGACGGCAGCTTCTTCCTGTACAGCAAGCTGACCGTGG

ACAAGAGCAGATGGCAGCAGGGCAACGTGTTCAGCTGCAGCGTGATGCACGAGGCC

CTGCACAACCACTACACCCAGAAGAGCCTGAGCCTGAGCCCCGGCTGA
```

AMI083
SEQ ID NO: 68

```
CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACcAGATGGGCCACATCCAGTACGACATGGCCTACGCCGCCCAGCCCTTCCTG

CTGAGAAACGGCGCCAACGAGGGCTTCCACcAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGG

CGAGATCCCCAAGGACCAGTGGATGAAGAAGTGGTGGGAGATGAAGAGAGAGATC

GTGGGCGTGGTGGAGCCCGTGCCCCACGACGAGACCTACTGCGACCCCGCCAGCCT
```

-continued

```
GTTCCACGTGAGCAACGACTACAGCTTCATCAGATACTACACCAGAACCCTGTACCA
GTTCCAGTTCCAGGAGGCCCTGTGCCAGGCCGCCAAGCACGAGGGCCCCCTGCACA
AGTGCGACATCAGCAACAGCACCGAGGCCGGCCAGAAGCTGTTCAACATGCTGAGA
CTGGGCAAGAGCGAGCCCTGGACCCTGGCCCTGGAGAACGTGGTGGGCGCCAAGAA
CATGAACGTGAGACCCCTGCTGAACTACTTCGAGCCCCTGTTCACCTGGCTGAAGGA
CCAGAACAAGAACAGCTTCGTGGGCTGGAGCACCGACTGGAGCCCCTACGCCGACC
AGAGCATCAAGGTGAGAATCAGCCTGAAGAGCGCCCTGGGCGACAAGGCCTACGA
GTGGAACGACAACGAGATGTACCTGTTCAGAAGCAGCGTGGCCTACGCCATGAGAC
AGTACTTCCTGAAGGTGAAGAACCAGATGATCCTGTTCGGCGAGGAGGACGTGAGA
GTGGCCAACCTGAAGCCCAGAATCAGCTTCAACTTCTTCGTGACCGCCCCCAAGAAC
GTGAGCGACATCATCCCCAGAACCGAGGTGGAGAAGGCCATCAGAATGAGCAGAA
GCAGAATCAACGACGCCTTCAGACTGAACGACAACAGCCTGGAGTTCCTGGGCATC
CAGCCCACCCTGGGCCCCCCAACCAGCCCCCCGTGAGCGACAAGACCCACACCTG
CCCCCCTGCCCCGCCCCCGAGCTGCTGGGCGGCCCCAGCGTGTTCCTGTTCCCCCC
CAAGCCCAAGGACACCCTGATGATCAGCAGAACCCCCGAGGTGACCTGCGTGGTGG
TGGACGTGAGCCACGAGGACCCCGAGGTGAAGTTCAACTGGTACGTGGACGGCGTG
GAGGTGCACAACGCCAAGACCAAGCCCAGAGAGGAGCAGTACAACAGCACCTACA
GAGTGGTGAGCGTGCTGACCGTGCTGCACCAGGACTGGCTGAACGGCAAGGAGTAC
AAGTGCAAGGTGAGCAACAAGGCCCTGCCCGCCCCCATCGAGAAGACCATCAGCAA
GGCCAAGGGCCAGCCCAGAGAGCCCCAGGTGTACACCCTGCCCCCCAGCAGAGACG
AGCTGACCAAGAACCAGGTGAGCCTGACCTGCCTGGTGAAGGGCTTCTACCCCAGC
GACATCGCCGTGGAGTGGGAGAGCAACGGCCAGCCCGAGAACAACTACAAGACCA
CCCCCCCCGTGCTGGACAGCGACGGCAGCTTCTTCCTGTACAGCAAGCTGACCGTGG
ACAAGAGCAGATGGCAGCAGGGCAACGTGTTCAGCTGCAGCGTGATGCACGAGGCC
CTGCACAACCACTACACCCAGAAGAGCCTGAGCCTGAGCCCCGGCTGA
```

AMI084 SEQ ID NO: 69

```
CAGAGCACCATCGAGGAGCAGGCCAAGACCTTCCTGGACAAGTTCAACCACGAGGC
CGAGGACCTGTTCTACCAGAGCAGCCTGGCCAGCTGGAACTACAACACCAACATCA
CCGAGGAGAACGTGCAGAACATGAACAACGCCGGCGACAAGTGGAGCGCCTTCCTG
AAGGAGCAGAGCACCCTGGCCCAGATGTACCCCCTGCAGGAGATCCAGAACCTGAC
CGTGAAGCTGCAGCTGCAGGCCCTGCAGCAGAACGGCAGCAGCGTGCTGAGCGAGG
ACAAGAGCAAGAGACTGAACACCATCCTGAACACCATGAGCACCATCTACAGCACC
GGCAAGGTGTGCAACCCCGACAACCCCCAGGAGTGCCTGCTGCTGGAGCCCGGCCT
GAACGAGATCATGGCCAACAGCCTGGACTACAACGAGAGACTGTGGGCCTGGGAGA
GCTGGAGAAGCGAGGTGGGCAAGCAGCTGAGACCCCTGTACGAGGAGTACGTGGTG
CTGAAGAACGAGATGGCCAGAGCCAACCACTACGAGGACTACGGCGACTACTGGAG
AGGCGACTACGAGGTGAACGGCGTGGACGGCTACGACTACAGCAGAGGCCAGCTG
ATCGAGGACGTGGAGCACACCTTCGAGGAGATCAAGCCCCTGTACGAGCACCTGCA
CGCCTACGTGAGAGCCAAGCTGATGAACGCCTACCCCAGCTACATCAGCCCCATCG
GCTGCCTGCCCGCCCACCTGCTGGGCGACATGTGGGGCAGATTCTGGACCAACCTGT
```

```
                          -continued
ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCcAGATGGGCCACATCCAGTACGACATGGCCTACGCCGCCCAGCCCTTCCTGC

TGAGAAACGGCGCCAACGAGGGCTTCCACcAGGCCGTGGGCGAGATCATGAGCCTG

AGCGCCGCCACCCCCAAGCACCTGAAGAGCATCGGCCTGCTGAGCCCCGACTTCCA

GGAGGACAACGAGACCGAGATCAACTTCCTGCTGAAGCAGGCCCTGACCATCGTGG

GCACCCTGCCCTTCACCTACATGCTGGAGAAGTGGAGATGGATGGTGTTCAAGGGC

GAGATCCCCAAGGACCAGTGGATGAAGAAGTGGTGGGAGATGAAGAGAGAGATCG

TGGGCGTGGTGGAGCCCGTGCCCCACGACGAGACCTACTGCGACCCCGCCAGCCTG

TTCCACGTGAGCAACGACTACAGCTTCATCAGATACTACACCAGAACCCTGTACCAG

TTCCAGTTCCAGGAGGCCCTGTGCCAGGCCGCCAAGCACGAGGGCCCCCTGCACAA

GTGCGACATCAGCAACAGCACCGAGGCCGGCCAGAAGCTGTTCAACATGCTGAGAC

TGGGCAAGAGCGAGCCCTGGACCCTGGCCCTGGAGAACGTGGTGGGCGCCAAGAAC

ATGAACGTGAGACCCCTGCTGAACTACTTCGAGCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCGAGCTGCTGGGCGGCCCCAGCGTGTTCCTGTTCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI085                                                    SEQ ID NO: 70
CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG
```

```
AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCcAGATGGGCCACATCCAGTACGACATGGCCTACGCCGCCCAGCCCTTCCTGC

TGAGAAACGGCGCCAACGAGGGCTTCCACGAGGCCGTGGGCGAGATCATGAGCCTG

AGCGCCGCCACCCCCAAGCACCTGAAGAGCATCGGCCTGCTGAGCCCCGACTTCCA

GGAGGACAACGAGACCGAGATCAACTTCCTGCTGAAGCAGGCCCTGACCATCGTGG

GCACCCTGCCCTTCACCTACATGCTGGAGAAGTGGAGATGGATGGTGTTCAAGGGC

GAGATCCCCAAGGACCAGTGGATGAAGAAGTGGTGGGAGATGAAGAGAGAGATCG

TGGGCGTGGTGGAGCCCGTGCCCCACGACGAGACCTACTGCGACCCCGCCAGCCTG

TTCCACGTGAGCAACGACTACAGCTTCATCAGATACTACACCAGAACCCTGTACCAG

TTCCAGTTCCAGGAGGCCCTGTGCCAGGCCGCCAAGCACGAGGGCCCCCTGCACAA

GTGCGACATCAGCAACAGCACCGAGGCCGGCCAGAAGCTGTTCAACATGCTGAGAC

TGGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA
```

-continued

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI089

SEQ ID NO: 71

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACGAGATGGGCCACATCCAGTACGACATGGCCTACGCCGCCCAGCCCTTCCTG

CTGAGAAACGGCGCCAACGAGGGCTTCCACGAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGG

CGAGATCCCCAAGGACCAGTGGATGAAGAAGTGGTGGGAGATGAAGAGAGAGATC

GTGGGCGTGGTGGAGCCCGTGCCCCACGACGAGACCTACTGCGACCCCGCCAGCCT

GTTCCACGTGAGCAACGACTACAGCTTCATCAGATACTACACCAGAACCCTGTACCA

GTTCCAGTTCCAGGAGGCCCTGTGCCAGGCCGCCAAGCACGAGGGCCCCCTGCACA

AGTGCGACATCAGCAACAGCACCGAGGCCGGCCAGAAGCTGTTCAACATGCTGAGA

CTGGGCAAGAGCGAGCCCTGGACCCTGGCCCTGGAGAACGTGGTGGGCGCCAAGAA

CATGAACGTGAGACCCCTGCTGAACTACTTCGAGCCCCTGTTCACCTGGCTGAAGGA

CCAGAACAAGAACAGCTTCGTGGGCTGGAGCACCGACTGGAGCCCCTACGCCGACC

-continued

AGAGCATCAAGGTGAGAATCAGCCTGAAGAGCGCCCTGGGCGACAAGGCCTACGA

GTGGAACGACAACGAGATGTACCTGTTCAGAAGCAGCGTGGCCTACGCCATGAGAC

AGTACTTCCTGAAGGTGAAGAACCAGATGATCCTGTTCGGCGAGGAGGACGTGAGA

GTGGCCAACCTGAAGCCCAGAATCAGCTTCAACTTCTTCGTGACCGCCCCCAAGAAC

GTGAGCGACATCATCCCCAGAACCGAGGTGGGAGAAGGCCATCAGAATGAGCAGAA

GCAGAATCAACGACGCCTTCAGACTGAACGACAACAGCCTGGAGTTCCTGGGCATC

CAGCCCACCCTGGGCCCCCCCAACCAGCCCCCCGTGAGCGACAAGACCCACACCTG

CCCCCCCTGCCCCGCCCCCGAGCTGCTGGGCGGCCCCAGCGTGTTCCTGTTCCCCCC

CAAGCCCAAGGACACCCTGATGATCAGCAGAACCCCCGAGGTGACCTGCGTGGTGG

TGGACGTGAGCCACGAGGACCCCGAGGTGAAGTTCAACTGGTACGTGGACGGCGTG

GAGGTGCACAACGCCAAGACCAAGCCCAGAGAGGAGCAGTACAACAGCACCTACA

GAGTGGTGAGCGTGCTGACCGTGCTGCACCAGGACTGGCTGAACGGCAAGGAGTAC

AAGTGCAAGGTGAGCAACAAGGCCCTGCCCGCCCCCATCGAGAAGACCATCAGCAA

GGCCAAGGGCCAGCCCAGAGAGCCCCAGGTGTACACCCTGCCCCCCAGCAGAGACG

AGCTGACCAAGAACCAGGTGAGCCTGACCTGCCTGGTGAAGGGCTTCTACCCCAGC

GACATCGCCGTGGAGTGGGAGAGCAACGGCCAGCCCGAGAACAACTACAAGACCA

CCCCCCCCGTGCTGGACAGCGACGGCAGCTTCTTCCTGTACAGCAAGCTGACCGTGG

ACAAGAGCAGATGGCAGCAGGGCAACGTGTTCAGCTGCAGCGTGATGCACGAGGCC

CTGCACAACCACTACACCCAGAAGAGCCTGAGCCTGAGCCCCGGCTGA

AMI090

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACCACGAGATGGGCCACATCCAGTACGACATGGCCTACGCCGCCCAGCCCTTCCTG

SEQ ID NO: 72

-continued

CTGAGAAACGGCGCCAACGAGGGCTTCCACcAGGCCGTGGGCGAGATCATGAGCCT

GAGCGCCGCCACCCCCAAGCACCTGAAGAGCATCGGCCTGCTGAGCCCCGACTTCC

AGGAGGACAACGAGACCGAGATCAACTTCCTGCTGAAGCAGGCCCTGACCATCGTG

GGCACCCTGCCCTTCACCTACATGCTGGAGAAGTGGAGATGGATGGTGTTCAAGGG

CGAGATCCCCAAGGACCAGTGGATGAAGAAGTGGTGGGAGATGAAGAGAGAGATC

GTGGGCGTGGTGGAGCCCGTGCCCCACGACGAGACCTACTGCGACCCCGCCAGCCT

GTTCCACGTGAGCAACGACTACAGCTTCATCAGATACTACACCAGAACCCTGTACCA

GTTCCAGTTCCAGGAGGCCCTGTGCCAGGCCGCCAAGCACGAGGGCCCCCTGCACA

AGTGCGACATCAGCAACAGCACCGAGGCCGGCCAGAAGCTGTTCAACATGCTGAGA

CTGGGCAAGAGCGAGCCCTGGACCCTGGCCCTGGAGAACGTGGTGGGCGCCAAGAA

CATGAACGTGAGACCCCTGCTGAACTACTTCGAGCCCCTGTTCACCTGGCTGAAGGA

CCAGAACAAGAACAGCTTCGTGGGCTGGAGCACCGACTGGAGCCCCTACGCCGACC

AGAGCATCAAGGTGAGAATCAGCCTGAAGAGCGCCCTGGGCGACAAGGCCTACGA

GTGGAACGACAACGAGATGTACCTGTTCAGAAGCAGCGTGGCCTACGCCATGAGAC

AGTACTTCCTGAAGGTGAAGAACCAGATGATCCTGTTCGGCGAGGAGGACGTGAGA

GTGGCCAACCTGAAGCCCAGAATCAGCTTCAACTTCTTCGTGACCGCCCCCAAGAAC

GTGAGCGACATCATCCCCAGAACCGAGGTGGAGAAGGCCATCAGAATGAGCAGAA

GCAGAATCAACGACGCCTTCAGACTGAACGACAACAGCCTGGAGTTCCTGGGCATC

CAGCCCACCCTGGGCCCCCCCAACCAGCCCCCCGTGAGCGACAAGACCCACACCTG

CCCCCCCTGCCCCGCCCCCGAGCTGCTGGGCGGCCCCAGCGTGTTCCTGTTCCCCCC

CAAGCCCAAGGACACCCTGATGATCAGCAGAACCCCCGAGGTGACCTGCGTGGTGG

TGGACGTGAGCCACGAGGACCCCGAGGTGAAGTTCAACTGGTACGTGGACGGCGTG

GAGGTGCACAACGCCAAGACCAAGCCCAGAGAGGAGCAGTACAACAGCACCTACA

GAGTGGTGAGCGTGCTGACCGTGCTGCACCAGGACTGGCTGAACGGCAAGGAGTAC

AAGTGCAAGGTGAGCAACAAGGCCCTGCCCGCCCCCATCGAGAAGACCATCAGCAA

GGCCAAGGGCCAGCCCAGAGAGCCCCAGGTGTACACCCTGCCCCCCAGCAGAGACG

AGCTGACCAAGAACCAGGTGAGCCTGACCTGCCTGGTGAAGGGCTTCTACCCCAGC

GACATCGCCGTGGAGTGGGAGAGCAACGGCCAGCCCGAGAACAACTACAAGACCA

CCCCCCCCGTGCTGGACAGCGACGGCAGCTTCTTCCTGTACAGCAAGCTGACCGTGG

ACAAGAGCAGATGGCAGCAGGGCAACGTGTTCAGCTGCAGCGTGATGCACGAGGCC

CTGCACAACCACTACACCCAGAAGAGCCTGAGCCTGAGCCCCGGCTGA

AMI121

CAGAGCACCATCGAGGAGCAGGCCAAGACCTTCCTGGACAAGTTCAACCACGAGGC SEQ ID NO: 73

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCagcGCCCAGATGTACCCCCTGCAGGAGATCCAGAACCTGACC

GTGAAGCTGCAGCTGCAGGCCCTGCAGCAGAACGGCAGCAGCGTGCTGAGCGAGGA

CAAGAGCAAGAGACTGAACACCATCCTGAACACCATGAGCACCATCTACAGCACCG

GCAAGGTGTGCAACCCCGACAACCCCCAGGAGTGCCTGCTGCTGGAGCCCGGCCTG

AACGAGATCATGGCCAACAGCCTGGACTACAACGAGAGACTGTGGGCCTGGGAGAG

CTGGAGAAGCGAGGTGGGCAAGCAGCTGAGACCCCTGTACGAGGAGTACGTGGTGC

```
TGAAGAACGAGATGGCCAGAGCCAACCACTACGAGGACTACGGCGACTACTGGAG
AGGCGACTACGAGGTGAACGGCGTGGACGGCTACGACTACAGCAGAGGCCAGCTG
ATCGAGGACGTGGAGCACACCTTCGAGGAGATCAAGCCCCTGTACGAGCACCTGCA
CGCCTACGTGAGAGCCAAGCTGATGAACGCCTACCCCAGCTACATCAGCCCCATCG
GCTGCCTGCCCGCCCACCTGCTGGGCGACATGTGGGGCAGATTCTGGACCAACCTGT
ACAGCCTGACCGTGCCCTTCGGCCAGAAGCCCAACATCGACGTGACCGACGCCATG
GTGGACCAGGCCTGGGACGCCCAGAGAATCTTCAAGGAGGCCGAGAAGTTCTTCGT
GAGCGTGGGCCTGCCCAACATGACCCAGGGCTTCTGGGAGctgAGCATGCTGACCGA
CCCCGGCAACGTGCAGAAGGCCGTGTGCCACCCCACCGCCTGGGACCTGGGCAAGG
GCGACTTCAGAATCCTGATGTGCACCAAGGTGACCATGGACGACTTCCTGACCGCCC
ACgcCGAGATGGGCagaATCCAGTACGACATGGCCTACgtgGCCCAGCCCTTCCTGCTG
AGAAACGGCGCCAACGAGGGCTTCCACcAGGCCGTGGGCGAGATCATGAGCCTGAG
CGCCGCCACCCCCAAGCACCTGAAGAGCATCGGCCTGCTGAGCCCCGACTTCCAGG
AGGACAACGAGACCGAGATCAACTTCCTGCTGAAGCAGGCCCTGACCATCGTGGGC
ACCCTGCCCTTCACCTACATGCTGGAGAAGTGGAGATGGATGGTGTTCAAGGGCGA
GATCCCCAAGGACCAGTGGATGAAGAAGTGGTGGGAGATGAAGAGAGAGATCGTG
GGCGTGGTGGAGCCCGTGCCCCACGACGAGACCTACTGCGACCCCGCCAGCCTGTT
CCACGTGAGCAACGACTACAGCTTCATCAGATACTACACCAGAACCCTGTACCAGTT
CCAGTTCCAGGAGGCCCTGTGCCAGGCCGCCAAGCACGAGGGCCCCCTGCACAAGT
GCGACATCAGCAACAGCACCGAGGCCGGCCAGAAGCTGTTCAACATGCTGAGACTG
GGCAAGAGCGAGCCCTGGACCCTGGCCCTGGAGAACGTGGTGGGCGCCAAGAACAT
GAACGTGAGACCCCTGCTGAACTACTTCGAGCCCCTGTTCACCTGGCTGAAGGACCA
GAACAAGAACAGCTTCGTGGGCTGGAGCACCGACTGGAGCCCCTACGCCGACCAGA
GCATCAAGGTGAGAATCAGCCTGAAGAGCGCCCTGGGCGACAAGGCCTACGAGTGG
AACGACAACGAGATGTACCTGTTCAGAAGCAGCGTGGCCTACGCCATGAGACAGTA
CTTCCTGAAGGTGAAGAACCAGATGATCCTGTTCGGCGAGGAGGACGTGAGAGTGG
CCAACCTGAAGCCCAGAATCAGCTTCAACTTCTTCGTGACCGCCCCCAAGAACGTGA
GCGACATCATCCCCAGAACCGAGGTGGAGAAGGCCATCAGAATGAGCAGAAGCAG
AATCAACGACGCCTTCAGACTGAACGACAACAGCCTGGAGTTCCTGGGCATCCAGC
CCACCCTGGGCCCCCCCAACCAGCCCCCCGTGAGCGACAAGACCCACACCTGCCCC
CCCTGCCCCGCCCCCGAGCTGCTGGGCGGCCCCAGCGTGTTCCTGTTCCCCCCCAAG
CCCAAGGACACCCTGATGATCAGCAGAACCCCCGAGGTGACCTGCGTGGTGGTGGA
CGTGAGCCACGAGGACCCCGAGGTGAAGTTCAACTGGTACGTGGACGGCGTGGAGG
TGCACAACGCCAAGACCAAGCCCAGAGAGGAGCAGTACAACAGCACCTACAGAGT
GGTGAGCGTGCTGACCGTGCTGCACCAGGACTGGCTGAACGGCAAGGAGTACAAGT
GCAAGGTGAGCAACAAGGCCCTGCCCGCCCCCATCGAGAAGACCATCAGCAAGGCC
AAGGGCCAGCCCAGAGAGCCCCAGGTGTACACCCTGCCCCCCAGCAGAGACGAGCT
GACCAAGAACCAGGTGAGCCTGACCTGCCTGGTGAAGGGCTTCTACCCCAGCGACA
TCGCCGTGGAGTGGGAGAGCAACGGCCAGCCCGAGAACAACTACAAGACCACCCCC
CCCGTGCTGGACAGCGACGGCAGCTTCTTCCTGTACAGCAAGCTGACCGTGGACAA
```

-continued

GAGCAGATGGCAGCAGGGCAACGTGTTCAGCTGCAGCGTGATGCACGAGGCCCTGC

ACAACCACTACACCCAGAAGAGCCTGAGCCTGAGCCCCGGCTGA

AMI122 SEQ ID NO: 74

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGctgAGCATGCTGACCGA

CCCCGGCAACGTGCAGAAGGCCGTGTGCCACCCCACCGCCTGGGACCTGGGCAAGG

GCGACTTCAGAATCCTGATGTGCACCAAGGTGACCATGGACGACTTCCTGACCGCCC

ACgcCGAGATGGGCagaATCCAGTACGACATGGCCTACgtgGCCCAGCCCTTCCTGCTG

AGAAACGGCGCCAACGAGGGCTTCCACcAGGCCGTGGGCGAGATCATGAGCCTGAG

CGCCGCCACCCCCAAGCACCTGAAGAGCATCGGCCTGCTGAGCCCCGACTTCCAGG

AGGACAACGAGACCGAGATCAACTTCCTGCTGAAGCAGGCCCTGACCATCGTGGGC

ACCCTGCCCTTCACCTACATGCTGGAGAAGTGGAGATGGATGGTGTTCAAGGGCGA

GATCCCCAAGGACCAGTGGATGAAGAAGTGGTGGGAGATGAAGAGAGATCGTG

GGCGTGGTGGAGCCCGTGCCCCACGACGAGACCTACTGCGACCCCGCCAGCCTGTT

CCACGTGAGCAACGACTACAGCTTCATCAGATACTACACCAGAACCCTGTACCAGTT

CCAGTTCCAGGAGGCCCTGTGCCAGGCCGCCAAGCACGAGGGCCCCCTGCACAAGT

GCGACATCAGCAACAGCACCGAGGCCGGCCAGAAGCTGTTCAACATGCTGAGACTG

GGCAAGAGCGAGCCCTGGACCCTGGCCCTGGAGAACGTGGTGGGCGCCAAGAACAT

GAACGTGAGACCCCTGCTGAACTACTTCGAGCCCCTGTTCACCTGGCTGAAGGACCA

GAACAAGAACAGCTTCGTGGGCTGGAGCACCGACTGGAGCCCCTACGCCGACCAGA

GCATCAAGGTGAGAATCAGCCTGAAGAGCGCCCTGGGCGACAAGGCCTACGAGTGG

AACGACAACGAGATGTACCTGTTCAGAAGCAGCGTGGCCTACGCCATGAGACAGTA

CTTCCTGAAGGTGAAGAACCAGATGATCCTGTTCGGCGAGGAGGACGTGAGAGTGG

CCAACCTGAAGCCCAGAATCAGCTTCAACTTCTTCGTGACCGCCCCCAAGAACGTGA

GCGACATCATCCCCAGAACCGAGGTGGAGAAGGCCATCAGAATGAGCAGAAGCAG

AATCAACGACGCCTTCAGACTGAACGACAACAGCCTGGAGTTCCTGGGCATCCAGC

```
CCACCCTGGGCCCCCCAACCAGCCCCCCGTGAGCGACAAGACCCACACCTGCCCC

CCCTGCCCCGCCCCCGAGCTGCTGGGCGGCCCCAGCGTGTTCCTGTTCCCCCCCAAG

CCCAAGGACACCCTGATGATCAGCAGAACCCCCGAGGTGACCTGCGTGGTGGTGGA

CGTGAGCCACGAGGACCCCGAGGTGAAGTTCAACTGGTACGTGGACGGCGTGGAGG

TGCACAACGCCAAGACCAAGCCCAGAGAGGAGCAGTACAACAGCACCTACAGAGT

GGTGAGCGTGCTGACCGTGCTGCACCAGGACTGGCTGAACGGCAAGGAGTACAAGT

GCAAGGTGAGCAACAAGGCCCTGCCCGCCCCCATCGAGAAGACCATCAGCAAGGCC

AAGGGCCAGCCCAGAGAGCCCCAGGTGTACACCCTGCCCCCCAGCAGAGACGAGCT

GACCAAGAACCAGGTGAGCCTGACCTGCCTGGTGAAGGGCTTCTACCCCAGCGACA

TCGCCGTGGAGTGGGAGAGCAACGGCCAGCCCGAGAACAACTACAAGACCACCCCC

CCCGTGCTGGACAGCGACGGCAGCTTCTTCCTGTACAGCAAGCTGACCGTGGACAA

GAGCAGATGGCAGCAGGGCAACGTGTTCAGCTGCAGCGTGATGCACGAGGCCCTGC

ACAACCACTACACCCAGAAGAGCCTGAGCCTGAGCCCCGGCTGA
```

AMI123                                                     SEQ ID NO: 75

```
CAGAGCACCATCGAGGAGCAGGCCAAGtaCTTCCTGGACAAGTTCAACCACGAGGCC

GAGGACCTGTTCTACCAGAGCAGCCTGGCCAGCTGGAACTACAACACCAACATCAC

CGAGGAGAACGTGCAGAACATGAACAACGCCGGCGACAAGTGGAGCGCCTTCCTGA

AGGAGCAGAGCACCagcGCCCAGATGTACCCCCTGCAGGAGATCCAGAACCTGACCG

TGAAGCTGCAGCTGCAGGCCCTGCAGCAGAACGGCAGCAGCGTGCTGAGCGAGGAC

AAGAGCAAGAGACTGAACACCATCCTGAACACCATGAGCACCATCTACAGCACCGG

CAAGGTGTGCAACCCCGACAACCCCCAGGAGTGCCTGCTGCTGGAGCCCGGCCTGA

ACGAGATCATGGCCAACAGCCTGGACTACAACGAGAGACTGTGGGCCTGGGAGAGC

TGGAGAAGCGAGGTGGGCAAGCAGCTGAGACCCCTGTACGAGGAGTACGTGGTGCT

GAAGAACGAGATGGCCAGAGCCAACCACTACGAGGACTACGGCGACTACTGGAGA

GGCGACTACGAGGTGAACGGCGTGGACGGCTACGACTACAGCAGAGGCCAGCTGAT

CGAGGACGTGGAGCACACCTTCGAGGAGATCAAGCCCCTGTACGAGCACCTGCACG

CCTACGTGAGAGCCAAGCTGATGAACGCCTACCCCAGCTACATCAGCCCCATCGGCT

GCCTGCCCGCCCACCTGCTGGGCGACATGTGGGGCAGATTCTGGACCAACCTGTACA

GCCTGACCGTGCCCTTCGGCCAGAAGCCCAACATCGACGTGACCGACGCCATGGTG

GACCAGGCCTGGGACGCCCAGAGAATCTTCAAGGAGGCCGAGAAGTTCTTCGTGAG

CGTGGGCCTGCCCAACATGACCCAGGGCTTCTGGGAGttCAGCATGCTGACCGACCCC

GGCAACGTGCAGAAGGCCGTGTGCCACCCCACCGCCTGGGACCTGGGCAAGGGCGA

CTTCAGAATCCTGATGTGCACCAAGGTGACCATGGACGACTTCCTGACCGCCCACgc

CGAGATGGGCCACATCCAGTACGACATGGCCTACGCCctgCAGCCCTTCCTGCTGAGA

AACGGCGCCAACGAGGGCTTCCACcAGGCCGTGGGCGAGATCATGAGCCTGAGCGC

CGCCACCCCCAAGCACCTGAAGAGCATCGGCCTGCTGAGCCCCGACTTCCAGGAGG

ACAACGAGACCGAGATCAACTTCCTGCTGAAGCAGGCCCTGACCATCGTGGGCACC

CTGCCCTTCACCTACATGCTGGAGAAGTGGAGATGGATGGTGTTCAAGGGCGAGAT

CCCCAAGGACCAGTGGATGAAGAAGTGGTGGGAGATGAAGAGAGAGATCGTGGGC

GTGGTGGAGCCCGTGCCCCACGACGAGACCTACTGCGACCCCGCCAGCCTGTTCCAC
```

-continued

GTGAGCAACGACTACAGCTTCATCAGATACTACACCAGAACCCTGTACCAGTTCCAG
TTCCAGGAGGCCCTGTGCCAGGCCGCCAAGCACGAGGGCCCCCTGCACAAGTGCGA
CATCAGCAACAGCACCGAGGCCGGCCAGAAGCTGTTCAACATGCTGAGACTGGGCA
AGAGCGAGCCCTGGACCCTGGCCCTGGAGAACGTGGTGGGCGCCAAGAACATGAAC
GTGAGACCCCTGCTGAACTACTTCGAGCCCCTGTTCACCTGGCTGAAGGACCAGAAC
AAGAACAGCTTCGTGGGCTGGAGCACCGACTGGAGCCCCTACGCCGACCAGAGCAT
CAAGGTGAGAATCAGCCTGAAGAGCGCCCTGGGCGACAAGGCCTACGAGTGGAAC
GACAACGAGATGTACCTGTTCAGAAGCAGCGTGGCCTACGCCATGAGACAGTACTT
CCTGAAGGTGAAGAACCAGATGATCCTGTTCGGCGAGGAGGACGTGAGAGTGGCCA
ACCTGAAGCCCAGAATCAGCTTCAACTTCTTCGTGACCGCCCCCAAGAACGTGAGCG
ACATCATCCCCAGAACCGAGGTGGAGAAGGCCATCAGAATGAGCAGAAGCAGAAT
CAACGACGCCTTCAGACTGAACGACAACAGCCTGGAGTTCCTGGGCATCCAGCCCA
CCCTGGGCCCCCCCAACCAGCCCCCCGTGAGCGACAAGACCCACACCTGCCCCCCT
GCCCCGCCCCCGAGCTGCTGGGCGGCCCCAGCGTGTTCCTGTTCCCCCCCAAGCCCA
AGGACACCCTGATGATCAGCAGAACCCCCGAGGTGACCTGCGTGGTGGTGGACGTG
AGCCACGAGGACCCCGAGGTGAAGTTCAACTGGTACGTGGACGGCGTGGAGGTGCA
CAACGCCAAGACCAAGCCCAGAGAGGAGCAGTACAACAGCACCTACAGAGTGGTG
AGCGTGCTGACCGTGCTGCACCAGGACTGGCTGAACGGCAAGGAGTACAAGTGCAA
GGTGAGCAACAAGGCCCTGCCCGCCCCCATCGAGAAGACCATCAGCAAGGCCAAGG
GCCAGCCCAGAGAGCCCCAGGTGTACACCCTGCCCCCCAGCAGAGACGAGCTGACC
AAGAACCAGGTGAGCCTGACCTGCCTGGTGAAGGGCTTCTACCCCAGCGACATCGC
CGTGGAGTGGGAGAGCAACGGCCAGCCCGAGAACAACTACAAGACCACCCCCCCCG
TGCTGGACAGCGACGGCAGCTTCTTCCTGTACAGCAAGCTGACCGTGGACAAGAGC
AGATGGCAGCAGGGCAACGTGTTCAGCTGCAGCGTGATGCACGAGGCCCTGCACAA
CCACTACACCCAGAAGAGCCTGAGCCTGAGCCCCGGCTGA

AMI124

SEQ ID NO: 76

CAGAGCACCATCGAGGAGCAGGCCAAGtaCTTCCTGGACAAGTTCAACCACGAGGCC
GAGGACCTGTTCTACCAGAGCAGCCTGGCCAGCTGGAACTACAACACCAACATCAC
CGAGGAGAACGTGCAGAACATGAACAACGCCGGCGACAAGTGGAGCGCCTTCCTGA
AGGAGCAGAGCACCagcGCCCAGATGTACCCCCTGCAGGAGATCCAGAACCTGACCG
TGAAGCTGCAGCTGCAGGCCCTGCAGCAGAACGGCAGCAGCGTGCTGAGCGAGGAC
AAGAGCAAGAGACTGAACACCATCCTGAACACCATGAGCACCATCTACAGCACCGG
CAAGGTGTGCAACCCCGACAACCCCCAGGAGTGCCTGCTGCTGGAGCCCGGCCTGA
ACGAGATCATGGCCAACAGCCTGGACTACAACGAGAGACTGTGGGCCTGGGAGAGC
TGGAGAAGCGAGGTGGGCAAGCAGCTGAGACCCCTGTACGAGGAGTACGTGGTGCT
GAAGAACGAGATGGCCAGAGCCAACCACTACGAGGACTACGGCGACTACTGGAGA
GGCGACTACGAGGTGAACGGCGTGGACGGCTACGACTACAGCAGAGGCCAGCTGAT
CGAGGACGTGGAGCACACCTTCGAGGAGATCAAGCCCCTGTACGAGCACCTGCACG
CCTACGTGAGAGCCAAGCTGATGAACGCCTACCCCAGCTACATCAGCCCCATCGGCT
GCCTGCCCGCCCACCTGCTGGGCGACATGTGGGGCAGATTCTGGACCAACCTGTACA
GCCTGACCGTGCCCTTCGGCCAGAAGCCCAACATCGACGTGACCGACGCCATGGTG -continued

```
GACCAGGCCTGGGACGCCCAGAGAATCTTCAAGGAGGCCGAGAAGTTCTTCGTGAG
CGTGGGCCTGCCCAACATGACCCAGGGCTTCTGGGAGttCAGCATGCTGACCGACCCC
GGCAACGTGCAGAAGGCCGTGTGCCACCCCACCGCCTGGGACCTGGGCAAGGGCGA
CTTCAGAATCCTGATGTGCACCAAGGTGACCATGGACGACTTCCTGACCGCCCACgc
CGAGATGGGCagaATCCAGTACGACATGGCCTACGCCctgCAGCCCTTCCTGCTGAGAA
ACGGCGCCAACGAGGGCTTCCACcAGGCCGTGGGCGAGATCATGAGCCTGAGCGCC
GCCACCCCCAAGCACCTGAAGAGCATCGGCCTGCTGAGCCCCGACTTCCAGGAGGA
CAACGAGACCGAGATCAACTTCCTGCTGAAGCAGGCCCTGACCATCGTGGGCACCC
TGCCCTTCACCTACATGCTGGAGAAGTGGAGATGGATGGTGTTCAAGGGCGAGATC
CCCAAGGACCAGTGGATGAAGAAGTGGTGGGAGATGAAGAGAGATCGTGGGCG
TGGTGGAGCCCGTGCCCCACGACGAGACCTACTGCGACCCCGCCAGCCTGTTCCACG
TGAGCAACGACTACAGCTTCATCAGATACTACACCAGAACCCTGTACCAGTTCCAGT
TCCAGGAGGCCCTGTGCCAGGCCGCCAAGCACGAGGGCCCCCTGCACAAGTGCGAC
ATCAGCAACAGCACCGAGGCCGGCCAGAAGCTGTTCAACATGCTGAGACTGGGCAA
GAGCGAGCCCTGGACCCTGGCCCTGGAGAACGTGGTGGGCGCCAAGAACATGAACG
TGAGACCCCTGCTGAACTACTTCGAGCCCCTGTTCACCTGGCTGAAGGACCAGAACA
AGAACAGCTTCGTGGGCTGGAGCACCGACTGGAGCCCCTACGCCGACCAGAGCATC
AAGGTGAGAATCAGCCTGAAGAGCGCCCTGGGCGACAAGGCCTACGAGTGGAACG
ACAACGAGATGTACCTGTTCAGAAGCAGCGTGGCCTACGCCATGAGACAGTACTTC
CTGAAGGTGAAGAACCAGATGATCCTGTTCGGCGAGGAGGACGTGAGAGTGGCCAA
CCTGAAGCCCAGAATCAGCTTCAACTTCTTCGTGACCGCCCCCAAGAACGTGAGCGA
CATCATCCCCAGAACCGAGGTGGAGAAGGCCATCAGAATGAGCAGAAGCAGAATC
AACGACGCCTTCAGACTGAACGACAACAGCCTGGAGTTCCTGGGCATCCAGCCCAC
CCTGGGCCCCCCCAACCAGCCCCCCGTGAGCGACAAGACCCACACCTGCCCCCCCTG
CCCCGCCCCCGAGCTGCTGGGCGGCCCCAGCGTGTTCCTGTTCCCCCCCAAGCCCAA
GGACACCCTGATGATCAGCAGAACCCCCGAGGTGACCTGCGTGGTGGTGGACGTGA
GCCACGAGGACCCCGAGGTGAAGTTCAACTGGTACGTGGACGGCGTGGAGGTGCAC
AACGCCAAGACCAAGCCCAGAGAGGAGCAGTACAACAGCACCTACAGAGTGGTGA
GCGTGCTGACCGTGCTGCACCAGGACTGGCTGAACGGCAAGGAGTACAAGTGCAAG
GTGAGCAACAAGGCCCTGCCCGCCCCCATCGAGAAGACCATCAGCAAGGCCAAGGG
CCAGCCCAGAGAGCCCCAGGTGTACACCCTGCCCCCCAGCAGAGACGAGCTGACCA
AGAACCAGGTGAGCCTGACCTGCCTGGTGAAGGGCTTCTACCCCAGCGACATCGCC
GTGGAGTGGGAGAGCAACGGCCAGCCCGAGAACAACTACAAGACCACCCCCCCCGT
GCTGGACAGCGACGGCAGCTTCTTCCTGTACAGCAAGCTGACCGTGGACAAGAGCA
GATGGCAGCAGGGCAACGTGTTCAGCTGCAGCGTGATGCACGAGGCCCTGCACAAC
CACTACACCCAGAAGAGCCTGAGCCTGAGCCCCGGCTGA
```

AMI125

SEQ ID NO: 77

```
CAGAGCACCATCGAGGAGCAGGCCAAGACCTTCCTGGACAAGTTCAACCACGAGGC
CGAGGACCTGTTCTACCAGAGCAGCCTGGCCAGCTGGAACTACAACACCAACATCA
CCGAGGAGAACGTGCAGAACATGAACAACGCCGGCGACAAGTGGAGCGCCTTCCTG
```

-continued

```
AAGGAGCAGAGCACCCTGGCCCAGATGTACCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCGAGATGGGCgccATCCAGTACGACATGGCCTACGCCctgCAGCCCTTCCTGCT

GAGAAACGGCGCCAACGAGGGCTTCCACcAGGCCGTGGGCGAGATCATGAGCCTGA

GCGCCGCCACCCCCAAGCACCTGAAGAGCATCGGCCTGCTGAGCCCCGACTTCCAG

GAGGACAACGAGACCGAGATCAACTTCCTGCTGAAGCAGGCCCTGACCATCGTGGG

CACCCTGCCCTTCACCTACATGCTGGAGAAGTGGAGATGGATGGTGTTCAAGGGCG

AGATCCCCAAGGACCAGTGGATGAAGAAGTGGTGGGAGATGAAGAGAGAGATCGT

GGGCGTGGTGGAGCCCGTGCCCCACGACGAGACCTACTGCGACCCCGCCAGCCTGT

TCCACGTGAGCAACGACTACAGCTTCATCAGATACTACACCAGAACCCTGTACCAGT

TCCAGTTCCAGGAGGCCCTGTGCCAGGCCGCCAAGCACGAGGGCCCCCTGCACAAG

TGCGACATCAGCAACAGCACCGAGGCCGGCCAGAAGCTGTTCAACATGCTGAGACT

GGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA
```

-continued

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI126                                                          SEQ ID NO: 78

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCGAGATGGGCagaATCCAGTACGACATGGCCTACGCCctgCAGCCCTTCCTGCT

GAGAAACGGCGCCAACGAGGGCTTCCACcAGGCCGTGGGCGAGATCATGAGCCTGA

GCGCCGCCACCCCCAAGCACCTGAAGAGCATCGGCCTGCTGAGCCCCGACTTCCAG

GAGGACAACGAGACCGAGATCAACTTCCTGCTGAAGCAGGCCCTGACCATCGTGGG

CACCCTGCCCTTCACCTACATGCTGGAGAAGTGGAGATGGATGGTGTTCAAGGGCG

AGATCCCCAAGGACCAGTGGATGAAGAAGTGGTGGGAGATGAAGAGAGAGATCGT

GGGCGTGGTGGAGCCCGTGCCCCACGACGAGACCTACTGCGACCCCGCCAGCCTGT

TCCACGTGAGCAACGACTACAGCTTCATCAGATACTACACCAGAACCCTGTACCAGT

TCCAGTTCCAGGAGGCCCTGTGCCAGGCCGCCAAGCACGAGGGCCCCCTGCACAAG

TGCGACATCAGCAACAGCACCGAGGCCGGCCAGAAGCTGTTCAACATGCTGAGACT

GGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

-continued

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI127

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACctgGAGATGGGCCACATCCAGTACGACATGGCCTACGCCctgCAGCCCTTCCTGCT

GAGAAACGGCGCCAACGAGGGCTTCCACcAGGCCGTGGGCGAGATCATGAGCCTGA

SEQ ID NO: 79

-continued

GCGCCGCCACCCCCAAGCACCTGAAGAGCATCGGCCTGCTGAGCCCCGACTTCCAG

GAGGACAACGAGACCGAGATCAACTTCCTGCTGAAGCAGGCCCTGACCATCGTGGG

CACCCTGCCCTTCACCTACATGCTGGAGAAGTGGAGATGGATGGTGTTCAAGGGCG

AGATCCCCAAGGACCAGTGGATGAAGAAGTGGTGGGAGATGAAGAGAGAGATCGT

GGGCGTGGTGGAGCCCGTGCCCCACGACGAGACCTACTGCGACCCCGCCAGCCTGT

TCCACGTGAGCAACGACTACAGCTTCATCAGATACTACACCAGAACCCTGTACCAGT

TCCAGTTCCAGGAGGCCCTGTGCCAGGCCGCCAAGCACGAGGGCCCCCTGCACAAG

TGCGACATCAGCAACAGCACCGAGGCCGGCCAGAAGCTGTTCAACATGCTGAGACT

GGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI128

CAGAGCACCATCGAGGAGCAGGCCagaACCTTCCTGGACAAGTTCAACCACGAGGCC          SEQ ID NO: 80

GAGGACCTGTTCTACCAGAGCAGCCTGGCCAGCTGGAACTACAACACCAACATCAC

CGAGGAGAACGTGCAGAACATGAACAACGCCGGCGACAAGTGGAGCGCCTTCCTGA

AGGAGCAGAGCACCCTGGCCCAGATGTACCCCCTGCAGGAGATCCAGAACCTGACC

GTGAAGCTGCAGCTGCAGGCCCTGCAGCAGAACGGCAGCAGCGTGCTGAGCGAGGA

CAAGAGCAAGAGACTGAACACCATCCTGAACACCATGAGCACCATCTACAGCACCG

GCAAGGTGTGCAACCCCGACAACCCCCAGGAGTGCCTGCTGCTGGAGCCCGGCCTG

AACGAGATCATGGCCAACAGCCTGGACTACAACGAGAGACTGTGGGCCTGGGAGAG

CTGGAGAAGCGAGGTGGGCAAGCAGCTGAGACCCCTGTACGAGGAGTACGTGGTGC

-continued

```
TGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACgcCGAGATGGGCCACATCCAGTACGACATGGCCTACGCCctgCAGCCCTTCCTGCT

GAGAAACGGCGCCAACGAGGGCTTCCACcAGGCCGTGGGCGAGATCATGAGCCTGA

GCGCCGCCACCCCCAAGCACCTGAAGAGCATCGGCCTGCTGAGCCCCGACTTCCAG

GAGGACAACGAGACCGAGATCAACTTCCTGCTGAAGCAGGCCCTGACCATCGTGGG

CACCCTGCCCTTCACCTACATGCTGGAGAAGTGGAGATGGATGGTGTTCAAGGGCG

AGATCCCCAAGGACCAGTGGATGAAGAAGTGGTGGGAGATGAAGAGAGAGATCGT

GGGCGTGGTGGAGCCCGTGCCCCACGACGAGACCTACTGCGACCCCGCCAGCCTGT

TCCACGTGAGCAACGACTACAGCTTCATCAGATACTACACCAGAACCCTGTACCAGT

TCCAGTTCCAGGAGGCCCTGTGCCAGGCCGCCAAGCACGAGGGCCCCCTGCACAAG

TGCGACATCAGCAACAGCACCGAGGCCGGCCAGAAGCTGTTCAACATGCTGAGACT

GGGCAAGAGCGAGCCCTGGACCCTGGCCCTGGAGAACGTGGTGGGCGCCAAGAAC

ATGAACGTGAGACCCCTGCTGAACTACTTCGAGCCCCTGTTCACCTGGCTGAAGGAC

CAGAACAAGAACAGCTTCGTGGGCTGGAGCACCGACTGGAGCCCCTACGCCGACCA

GAGCATCAAGGTGAGAATCAGCCTGAAGAGCGCCCTGGGCGACAAGGCCTACGAGT

GGAACGACAACGAGATGTACCTGTTCAGAAGCAGCGTGGCCTACGCCATGAGACAG

TACTTCCTGAAGGTGAAGAACCAGATGATCCTGTTCGGCGAGGAGGACGTGAGAGT

GGCCAACCTGAAGCCCAGAATCAGCTTCAACTTCTTCGTGACCGCCCCCAAGAACGT

GAGCGACATCATCCCCAGAACCGAGGTGGAGAAGGCCATCAGAATGAGCAGAAGC

AGAATCAACGACGCCTTCAGACTGAACGACAACAGCCTGGAGTTCCTGGGCATCCA

GCCCACCCTGGGCCCCCCCAACCAGCCCCCCGTGAGCGACAAGACCCACACCTGCC

CCCCCTGCCCCGCCCCCGAGCTGCTGGGCGGCCCCAGCGTGTTCCTGTTCCCCCCCA

AGCCCAAGGACACCCTGATGATCAGCAGAACCCCCGAGGTGACCTGCGTGGTGGTG

GACGTGAGCCACGAGGACCCCGAGGTGAAGTTCAACTGGTACGTGGACGGCGTGGA

GGTGCACAACGCCAAGACCAAGCCCAGAGAGGAGCAGTACAACAGCACCTACAGA

GTGGTGAGCGTGCTGACCGTGCTGCACCAGGACTGGCTGAACGGCAAGGAGTACAA

GTGCAAGGTGAGCAACAAGGCCCTGCCCGCCCCCATCGAGAAGACCATCAGCAAGG

CCAAGGGCCAGCCCAGAGAGCCCCAGGTGTACACCCTGCCCCCCAGCAGAGACGAG

CTGACCAAGAACCAGGTGAGCCTGACCTGCCTGGTGAAGGGCTTCTACCCCAGCGA

CATCGCCGTGGAGTGGGAGAGCAACGGCCAGCCCGAGAACAACTACAAGACCACCC

CCCCCGTGCTGGACAGCGACGGCAGCTTCTTCCTGTACAGCAAGCTGACCGTGGACA
```

AGAGCAGATGGCAGCAGGGCAACGTGTTCAGCTGCAGCGTGATGCACGAGGCCCTG

CACAACCACTACACCCAGAAGAGCCTGAGCCTGAGCCCCGGCTGA

AMI129                                                   SEQ ID NO: 81

CAGAGCACCATCGAGGAGCAGGCCAAGACCTTCCTGGACAAGTTCAACCACGAGGC

CGAGGACCTGTTCTACCAGAGCAGCCTGGCCAGCTGGAACTACAACACCAACATCA

CCGAGGAGAACGTGCAGAACATGAACAACGCCGGCGACAAGTGGAGCGCCTTCCTG

AAGGAGCAGAGCACCCTGGCCCAGATGTACCCCCTGCAGGAGATCCAGAACCTGAC

CGTGAAGCTGCAGCTGCAGGCCCTGCAGCAGAACGGCAGCAGCGTGCTGAGCGAGG

ACAAGAGCAAGAGACTGAACACCATCCTGAACACCATGAGCACCATCTACAGCACC

GGCAAGGTGTGCAACCCCGACAACCCCCAGGAGTGCCTGCTGCTGGAGCCCGGCCT

GAACGAGATCATGGCCAACAGCCTGGACTACAACGAGAGACTGTGGGCCTGGGAGA

GCTGGAGAAGCGAGGTGGGCAAGCAGCTGAGACCCCTGTACGAGGAGTACGTGGTG

CTGAAGAACGAGATGGCCAGAGCCAACCACTACGAGGACTACGGCGACTACTGGAG

AGGCGACTACGAGGTGAACGGCGTGGACGGCTACGACTACAGCAGAGGCCAGCTG

ATCGAGGACGTGGAGCACACCTTCGAGGAGATCAAGCCCCTGTACGAGCACCTGCA

CGCCTACGTGAGAGCCAAGCTGATGAACGCCTACCCCAGCTACATCAGCCCCATCG

GCTGCCTGCCCGCCCACCTGCTGGGCGACATGTGGGGCAGATTCTGGACCAACCTGT

ACAGCCTGACCGTGCCCTTCGGCCAGAAGCCCAACATCGACGTGACCGACGCCATG

GTGGACCAGGCCTGGGACGCCCAGAGAATCTTCAAGGAGGCCGAGAAGTTCTTCGT

GAGCGTGGGCCTGCCCAACATGACCCAGGGCTTCTGGGAGAACAGCATGCTGACCG

ACCCCGGCAACGTGCAGAAGGCCGTGTGCCACCCCACCGCCTGGGACCTGGGCAAG

GGCGACTTCAGAATCCTGATGTGCACCAAGGTGACCATGGACGACTTCCTGACCGCC

CACctgGAGATGGGCagaATCCAGTACGACATGGCCTACGCCctgCAGCCCTTCCTGCTG

AGAAACGGCGCCAACGAGGGCTTCCACcAGGCCGTGGGCGAGATCATGAGCCTGAG

CGCCGCCACCCCCAAGCACCTGAAGAGCATCGGCCTGCTGAGCCCCGACTTCCAGG

AGGACAACGAGACCGAGATCAACTTCCTGCTGAAGCAGGCCCTGACCATCGTGGGC

ACCCTGCCCTTCACCTACATGCTGGAGAAGTGGAGATGGATGGTGTTCAAGGGCGA

GATCCCCAAGGACCAGTGGATGAAGAAGTGGTGGGAGATGAAGAGAGAGATCGTG

GGCGTGGTGGAGCCCGTGCCCCACGACGAGACCTACTGCGACCCCGCCAGCCTGTT

CCACGTGAGCAACGACTACAGCTTCATCAGATACTACACCAGAACCCTGTACCAGTT

CCAGTTCCAGGAGGCCCTGTGCCAGGCCGCCAAGCACGAGGGCCCCCTGCACAAGT

GCGACATCAGCAACAGCACCGAGGCCGGCCAGAAGCTGTTCAACATGCTGAGACTG

GGCAAGAGCGAGCCCTGGACCCTGGCCCTGGAGAACGTGGTGGGCGCCAAGAACAT

GAACGTGAGACCCCTGCTGAACTACTTCGAGCCCCTGTTCACCTGGCTGAAGGACCA

GAACAAGAACAGCTTCGTGGGCTGGAGCACCGACTGGAGCCCCTACGCCGACCAGA

GCATCAAGGTGAGAATCAGCCTGAAGAGCGCCCTGGGCGACAAGGCCTACGAGTGG

AACGACAACGAGATGTACCTGTTCAGAAGCAGCGTGGCCTACGCCATGAGACAGTA

CTTCCTGAAGGTGAAGAACCAGATGATCCTGTTCGGCGAGGAGGACGTGAGAGTGG

CCAACCTGAAGCCCAGAATCAGCTTCAACTTCTTCGTGACCGCCCCCAAGAACGTGA

GCGACATCATCCCCAGAACCGAGGTGGAGAAGGCCATCAGAATGAGCAGAAGCAG

-continued

```
AATCAACGACGCCTTCAGACTGAACGACAACAGCCTGGAGTTCCTGGGCATCCAGC

CCACCCTGGGCCCCCCCAACCAGCCCCCCGTGAGCGACAAGACCCACACCTGCCCC

CCCTGCCCCGCCCCCGAGCTGCTGGGCGGCCCCAGCGTGTTCCTGTTCCCCCCCAAG

CCCAAGGACACCCTGATGATCAGCAGAACCCCCGAGGTGACCTGCGTGGTGGTGGA

CGTGAGCCACGAGGACCCCGAGGTGAAGTTCAACTGGTACGTGGACGGCGTGGAGG

TGCACAACGCCAAGACCAAGCCCAGAGAGGAGCAGTACAACAGCACCTACAGAGT

GGTGAGCGTGCTGACCGTGCTGCACCAGGACTGGCTGAACGGCAAGGAGTACAAGT

GCAAGGTGAGCAACAAGGCCCTGCCCGCCCCCATCGAGAAGACCATCAGCAAGGCC

AAGGGCCAGCCCAGAGAGCCCCAGGTGTACACCCTGCCCCCCAGCAGAGACGAGCT

GACCAAGAACCAGGTGAGCCTGACCTGCCTGGTGAAGGGCTTCTACCCCAGCGACA

TCGCCGTGGAGTGGGAGAGCAACGGCCAGCCCGAGAACAACTACAAGACCACCCCC

CCCGTGCTGGACAGCGACGGCAGCTTCTTCCTGTACAGCAAGCTGACCGTGGACAA

GAGCAGATGGCAGCAGGGCAACGTGTTCAGCTGCAGCGTGATGCACGAGGCCCTGC

ACAACCACTACACCCAGAAGAGCCTGAGCCTGAGCCCCGGCTGA
```

---

The invention claimed is:

1. An isolated angiotensin converting enzyme 2 (ACE2) polypeptide with one or more mutations relative to the wild-type ACE2 that cause the loss of ACE2 enzymatic activity comparing to the wild-type ACE2, the polypeptide comprising an amino acid sequence selected from the group consisting of SEQ ID NOs 3, 4, 10, 17, and 18.

2. A fusion protein comprising an isolated mutated ACE2 polypeptide of claim 1, further fused to a peptide at N or C terminal of the mutated ACE2 polypeptide, wherein the peptide is capable of binding to a receptor of an immune system associated cell.

3. The fusion protein of claim 2, wherein the peptide is a ligand binding to a Fc binding receptor (FcγR) on an immune cell of lymphocyte.

4. The fusion protein of claim 3, wherein the immune cell of lymphocyte is selected from group consisting of T cells, B cells, natural killer cells.

5. The fusion protein of claim 2, wherein the peptide is a Fc domain of human IgG antibodies (FcY).

\* \* \* \* \*

SEQUENCE LISTING

<160> NUMBER OF SEQ ID NOS: 77

<210> SEQ ID NO 1
<211> LENGTH: 723
<212> TYPE: PRT
<213> ORGANISM: Homo sapiens

<400> SEQUENCE: 1

```
Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205
```

-continued

Val Glu His Thr Phe Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
                260                 265                 270

Asn Ile Asp Val Thr Asp Ala Met Val Asp Gln Ala Trp Asp Ala Gln
            275                 280                 285

Arg Ile Phe Lys Glu Ala Glu Lys Phe Phe Val Ser Val Gly Leu Pro
290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
                340                 345                 350

Leu Thr Ala His His Glu Met Gly His Ile Gln Tyr Asp Met Ala Tyr
                355                 360                 365

Ala Ala Gln Pro Phe Leu Leu Arg Asn Gly Ala Asn Glu Gly Phe His
            370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
                420                 425                 430

Leu Pro Phe Thr Tyr Met Leu Glu Lys Trp Arg Trp Met Val Phe Lys
            435                 440                 445

Gly Glu Ile Pro Lys Asp Gln Trp Met Lys Lys Trp Trp Glu Met Lys
            450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
                500                 505                 510

Cys Gln Ala Ala Lys His Glu Gly Pro Leu His Lys Cys Asp Ile Ser
            515                 520                 525

Asn Ser Thr Glu Ala Gly Gln Lys Leu Phe Asn Met Leu Arg Leu Gly
            530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
            595                 600                 605

Ser Ala Leu Gly Asp Lys Ala Tyr Glu Trp Asn Asp Asn Glu Met Tyr
610                 615                 620

-continued

```
Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
            645                 650                 655

Asn Leu Lys Pro Arg Ile Ser Phe Asn Phe Val Thr Ala Pro Lys
        660                 665                 670

Asn Val Ser Asp Ile Ile Pro Arg Thr Glu Val Glu Lys Ala Ile Arg
            675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser
```

<210> SEQ ID NO 2
<211> LENGTH: 50
<212> TYPE: PRT
<213> ORGANISM: Homo sapiens

<400> SEQUENCE: 2

```
Cys Thr Lys Val Thr Met Asp Asp Phe Leu Thr Ala His His Glu Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50
```

<210> SEQ ID NO 3
<211> LENGTH: 50
<212> TYPE: PRT
<213> ORGANISM: Artificial Sequence
<220> FEATURE:
<223> OTHER INFORMATION: Synthetic

<400> SEQUENCE: 3

```
Cys Thr Lys Val Thr Met Asp Asp Phe Leu Thr Ala His His Glu Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50
```

<210> SEQ ID NO 4
<211> LENGTH: 50
<212> TYPE: PRT
<213> ORGANISM: Artificial Sequence
<220> FEATURE:
<223> OTHER INFORMATION: Synthetic

<400> SEQUENCE: 4

```
Cys Thr Lys Val Thr Met Asp Asp Phe Leu Thr Ala His Ala Glu Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
```

35                  40                  45

Ser Leu
    50

<210> SEQ ID NO 5
<211> LENGTH: 50
<212> TYPE: PRT
<213> ORGANISM: Artificial Sequence
<220> FEATURE:
<223> OTHER INFORMATION: Synthetic

<400> SEQUENCE: 5

Cys Thr Lys Val Thr Met Asp Asp Phe Leu Thr Ala His His Glu Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 6
<211> LENGTH: 50
<212> TYPE: PRT
<213> ORGANISM: Artificial Sequence
<220> FEATURE:
<223> OTHER INFORMATION: Synthetic

<400> SEQUENCE: 6

Cys Thr Lys Val Thr Met Asp Asp Phe Leu Thr Ala His Ala Glu Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50

<210> SEQ ID NO 7
<211> LENGTH: 50
<212> TYPE: PRT
<213> ORGANISM: Artificial Sequence
<220> FEATURE:
<223> OTHER INFORMATION: Synthetic

<400> SEQUENCE: 7

Cys Thr Lys Val Thr Met Asp Asp Phe Leu Thr Ala His His Glu Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50

<210> SEQ ID NO 8
<211> LENGTH: 50
<212> TYPE: PRT
<213> ORGANISM: Artificial Sequence
<220> FEATURE:
<223> OTHER INFORMATION: Synthetic

```
<400> SEQUENCE: 8

Cys Thr Lys Val Thr Met Asp Asp Phe Leu Thr Ala His Ala Glu Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50

<210> SEQ ID NO 9
<211> LENGTH: 50
<212> TYPE: PRT
<213> ORGANISM: Artificial Sequence
<220> FEATURE:
<223> OTHER INFORMATION: Synthetic

<400> SEQUENCE: 9

Cys Thr Lys Val Thr Met Asp Asp Phe Leu Thr Ala His His Gln Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 10
<211> LENGTH: 50
<212> TYPE: PRT
<213> ORGANISM: Artificial Sequence
<220> FEATURE:
<223> OTHER INFORMATION: Synthetic

<400> SEQUENCE: 10

Cys Thr Lys Val Thr Met Asp Asp Phe Leu Thr Ala His Ala Gln Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 11
<211> LENGTH: 50
<212> TYPE: PRT
<213> ORGANISM: Artificial Sequence
<220> FEATURE:
<223> OTHER INFORMATION: Synthetic

<400> SEQUENCE: 11

Cys Thr Lys Val Thr Met Asp Asp Phe Leu Thr Ala His His Gln Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50
```

<210> SEQ ID NO 12
<211> LENGTH: 50
<212> TYPE: PRT
<213> ORGANISM: Artificial Sequence
<220> FEATURE:
<223> OTHER INFORMATION: Synthetic

<400> SEQUENCE: 12

Cys Thr Lys Val Thr Met Asp Asp Phe Leu Thr Ala His Ala Gln Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 13
<211> LENGTH: 50
<212> TYPE: PRT
<213> ORGANISM: Artificial Sequence
<220> FEATURE:
<223> OTHER INFORMATION: Synthetic

<400> SEQUENCE: 13

Cys Thr Lys Val Thr Met Asp Asp Phe Leu Thr Ala His Ala Gln Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50

<210> SEQ ID NO 14
<211> LENGTH: 50
<212> TYPE: PRT
<213> ORGANISM: Artificial Sequence
<220> FEATURE:
<223> OTHER INFORMATION: Synthetic

<400> SEQUENCE: 14

Cys Thr Lys Val Thr Met Asp Asp Phe Leu Thr Ala His His Gln Met
1               5                   10                  15

Gly Ala Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
        35                  40                  45

Ser Leu
    50

<210> SEQ ID NO 15
<211> LENGTH: 50
<212> TYPE: PRT
<213> ORGANISM: Artificial Sequence
<220> FEATURE:
<223> OTHER INFORMATION: Synthetic

<400> SEQUENCE: 15

Cys Thr Lys Val Thr Met Asp Asp Phe Leu Thr Ala His Ala Gln Met
1               5                   10                  15

Gly Ala Ile Gln Tyr Asp Met Ala Tyr Ala Ala Gln Pro Phe Leu Leu
                20                  25                  30

Arg Asn Gly Ala Asn Glu Gly Phe His Glu Ala Val Gly Glu Ile Met
        35                  40                  45

Ser Leu
    50

<210> SEQ ID NO 16
<211> LENGTH: 50
<212> TYPE: PRT
<213> ORGANISM: Artificial Sequence
<220> FEATURE:
<223> OTHER INFORMATION: Synthetic

<400> SEQUENCE: 16

Cys Thr Lys Val Thr Met Asp Asp Phe Leu Thr Ala His His Glu Met
1               5                   10                  15

Gly His Ile Gln Tyr Asp Met Ala Tyr Ala Ala Gln Pro Phe Leu Leu
                20                  25                  30

Arg Asn Gly Ala Asn Glu Gly Phe His Glu Ala Val Gly Glu Ile Met
        35                  40                  45

Ser Leu
    50

<210> SEQ ID NO 17
<211> LENGTH: 106
<212> TYPE: PRT
<213> ORGANISM: Artificial Sequence
<220> FEATURE:
<223> OTHER INFORMATION: Synthetic

<400> SEQUENCE: 17

Cys Thr Lys Val Thr Met Asp Asp Phe Leu Thr Ala His His Glu Met
1               5                   10                  15

Gly His Ile Gln Tyr Asp Met Ala Tyr Ala Ala Gln Pro Phe Leu Leu
                20                  25                  30

Arg Asn Gly Ala Asn Glu Gly Phe His Gln Ala Val Gly Glu Ile Met
        35                  40                  45

Ser Leu Ser Ala Ala Thr Pro Lys His Leu Lys Ser Ile Gly Leu Leu
    50                  55                  60

Ser Pro Asp Phe Gln Glu Asp Asn Glu Thr Glu Ile Asn Phe Leu Leu
65                  70                  75                  80

Lys Gln Ala Leu Thr Ile Val Gly Thr Leu Pro Phe Thr Tyr Met Leu
                85                  90                  95

Glu Lys Trp Arg Trp Met Val Phe Lys Asp
            100                 105

<210> SEQ ID NO 18
<211> LENGTH: 50
<212> TYPE: PRT
<213> ORGANISM: Artificial Sequence
<220> FEATURE:
<223> OTHER INFORMATION: Synthetic

<400> SEQUENCE: 18

Cys Thr Lys Val Thr Met Asp Asp Phe Leu Thr Ala His His Gln Met
1               5                   10                  15

Gly His Ile Gln Tyr Asp Met Ala Tyr Ala Ala Gln Pro Phe Leu Leu
                20                  25                  30

-continued

Arg Asn Gly Ala Asn Glu Gly Phe His Gln Ala Val Gly Glu Ile Met
            35                  40                  45

Ser Leu
    50

<210> SEQ ID NO 19
<211> LENGTH: 50
<212> TYPE: PRT
<213> ORGANISM: Artificial Sequence
<220> FEATURE:
<223> OTHER INFORMATION: Synthetic

<400> SEQUENCE: 19

Cys Thr Lys Val Thr Met Asp Asp Phe Leu Thr Ala His Ala Gln Met
1               5                   10                  15

Gly His Ile Gln Tyr Asp Met Ala Tyr Ala Ala Gln Pro Phe Leu Leu
            20                  25                  30

Arg Asn Gly Ala Asn Glu Gly Phe His Glu Ala Val Gly Glu Ile Met
            35                  40                  45

Ser Leu
    50

<210> SEQ ID NO 20
<211> LENGTH: 50
<212> TYPE: PRT
<213> ORGANISM: Artificial Sequence
<220> FEATURE:
<223> OTHER INFORMATION: Synthetic

<400> SEQUENCE: 20

Cys Thr Lys Val Thr Met Asp Asp Phe Leu Thr Ala His Ala Glu Met
1               5                   10                  15

Gly Arg Ile Gln Tyr Asp Met Ala Tyr Val Ala Gln Pro Phe Leu Leu
            20                  25                  30

Arg Asn Gly Ala Asn Glu Gly Phe His Gln Ala Val Gly Glu Ile Met
            35                  40                  45

Ser Leu
    50

<210> SEQ ID NO 21
<211> LENGTH: 50
<212> TYPE: PRT
<213> ORGANISM: Artificial Sequence
<220> FEATURE:
<223> OTHER INFORMATION: Synthetic

<400> SEQUENCE: 21

Cys Thr Lys Val Thr Met Asp Asp Phe Leu Thr Ala His Ala Glu Met
1               5                   10                  15

Gly Arg Ile Gln Tyr Asp Met Ala Tyr Val Ala Gln Pro Phe Leu Leu
            20                  25                  30

Arg Asn Gly Ala Asn Glu Gly Phe His Gln Ala Val Gly Glu Ile Met
            35                  40                  45

Ser Leu
    50

<210> SEQ ID NO 22
<211> LENGTH: 50
<212> TYPE: PRT
<213> ORGANISM: Artificial Sequence
<220> FEATURE:
<223> OTHER INFORMATION: Synthetic

<400> SEQUENCE: 22

Cys Thr Lys Val Thr Met Asp Asp Phe Leu Thr Ala His Ala Glu Met
1               5                   10                  15

Gly His Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 23
<211> LENGTH: 50
<212> TYPE: PRT
<213> ORGANISM: Artificial Sequence
<220> FEATURE:
<223> OTHER INFORMATION: Synthetic

<400> SEQUENCE: 23

Cys Thr Lys Val Thr Met Asp Asp Phe Leu Thr Ala His Ala Glu Met
1               5                   10                  15

Gly Arg Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 24
<211> LENGTH: 50
<212> TYPE: PRT
<213> ORGANISM: Artificial Sequence
<220> FEATURE:
<223> OTHER INFORMATION: Synthetic

<400> SEQUENCE: 24

Cys Thr Lys Val Thr Met Asp Asp Phe Leu Thr Ala His Ala Glu Met
1               5                   10                  15

Gly Ala Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 25
<211> LENGTH: 50
<212> TYPE: PRT
<213> ORGANISM: Artificial Sequence
<220> FEATURE:
<223> OTHER INFORMATION: Synthetic

<400> SEQUENCE: 25

Cys Thr Lys Val Thr Met Asp Asp Phe Leu Thr Ala His Ala Glu Met
1               5                   10                  15

Gly Arg Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu

```
<210> SEQ ID NO 26
<211> LENGTH: 50
<212> TYPE: PRT
<213> ORGANISM: Artificial Sequence
<220> FEATURE:
<223> OTHER INFORMATION: Synthetic

<400> SEQUENCE: 26

Cys Thr Lys Val Thr Met Asp Asp Phe Leu Thr Ala His Leu Glu Met
1               5                   10                  15

Gly His Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 27
<211> LENGTH: 50
<212> TYPE: PRT
<213> ORGANISM: Artificial Sequence
<220> FEATURE:
<223> OTHER INFORMATION: Synthetic

<400> SEQUENCE: 27

Cys Thr Lys Val Thr Met Asp Asp Phe Leu Thr Ala His Ala Glu Met
1               5                   10                  15

Gly His Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 28
<211> LENGTH: 50
<212> TYPE: PRT
<213> ORGANISM: Artificial Sequence
<220> FEATURE:
<223> OTHER INFORMATION: Synthetic

<400> SEQUENCE: 28

Cys Thr Lys Val Thr Met Asp Asp Phe Leu Thr Ala His Leu Glu Met
1               5                   10                  15

Gly Arg Ile Gln Tyr Asp Met Ala Tyr Ala Leu Gln Pro Phe Leu Leu
            20                  25                  30

Arg Asn Gly Ala Asn Glu Gly Phe His Gln Ala Val Gly Glu Ile Met
        35                  40                  45

Ser Leu
    50

<210> SEQ ID NO 29
<211> LENGTH: 932
<212> TYPE: PRT
<213> ORGANISM: Homo sapiens

<400> SEQUENCE: 29

Gln Ser Thr Ile Glu Glu Gln Ala Lys Thr Phe Leu Asp Lys Phe Asn
1               5                   10                  15
```

His Glu Ala Glu Asp Leu Phe Tyr Gln Ser Ser Leu Ala Ser Trp Asn
            20                  25                  30
Tyr Asn Thr Asn Ile Thr Glu Glu Asn Val Gln Asn Met Asn Asn Ala
            35                  40                  45
Gly Asp Lys Trp Ser Ala Phe Leu Lys Glu Gln Ser Thr Leu Ala Gln
            50                  55                  60
Met Tyr Pro Leu Gln Glu Ile Gln Asn Leu Thr Val Lys Leu Gln Leu
65                  70                  75                  80
Gln Ala Leu Gln Gln Asn Gly Ser Ser Val Leu Ser Glu Asp Lys Ser
                85                  90                  95
Lys Arg Leu Asn Thr Ile Leu Asn Thr Met Ser Thr Ile Tyr Ser Thr
            100                 105                 110
Gly Lys Val Cys Asn Pro Asp Asn Pro Gln Glu Cys Leu Leu Leu Glu
            115                 120                 125
Pro Gly Leu Asn Glu Ile Met Ala Asn Ser Leu Asp Tyr Asn Glu Arg
            130                 135                 140
Leu Trp Ala Trp Glu Ser Trp Arg Ser Glu Val Gly Lys Gln Leu Arg
145                 150                 155                 160
Pro Leu Tyr Glu Glu Tyr Val Val Leu Lys Asn Glu Met Ala Arg Ala
                165                 170                 175
Asn His Tyr Glu Asp Tyr Gly Asp Tyr Trp Arg Gly Asp Tyr Glu Val
            180                 185                 190
Asn Gly Val Asp Gly Tyr Asp Tyr Ser Arg Gly Gln Leu Ile Glu Asp
            195                 200                 205
Val Glu His Thr Phe Glu Glu Ile Lys Pro Leu Tyr Glu His Leu His
            210                 215                 220
Ala Tyr Val Arg Ala Lys Leu Met Asn Ala Tyr Pro Ser Tyr Ile Ser
225                 230                 235                 240
Pro Ile Gly Cys Leu Pro Ala His Leu Leu Gly Asp Met Trp Gly Arg
                245                 250                 255
Phe Trp Thr Asn Leu Tyr Ser Leu Thr Val Pro Phe Gly Gln Lys Pro
            260                 265                 270
Asn Ile Asp Val Thr Asp Ala Met Val Asp Gln Ala Trp Asp Ala Gln
            275                 280                 285
Arg Ile Phe Lys Glu Ala Glu Lys Phe Phe Val Ser Val Gly Leu Pro
290                 295                 300
Asn Met Thr Gln Gly Phe Trp Glu Asn Ser Met Leu Thr Asp Pro Gly
305                 310                 315                 320
Asn Val Gln Lys Ala Val Cys His Pro Thr Ala Trp Asp Leu Gly Lys
                325                 330                 335
Gly Asp Phe Arg Ile Leu Met Cys Thr Lys Val Thr Met Asp Asp Phe
            340                 345                 350
Leu Thr Ala His His Glu Met Gly His Ile Gln Tyr Asp Met Ala Tyr
            355                 360                 365
Ala Ala Gln Pro Phe Leu Leu Arg Asn Gly Ala Asn Glu Gly Phe His
            370                 375                 380
Glu Ala Val Gly Glu Ile Met Ser Leu Ser Ala Ala Thr Pro Lys His
385                 390                 395                 400
Leu Lys Ser Ile Gly Leu Leu Ser Pro Asp Phe Gln Glu Asp Asn Glu
                405                 410                 415
Thr Glu Ile Asn Phe Leu Leu Lys Gln Ala Leu Thr Ile Val Gly Thr
            420                 425                 430
Leu Pro Phe Thr Tyr Met Leu Glu Lys Trp Arg Trp Met Val Phe Lys

-continued

```
                435                 440                 445
Gly Glu Ile Pro Lys Asp Gln Trp Met Lys Trp Trp Glu Met Lys
        450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                        485                 490                 495

Arg Tyr Tyr Thr Arg Thr Leu Tyr Gln Phe Gln Phe Gln Glu Ala Leu
                500                 505                 510

Cys Gln Ala Ala Lys His Glu Gly Pro Leu His Lys Cys Asp Ile Ser
            515                 520                 525

Asn Ser Thr Glu Ala Gly Gln Lys Leu Phe Asn Met Leu Arg Leu Gly
        530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                        565                 570                 575

Trp Leu Lys Asp Gln Asn Lys Asn Ser Phe Val Gly Trp Ser Thr Asp
                580                 585                 590

Trp Ser Pro Tyr Ala Asp Gln Ser Ile Lys Val Arg Ile Ser Leu Lys
            595                 600                 605

Ser Ala Leu Gly Asp Lys Ala Tyr Glu Trp Asn Asp Asn Glu Met Tyr
        610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                        645                 650                 655

Asn Leu Lys Pro Arg Ile Ser Phe Asn Phe Phe Val Thr Ala Pro Lys
                660                 665                 670

Asn Val Ser Asp Ile Ile Pro Arg Thr Glu Val Glu Lys Ala Ile Arg
            675                 680                 685

Met Ser Arg Ser Arg Ile Asn Asp Ala Phe Arg Leu Asn Asp Asn Ser
        690                 695                 700

Leu Glu Phe Leu Gly Ile Gln Pro Thr Leu Gly Pro Pro Asn Gln Pro
705                 710                 715                 720

Pro Val Ser Asp Lys Thr His Thr Cys Pro Pro Cys Pro Ala Pro Glu
                        725                 730                 735

Leu Leu Gly Gly Pro Ser Val Phe Leu Phe Pro Pro Lys Pro Lys Asp
                740                 745                 750

Thr Leu Met Ile Ser Arg Thr Pro Glu Val Thr Cys Val Val Val Asp
            755                 760                 765

Val Ser His Glu Asp Pro Glu Val Lys Phe Asn Trp Tyr Val Asp Gly
        770                 775                 780

Val Glu Val His Asn Ala Lys Thr Lys Pro Arg Glu Glu Gln Tyr Asn
785                 790                 795                 800

Ser Thr Tyr Arg Val Val Ser Val Leu Thr Val Leu His Gln Asp Trp
                        805                 810                 815

Leu Asn Gly Lys Glu Tyr Lys Cys Lys Val Ser Asn Lys Ala Leu Pro
                820                 825                 830

Ala Pro Ile Glu Lys Thr Ile Ser Lys Ala Lys Gly Gln Pro Arg Glu
            835                 840                 845

Pro Gln Val Tyr Thr Leu Pro Pro Ser Arg Asp Glu Leu Thr Lys Asn
        850                 855                 860
```

```
Gln Val Ser Leu Thr Cys Leu Val Lys Gly Phe Tyr Pro Ser Asp Ile
865                 870                 875                 880

Ala Val Glu Trp Glu Ser Asn Gly Gln Pro Glu Asn Asn Tyr Lys Thr
                885                 890                 895

Thr Pro Pro Val Leu Asp Ser Asp Gly Ser Phe Phe Leu Tyr Ser Lys
            900                 905                 910

Leu Thr Val Asp Lys Ser Arg Trp Gln Gln Gly Asn Val Phe Ser Cys
        915                 920                 925

Ser Val Met His
    930

<210> SEQ ID NO 30
<211> LENGTH: 40
<212> TYPE: DNA
<213> ORGANISM: Artificial Sequence
<220> FEATURE:
<223> OTHER INFORMATION: Synthetic

<400> SEQUENCE: 30
atccagcctc cggactctag agttaactgg taagtttagt                    40

<210> SEQ ID NO 31
<211> LENGTH: 59
<212> TYPE: DNA
<213> ORGANISM: Artificial Sequence
<220> FEATURE:
<223> OTHER INFORMATION: Synthetic

<400> SEQUENCE: 31
gttgccttta cttctaggcc tgccgccacc atggagttcg gcctgagctg gctgttcct    59

<210> SEQ ID NO 32
<211> LENGTH: 16
<212> TYPE: DNA
<213> ORGANISM: Artificial Sequence
<220> FEATURE:
<223> OTHER INFORMATION: Synthetic

<400> SEQUENCE: 32
aacagctatg accatg                                              16

<210> SEQ ID NO 33
<211> LENGTH: 45
<212> TYPE: DNA
<213> ORGANISM: Artificial Sequence
<220> FEATURE:
<223> OTHER INFORMATION: Synthetic

<400> SEQUENCE: 33
atgtacgggc cagatatacg cgttcgttac ataacttacg gtaaa              45

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34
tgattattga ctagtatctg cgttacataa cttacggtaa                    40

<210> SEQ ID NO 35
<211> LENGTH: 40
```

```
<212> TYPE: DNA
<213> ORGANISM: Artificial Sequence
<220> FEATURE:
<223> OTHER INFORMATION: Synthetic

<400> SEQUENCE: 35
actccatggt ggcggcaggc ctagaagtaa aggcaacatc                              40

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
ataaagatat tttattttcg aattctcagc                                        30

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
ctgttctacc agagcagcct ggcca                                             25

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
ctgggagaac agcatgctga ccgac                                             25

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
agagcatcaa ggtgagaatc agcct                                             25

<210> SEQ ID NO 40
<211> LENGTH: 25
<212> TYPE: DNA
<213> ORGANISM: Artificial Sequence
<220> FEATURE:
<223> OTHER INFORMATION: Synthetic

<400> SEQUENCE: 40
cggccagccc gagaacaact acaag                                             25

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
```
tcgtggggca cgggctccac cacgc                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic

<400> SEQUENCE: 42
gcgtggtgga gcccgtgccc cacga                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic

<400> SEQUENCE: 43
tgggggggaa caggaacacg ctggg                                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
gcggccccag cgtgttcctg ttccc                                              25

<210> SEQ ID NO 45
<211> LENGTH: 39
<212> TYPE: DNA
<213> ORGANISM: Artificial Sequence
<220> FEATURE:
<223> OTHER INFORMATION: Synthetic

<400> SEQUENCE: 45
gaatcctgat gtgcaccaag gtgaccatgg acgacttcc                               39

<210> SEQ ID NO 46
<211> LENGTH: 49
<212> TYPE: DNA
<213> ORGANISM: Artificial Sequence
<220> FEATURE:
<223> OTHER INFORMATION: Synthetic

<400> SEQUENCE: 46
ggtgaccatg gacgacttcc tgaccgccca cgccgagatg ggccacatc                    49

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
gcatgttgaa cagcttct                                                      18

<210> SEQ ID NO 48
<211> LENGTH: 49
<212> TYPE: DNA
<213> ORGANISM: Artificial Sequence

```
<220> FEATURE:
<223> OTHER INFORMATION: Synthetic

<400> SEQUENCE: 48
gaccatggac gacttcctga ccgcccacca ccagatgggc cacatccag            49

<210> SEQ ID NO 49
<211> LENGTH: 49
<212> TYPE: DNA
<213> ORGANISM: Artificial Sequence
<220> FEATURE:
<223> OTHER INFORMATION: Synthetic

<400> SEQUENCE: 49
gaccatggac gacttcctga ccgcccacgc ccagatgggc cacatccag            49

<210> SEQ ID NO 50
<211> LENGTH: 44
<212> TYPE: DNA
<213> ORGANISM: Artificial Sequence
<220> FEATURE:
<223> OTHER INFORMATION: Synthetic

<400> SEQUENCE: 50
cgccaagctc tagctagagg tcgacgcggc cgctcggtcc gcac                 44

<210> SEQ ID NO 51
<211> LENGTH: 49
<212> TYPE: DNA
<213> ORGANISM: Artificial Sequence
<220> FEATURE:
<223> OTHER INFORMATION: Synthetic

<400> SEQUENCE: 51
ttcctgctga gaaacggcgc caacgagggc ttccaccagg ccgtgggcg            49

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ggggtctcac gttcatgttc                                            20

<210> SEQ ID NO 53
<211> LENGTH: 40
<212> TYPE: DNA
<213> ORGANISM: Artificial Sequence
<220> FEATURE:
<223> OTHER INFORMATION: Synthetic

<400> SEQUENCE: 53
gagatggatg gtgttcaagg gcgagatccc caaggaccag                      40

<210> SEQ ID NO 54
<211> LENGTH: 38
<212> TYPE: DNA
<213> ORGANISM: Artificial Sequence
<220> FEATURE:
<223> OTHER INFORMATION: Synthetic

<400> SEQUENCE: 54
ctggtccttg gggatctcgc ccttgaacac catccatc                        38
```

```
<210> SEQ ID NO 55
<211> LENGTH: 25
<212> TYPE: DNA
<213> ORGANISM: Artificial Sequence
<220> FEATURE:
<223> OTHER INFORMATION: Synthetic

<400> SEQUENCE: 55
ccgaagggca cggtcaggct gtaca                                              25

<210> SEQ ID NO 56
<211> LENGTH: 25
<212> TYPE: DNA
<213> ORGANISM: Artificial Sequence
<220> FEATURE:
<223> OTHER INFORMATION: Synthetic

<400> SEQUENCE: 56
tgtacagcct gaccgtgccc ttcgg                                              25

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
ggaaccccta gtgatggagt t                                                  21

<210> SEQ ID NO 58
<211> LENGTH: 16
<212> TYPE: DNA
<213> ORGANISM: Artificial Sequence
<220> FEATURE:
<223> OTHER INFORMATION: Synthetic

<400> SEQUENCE: 58
cggcctcagt gagcga                                                        16

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
cactccctct ctgcgcgctc g                                                  21

<210> SEQ ID NO 60
<211> LENGTH: 2850
<212> TYPE: DNA
<213> ORGANISM: Artificial Sequence
<220> FEATURE:
<223> OTHER INFORMATION: Synthetic

<400> SEQUENCE: 60
cagagcacca tcgaggagca ggccaagacc ttcctggaca gttcaacca cgaggccgag          60 gacctgttct accagagcag cctggccagc tggaactaca acaccaacat caccgaggag        120
aacgtgcaga acatgaacaa cgccggcgac aagtggagcg ccttcctgaa ggagcagagc        180
accctggccc agatgtaccc cctgcaggag atccagaacc tgaccgtgaa gctgcagctg        240
caggccctgc agcagaacgg cagcagcgtg ctgagcgagg acaagagcaa gagactgaac        300
```

| | |
|---|---|
| accatcctga acaccatgag caccatctac agcaccggca aggtgtgcaa ccccgacaac | 360 |
| cccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctacccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagaaca gcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacca cgagatgggc | 1080 |
| cacatccagt acgacatggc ctacgccgcc cagcccttcc tgctgagaaa cggcgccaac | 1140 |
| gagggcttcc acgaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg ggcaccctgc ccttcaccta catgctggag | 1320 |
| aagtggagat ggatggtgtt caaggacgag atccccaagg accagtggat gaagaagtgg | 1380 |
| tgggagatga agagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca gtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagacccct gctgaactac ttcgagcccc tgttccacctg gctgaaggac | 1740 |
| cagaacaaga acagcttcgt gggctggagc accgactgga gccccctacgc cgaccagagc | 1800 |
| atcaaggtga aatcagcct gaagagcgcc ctgggcgaca aggcctacga gtggaacgac | 1860 |
| aacgagatgt acctgttcag aagcagcgtg gcctacgcca tgagacagta cttcctgaag | 1920 |
| gtgaagaacc agatgatcct gttcggcgag gaggacgtga gagtggccaa cctgaagccc | 1980 |
| agaatcagct tcaacttctt cgtgaccgcc cccaagaacg tgagcgacat catccccaga | 2040 |
| accgaggtgg agaaggccat cagaatgagc agaagcagaa tcaacgacgc cttcagactg | 2100 |
| aacgacaaca gcctggagtt cctgggcatc cagcccaccc tgggcccccc caaccagccc | 2160 |
| cccgtgagcg acaagaccca cctgcccccc cctgccccg cccccgagct gctgggcggc | 2220 |
| cccagcgtgt cctgttccc ccccaagccc aaggacaccc tgatgatcag cagaacccccc | 2280 |
| gaggtgacct gcgtggtggt ggacgtgagc cacgaggacc ccgaggtgaa gttcaactgg | 2340 |
| tacgtggacg gcgtggaggt gcacaacgcc aagaccaagc ccagagagga gcagtacaac | 2400 |
| agcacctaca gagtggtgag cgtgctgacc gtgctgcacc aggactggct gaacggcaag | 2460 |
| gagtacaagt gcaaggtgag caacaaggcc ctgcccgccc ccatcgagaa gaccatcagc | 2520 |
| aaggccaagg gccagcccag agagcccag gtgtacaccc tgcccccccag cagagacgag | 2580 |
| ctgaccaaga accaggtgag cctgacctgc ctggtgaagg gcttctaccc cagcgacatc | 2640 |

| | |
|---|---|
| gccgtggagt gggagagcaa cggccagccc gagaacaact acaagaccac ccccccgtg | 2700 |
| ctggacagcg acggcagctt cttcctgtac agcaagctga ccgtggacaa gagcagatgg | 2760 |
| cagcagggca acgtgttcag ctgcagcgtg atgcacgagg ccctgcacaa ccactacacc | 2820 |
| cagaagagcc tgagcctgag ccccggctga | 2850 |

<210> SEQ ID NO 61
<211> LENGTH: 2850
<212> TYPE: DNA
<213> ORGANISM: Homo sapiens

<400> SEQUENCE: 61

| | |
|---|---|
| cagagcacca tcgaggagca ggccaagacc ttcctggaca agttcaacca cgaggccgag | 60 |
| gacctgttct accagagcag cctggccagc tggaactaca acaccaacat caccgaggag | 120 |
| aacgtgcaga acatgaacaa cgccggcgac aagtggagcg ccttcctgaa ggagcagagc | 180 |
| accctggccc agatgtaccc cctgcaggag atccagaacc tgaccgtgaa gctgcagctg | 240 |
| caggccctgc agcagaacgg cagcagcgtg ctgagcgaga caagagcaa gagactgaac | 300 |
| accatcctga acaccatgag caccatctac agcaccggca aggtgtgcaa ccccgacaac | 360 |
| ccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctacccccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagaaca gcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacca cgagatgggc | 1080 |
| cacatccagt acgacatggc ctacgccgcc cagcccttcc tgctgagaaa cggcgccaac | 1140 |
| gagggcttcc acgaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg ggcaccctgc ccttcaccta catgctggag | 1320 |
| aagtggagat ggatggtgtt caagggcgag atccccaagg accagtggat gaagaagtgg | 1380 |
| tgggagatga agagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca agtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagaccct gctgaactac ttcgagcccc tgttcacctg gctgaaggac | 1740 |
| cagaacaaga acagcttcgt gggctggagc accgactgga gccccctacgc cgaccagagc | 1800 |
| atcaaggtga gaatcagcct gaagagcgcc ctggccgaca ggcctacga gtggaacgac | 1860 |
| aacgagatgt acctgttcag aagcagcgtg gcctacgcca tgagacagta cttcctgaag | 1920 |

```
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggcccccc caaccagccc    2160
cccgtgagcg acaagaccca cacctgcccc cctgccccg  ccccgagct gctgggcggc    2220 cccagcgtgt tcctgttccc ccccaagccc aaggacaccc tgatgatcag cagaaccccc    2280
gaggtgacct gcgtggtggt ggacgtgagc cacgaggacc ccgaggtgaa gttcaactgg    2340
tacgtggacg gcgtggaggt gcacaacgcc aagaccaagc ccagagagga gcagtacaac    2400
agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagcccag  gtgtacaccc tgcccccag  cagagacgag    2580 ctgaccaaga accaggtgag cctgacctgc ctggtgaagg gcttctaccc cagcgacatc    2640
gccgtggagt gggagagcaa cggccagccc gagaacaact acaagaccac ccccccgtg    2700 ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                    2850

<210> SEQ ID NO 62
<211> LENGTH: 2850
<212> TYPE: DNA
<213> ORGANISM: Artificial Sequence
<220> FEATURE:
<223> OTHER INFORMATION: Synthetic

<400> SEQUENCE: 62
cagagcacca tcgaggagca ggccaagacc ttcctggaca agttcaacca cgaggccgag      60
gacctgttct accagagcag cctggccagc tggaactaca caccaacat caccgaggag     120 aacgtgcaga acatgaacaa cgccggcgac aagtggagcg ccttcctgaa ggagcagagc     180
accctggccc agatgtaccc cctgcaggag atccagaacc tgaccgtgaa gctgcagctg     240
caggccctgc agcagaacgg cagcagcgtg ctgagcgagg acaagagcaa gagactgaac     300
accatcctga acaccatgag caccatctac agcaccggca aggtgtgcaa ccccgacaac     360
ccccaggagt gcctgctgct ggagcccggc ctgaacgaga tcatggccaa cagcctggac     420
tacaacgaga gactgtgggc ctgggagagc tggagaagcg aggtgggcaa gcagctgaga     480
cccctgtacg aggagtacgt ggtgctgaag aacgagatgg ccagagccaa ccactacgag     540
gactacggcg actactggag aggcgactac gaggtgaacg gcgtggacgg ctacgactac     600
agcagaggcc agctgatcga ggacgtggag cacaccttcg aggagatcaa gcccctgtac     660
gagcacctgc acgcctacgt gagagccaag ctgatgaacg cctacccag  ctacatcagc     720 cccatcggct gcctgcccgc ccacctgctg ggcgacatgt ggggcagatt ctggaccaac     780
ctgtacagcc tgaccgtgcc cttcggccag aagcccaaca tcgacgtgac cgacgccatg     840
gtggaccagg cctgggacgc ccagagaatc ttcaaggagg ccgagaagtt cttcgtgagc     900
gtgggcctgc ccaacatgac ccagggcttc tgggagaaca gcatgctgac cgaccccgc     960 aacgtgcaga aggccgtgtg ccaccccacc gcctggacc  tgggcaaggg cgacttcaga    1020
atcctgatgt gcaccaaggt gaccatggac gacttcctga ccgcccacca cgagatgggc    1080
```

| | |
|---|---|
| cacatccagt acgacatggc ctacgccgcc cagcccttcc tgctgagaaa cggcgccaac | 1140 |
| gagggcttcc accaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg gcaccctgc ccttcaccta catgctggag | 1320 |
| aagtggagat ggatggtgtt caaggacgag atccccaagg accagtggat gaagaagtgg | 1380 |
| tgggagatga agagagagat cgtgggcgtg gtggagcccg tgccccacga cgagacctac | 1440 |
| tgcgacccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca agtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagaccccct gctgaactac ttcgagcccc tgttcacctg gctgaaggac | 1740 |
| cagaacaaga cagcttcgt gggctggagc accgactgga gccctacgc cgaccagagc | 1800 |
| atcaaggtga gaatcagcct gaagagcgcc ctgggcgaca aggcctacga gtggaacgac | 1860 |
| aacgagatgt acctgttcag aagcagcgtg gcctacgcca tgagacagta cttcctgaag | 1920 |
| gtgaagaacc agatgatcct gttcggcgag gaggacgtga gagtggccaa cctgaagccc | 1980 |
| agaatcagct caacttctt cgtgaccgcc cccaagaacg tgagcgacat catccccaga | 2040 |
| accgaggtgg agaaggccat cagaatgagc agaagcagaa tcaacgacgc cttcagactg | 2100 |
| aacgacaaca gcctggagtt cctgggcatc cagcccaccc tgggccccc caaccagccc | 2160 |
| cccgtgagcg acaagaccca cctgccccc cctgccccg ccccgagct gctgggcggc | 2220 |
| cccagcgtgt tcctgttccc ccccaagccc aaggacaccc tgatgatcag cagaaccccc | 2280 |
| gaggtgacct gcgtggtggt ggacgtgagc cacgaggacc ccgaggtgaa gttcaactgg | 2340 |
| tacgtggacg gcgtggaggt gcacaacgcc aagaccaagc cagagagga gcagtacaac | 2400 |
| agcacctaca gagtggtgag cgtgctgacc gtgctgcacc aggactggct gaacggcaag | 2460 |
| gagtacaagt gcaaggtgag caacaaggcc ctgcccgccc ccatcgagaa gaccatcagc | 2520 |
| aaggccaagg gccagcccag agagcccag gtgtacaccc tgccccccag cagagacgag | 2580 |
| ctgaccaaga accaggtgag cctgacctgc ctggtgaagg gcttctaccc cagcgacatc | 2640 |
| gccgtggagt gggagagcaa cggccagccc gagaacaact acaagaccac ccccccgtg | 2700 |
| ctggacagcg acggcagctt cttcctgtac agcaagctga ccgtggacaa gagcagatgg | 2760 |
| cagcagggca cgtgttcag ctgcagcgtg atgcacgagg ccctgcacaa ccactacacc | 2820 |
| cagaagagcc tgagcctgag ccccggctga | 2850 |

<210> SEQ ID NO 63
<211> LENGTH: 2850
<212> TYPE: DNA
<213> ORGANISM: Artificial Sequence
<220> FEATURE:
<223> OTHER INFORMATION: Synthetic

<400> SEQUENCE: 63

| | |
|---|---|
| cagagcacca tcgaggagca ggccaagacc ttcctggaca agttcaacca cgaggccgag | 60 |
| gacctgttct accagagcag cctggccagc tggaactaca caccaacat caccgaggag | 120 |
| aacgtgcaga acatgaacaa cgccggcgac aagtggagcg ccttcctgaa ggagcagagc | 180 |
| accctggccc agatgtaccc cctgcaggag atccagaacc tgaccgtgaa gctgcagctg | 240 |
| caggccctgc agcagaacgg cagcagcgtg ctgagcgagg acaagagcaa gagactgaac | 300 |

| | |
|---|---|
| accatcctga acaccatgag caccatctac agcaccggca aggtgtgcaa ccccgacaac | 360 |
| ccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gccctgtac | 660 |
| gagcacctgc acgcctacgt gagagccaag ctgatgaacg cctacccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagaaca gcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacgc cgagatgggc | 1080 |
| cacatccagt acgacatggc ctacgccgcc cagcccttcc tgctgagaaa cggcgccaac | 1140 |
| gagggcttcc accaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg ggcaccctgc ccttcaccta catgctggag | 1320 |
| aagtggagat ggatggtgtt caagggcgag atccccaagg accagtggat gaagaagtgg | 1380 |
| tgggagatga agagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca agtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagacccct gctgaactac ttcgagcccc tgttcacctg gctgaaggac | 1740 |
| cagaacaaga acagcttcgt gggctggagc accgactgga gccccctacgc cgaccagagc | 1800 |
| atcaaggtga gaatcagcct gaagagcgcc ctgggcgaca aggcctacga gtggaacgac | 1860 |
| aacgagatgt acctgttcag aagcagcgtg gcctacgcca tgagacagta cttcctgaag | 1920 |
| gtgaagaacc agatgatcct gttcggcgag gaggacgtga gagtggccaa cctgaagccc | 1980 |
| agaatcagct tcaacttctt cgtgaccgcc cccaagaacg tgagcgacat catccccaga | 2040 |
| accgaggtgg agaaggccat cagaatgagc agaagcagaa tcaacgacgc cttcagactg | 2100 |
| aacgacaaca gcctggagtt cctgggcatc cagcccaccc tgggccccc caaccagccc | 2160 |
| cccgtgagcg acaagaccca cctgcccc cctgccccg ccccgagct gctgggcggc | 2220 |
| cccagcgtgt cctgttccc ccccaagccc aaggacaccc tgatgatcag cagaacccc | 2280 |
| gaggtgacct gcgtggtggt ggacgtgagc cacgaggacc ccgaggtgaa gttcaactgg | 2340 |
| tacgtggacg gcgtggaggt gcacaacgcc aagaccaagc ccagagagga gcagtacaac | 2400 |
| agcacctaca gagtggtgag cgtgctgacc gtgctgcacc aggactggct gaacggcaag | 2460 |
| gagtacaagt gcaaggtgag caacaaggcc ctgcccgccc ccatcgagaa gaccatcagc | 2520 |
| aaggccaagg gccagcccag agagcccag gtgtacaccc tgcccccag cagagacgag | 2580 |
| ctgaccaaga accaggtgag cctgacctgc ctggtgaagg gcttctaccc cagcgacatc | 2640 |

```
gccgtggagt gggagagcaa cggccagccc gagaacaact acaagaccac ccccccgtg    2700 ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                     2850
```

<210> SEQ ID NO 64
<211> LENGTH: 2850
<212> TYPE: DNA
<213> ORGANISM: Artificial Sequence
<220> FEATURE:
<223> OTHER INFORMATION: Synthetic

<400> SEQUENCE: 64

```
cagagcacca tcgaggagca ggccaagacc ttcctggaca agttcaacca cgaggccgag     60
gacctgttct accagagcag cctggccagc tggaactaca caccaacat caccgaggag    120 aacgtgcaga acatgaacaa cgccggcgac aagtggagcg ccttcctgaa ggagcagagc    180
accctggccc agatgtaccc cctgcaggag atccagaacc tgaccgtgaa gctgcagctg    240
caggccctgc agcagaacgg cagcagcgtg ctgagcgagg acaagagcaa gagactgaac    300
accatcctga caccatgag caccatctac agcaccggca agtgtgcaa ccccgacaac    360 ccccaggagt gcctgctgct ggagcccggc ctgaacgaga tcatggccaa cagcctggac    420
tacaacgaga gactgtgggc ctgggagagc tggaagcg aggtgggcaa gcagctgaga    480
cccctgtacg aggagtacgt ggtgctgaag aacgagatgg ccagagccaa ccactacgag    540
gactacggcg actactggag aggcgactac gaggtgaacg gcgtggacgg ctacgactac    600
agcagaggcc agctgatcga ggacgtggag cacaccttcg aggagatcaa gcccctgtac    660
gagcacctgc acgcctacgt gagagccaag ctgatgaacg cctacccag ctacatcagc    720 cccatcggct gcctgccgc ccacctgctg ggcgacatgt ggggcagatt ctggaccaac    780
ctgtacagcc tgaccgtgcc cttcggccag aagcccaaca tcgacgtgac cgacgccatg    840
gtggaccagg cctgggacgc ccagagaatc ttcaaggagg ccgagaagtt cttcgtgagc    900
gtgggcctgc ccaacatgac ccagggcttc tgggagaaca gcatgctgac cgaccccggc    960
aacgtgcaga aggccgtgtg ccacccacc gcctgggacc tgggcaaggg cgacttcaga   1020
atcctgatgt gcaccaaggt gaccatggac gacttcctga ccgcccacca ccagatgggc   1080
cacatccagt acgacatggc ctacgccgcc cagccttcc tgctgagaaa cggcgccaac   1140
gagggcttcc accaggccgt gggcgagatc atgagcctga cgccgccac ccccaagcac   1200 ctgaagagca tcggcctgct gagccccgac ttccaggagg acaacgagac cgagatcaac   1260
ttcctgctga gcaggccct gaccatcgtg ggcaccctgc ccttcaccta catgctggag   1320
aagtggagat ggatggtgtt caagggcgag atccccaagg accagtggat gaagaagtgg   1380
tgggagatga gagagagat cgtgggcgtg gtggagcccg tgccccacga cgagacctac   1440 tgcgacccg ccagcctgtt ccacgtgagc aacgactaca gcttcatcag atactacacc   1500
agaaccctgt accagttcca gttccaggag gccctgtgcc aggccgccaa gcacgagggc   1560 ccctgcaca agtgcgacat cagcaacagc accgaggccg ccagaagct gttcaacatg   1620 ctgagactgg gcaagagcga gccctggacc ctggcctgg agaacgtggt gggcgccaag   1680
aacatgaacg tgagaccct gctgaactac ttcgagccc tgttcacctg gctgaaggac   1740
cagaacaaga acagcttcgt gggctggagc accgactgga cccctacgc cgaccagagc   1800 atcaaggtga gaatcagcct gaagagcgcc ctgggcgaca aggcctacga gtggaacgac   1860
```

```
aacgagatgt acctgttcag aagcagcgtg gcctacgcca tgagacagta cttcctgaag    1920
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggcccccc caaccagccc    2160
cccgtgagcg acaagaccca cacctgcccc cctgccccg ccccgagct gctgggcggc     2220 cccagcgtgt tcctgttccc ccccaagccc aaggacaccc tgatgatcag cagaacccc    2280 gaggtgacct gcgtggtggt ggacgtgagc cacgaggacc ccgaggtgaa gttcaactgg    2340
tacgtggacg gcgtggaggt gcacaacgcc aagaccaagc ccagagagga gcagtacaac    2400
agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagcccag gtgtacaccc tgcccccag cagagacgag    2580 ctgaccaaga accaggtgag cctgacctgc ctggtgaagg gcttctaccc cagcgacatc    2640
gccgtggagt gggagagcaa cggccagccc gagaacaact acaagaccac ccccccgtg    2700 ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                    2850
```

<210> SEQ ID NO 65
<211> LENGTH: 2850
<212> TYPE: DNA
<213> ORGANISM: Artificial Sequence
<220> FEATURE:
<223> OTHER INFORMATION: Synthetic

<400> SEQUENCE: 65

```
cagagcacca tcgaggagca ggccaagacc ttcctggaca agttcaacca cgaggccgag     60
gacctgttct accagagcag cctggccagc tggaactaca caccaacat caccgaggag    120 aacgtgcaga acatgaacaa cgccggcgac aagtggagcg ccttcctgaa ggagcagagc    180
accctggccc agatgtaccc cctgcaggag atccagaacc tgaccgtgaa gctgcagctg    240
caggccctgc agcagaacgg cagcagcgtg ctgagcgagg acaagagcaa gagactgaac    300
accatcctga caccatgag caccatctac agcaccggca aggtgtgcaa ccccgacaac    360
ccccaggagt gcctgctgct ggagcccggc ctgaacgaga tcatggccaa cagcctggac    420
tacaacgaga gactgtgggc ctgggagagc tggagaagcg aggtgggcaa gcagctgaga    480
cccctgtacg aggagtacgt ggtgctgaag aacgagatgg ccagagccaa ccactacgag    540
gactacggcg actactggag aggcgactac gaggtgaacg gcgtggacgg ctacgactac    600
agcagaggcc agctgatcga ggacgtggag cacaccttcg aggagatcaa gcccctgtac    660
gagcacctgc acgcctacgt gagagccaag ctgatgaacg cctaccccag ctacatcagc    720
cccatcggct gcctgcccgc ccacctgctg ggcgacatgt ggggcagatt ctggaccaac    780
ctgtacagcc tgaccgtgcc cttcggccag aagcccaaca tcgacgtgac cgacgccatg    840 gtgaccagg cctggacgc ccagagaatc ttcaaggagg ccgagaagtt cttcgtgagc    900
gtgggcctgc ccaacatgac ccagggcttc tgggagaaca gcatgctgac cgaccccggc    960
aacgtgcaga aggccgtgtg ccaccccacc gcctgggacc tgggcaaggg cgacttcaga    1020
```

| | | |
|---|---|---|
| atcctgatgt gcaccaaggt gaccatggac gacttcctga ccgcccacgc ccagatgggc | 1080 | |
| cacatccagt acgacatggc ctacgccgcc cagcccttcc tgctgagaaa cggcgccaac | 1140 | |
| gagggcttcc accaggccgt gggcgagatc atgagcctga gcgccgccac ccccaagcac | 1200 | |
| ctgaagagca tcggcctgct gagccccgac ttccaggagg acaacgagac cgagatcaac | 1260 | |
| ttcctgctga agcaggccct gaccatcgtg gcaccctgc ccttcaccta catgctggag | 1320 | |
| aagtggagat ggatggtgtt caagggcgag atccccaagg accagtggat gaagaagtgg | 1380 | |
| tgggagatga agagagagat cgtgggcgtg gtggagcccg tgccccacga cgagacctac | 1440 | |
| tgcgaccccg ccagcctgtt ccacgtgagc aacgactaca gcttcatcag atactacacc | 1500 | |
| agaaccctgt accagttcca gttccaggag ccctgtgcc aggccgccaa gcacgagggc | 1560 | |
| cccctgcaca gtgcgacat cagcaacagc accgaggccg ccagaagct gttcaacatg | 1620 | |
| ctgagactgg gcaagagcga gccctggacc ctggccctgg agaacgtggt gggcgccaag | 1680 | |
| aacatgaacg tgagacccct gctgaactac ttcgagcccc tgttcacctg gctgaaggac | 1740 | |
| cagaacaaga acagcttcgt gggctggagc accgactgga gccccctacgc cgaccagagc | 1800 | |
| atcaaggtga gaatcagcct gaagagcgcc ctgggcgaca aggcctacga gtggaacgac | 1860 | |
| aacgagatgt acctgttcag aagcagcgtg gcctacgcca tgagacagta cttcctgaag | 1920 | |
| gtgaagaacc agatgatcct gttcggcgag gaggacgtga gagtggccaa cctgaagccc | 1980 | |
| agaatcagct tcaacttctt cgtgaccgcc cccaagaacg tgagcgacat catcccagg | 2040 | |
| accgaggtgg agaaggccat cagaatgagc agaagcagaa tcaacgacgc cttcagactg | 2100 | |
| aacgacaaca gcctggagtt cctgggcatc cagcccaccc tgggcccccc caaccagccc | 2160 | |
| cccgtgagcg acaagaccca cacctgcccc cctgcccg cccccgagct gctgggcggc | 2220 | |
| cccagcgtgt tcctgttccc ccccaagccc aaggacaccc tgatgatcag cagaaccccc | 2280 | |
| gaggtgacct gcgtggtggt ggacgtgagc cacgaggacc ccgaggtgaa gttcaactgg | 2340 | |
| tacgtggacg gcgtggaggt gcacaacgcc aagaccaagc cagagagga gcagtacaac | 2400 | |
| agcacctaca gagtggtgag cgtgctgacc gtgctgcacc aggactggct gaacggcaag | 2460 | |
| gagtacaagt gcaaggtgag caacaaggcc ctgcccgccc ccatcgagaa gaccatcagc | 2520 | |
| aaggccaagg ccagcccag agagccccag gtgtacaccc tgcccccag cagagacgag | 2580 | |
| ctgaccaaga accaggtgag cctgacctgc ctggtgaagg gcttctaccc cagcgacatc | 2640 | |
| gccgtggagt gggagagcaa cggccagccc gagaacaact acaagaccac cccccccgtg | 2700 | |
| ctggacagcg acggcagctt cttcctgtac agcaagctga ccgtggacaa gagcagatgg | 2760 | |
| cagcagggca acgtgttcag ctgcagcgtg atgcacgagg ccctgcacaa ccactacacc | 2820 | |
| cagaagagcc tgagcctgag ccccggctga | 2850 | |

<210> SEQ ID NO 66
<211> LENGTH: 2850
<212> TYPE: DNA
<213> ORGANISM: Artificial Sequence
<220> FEATURE:
<223> OTHER INFORMATION: Synthetic

<400> SEQUENCE: 66

| | | |
|---|---|---|
| cagagcacca tcgaggagca ggccaagacc ttcctggaca agttcaacca cgaggccgag | 60 | |
| gacctgttct accagagcag cctggccagc tggaactaca acaccaacat caccgaggag | 120 | |
| aacgtgcaga acatgaacaa cgccggcgac aagtggagcg ccttcctgaa ggagcagagc | 180 | |
| accctggccc agatgtaccc cctgcaggag atccagaacc tgaccgtgaa gctgcagctg | 240 | |

```
caggccctgc agcagaacgg cagcagcgtg ctgagcgagg acaagagcaa gagactgaac      300
accatcctga acaccatgag caccatctac agcaccggca aggtgtgcaa ccccgacaac      360
ccccaggagt gcctgctgct ggagcccggc ctgaacgaga tcatggccaa cagcctggac      420
tacaacgaga gactgtgggc ctgggagagc tggagaagcg aggtgggcaa gcagctgaga      480
cccctgtacg aggagtacgt ggtgctgaag aacgagatgg ccagagccaa ccactacgag      540
gactacggcg actactggag aggcgactac gaggtgaacg gcgtggacgg ctacgactac      600
agcagaggcc agctgatcga ggacgtggag cacaccttcg aggagatcaa gccctgtac      660 gagcacctgc acgcctacgt gagagccaag ctgatgaacg cctacccag ctacatcagc      720 cccatcggct gcctgcccgc ccacctgctg ggcgacatgt ggggcagatt ctggaccaac      780
ctgtacagcc tgaccgtgcc cttcggccag aagcccaaca tcgacgtgac cgacgccatg      840
gtggaccagg cctgggacgc cagagaatc ttcaaggagg ccgagaagtt cttcgtgagc      900
gtgggcctgc ccaacatgac ccagggcttc tgggagaaca gcatgctgac cgaccccggc      960
aacgtgcaga aggccgtgtg ccaccccacc gcctgggacc tgggcaaggg cgacttcaga     1020
atcctgatgt gcaccaaggt gaccatggac gacttcctga ccgcccacgc ccagatgggc     1080
cacatccagt acgacatggc ctacgccgcc cagcccttcc tgctgagaaa cggcgccaac     1140
gagggcttcc acgaggccgt gggcgagatc atgagcctga gcgccgccac ccccaagcac     1200
ctgaagagca tcggcctgct gagccccgac ttccaggagg acaacgagac cgagatcaac     1260
ttcctgctga gcaggccct gaccatcgtg ggcaccctgc ccttcaccta catgctggag     1320
aagtggagat ggatggtgtt caagggcgag atccccaagg accagtggat gaagaagtgg     1380
tgggagatga agagagagat cgtgggcgtg gtggagcccg tgccccacga cgagacctac     1440
tgcgaccccg ccagcctgtt ccacgtgagc aacgactaca gcttcatcag atactacacc     1500
agaaccctgt accagttcca gttccaggag gccctgtgcc aggccgccaa gcacgagggc     1560
cccctgcaca agtgcgacat cagcaacagc accgaggccg ccagaagct gttcaacatg     1620 ctgagactgg gcaagagcga gccctggacc ctggccctgg agaacgtggt gggcgccaag     1680
aacatgaacg tgagacccct gctgaactac ttcgagcccc tgttcacctg gctgaaggac     1740
cagaacaaga acagcttcgt gggctggagc accgactgga gccctacgc cgaccagagc     1800 atcaaggtga gaatcagcct gaagagcgcc ctgggcgaca aggcctacga gtggaacgac     1860
aacgagatgt acctgttcag aagcagcgtg gcctacgcca tgagacagta cttcctgaag     1920
gtgaagaacc agatgatcct gttcggcgag gaggacgtga gtggccaa cctgaagccc     1980 agaatcagct tcaacttctt cgtgaccgcc cccaagaacg tgagcgacat catccccaga     2040
accgaggtgg agaaggccat cagaatgagc agaagcagaa tcaacgacgc cttcagactg     2100
aacgacaaca gcctggagtt cctgggcatc cagcccaccc tgggccccc caaccagccc     2160 cccgtgagca caagaccca cacctgcccc ccctgccccg ccccgagct gctgggcggc     2220 cccagcgtgt tcctgttccc ccccaagccc aaggacaccc tgatgatcag cagaaccccc     2280
gaggtgacct gcgtggtggt ggacgtgagc cacgaggacc ccgaggtgaa gttcaactgg     2340
tacgtggacg gcgtggaggt gcacaacgcc aagaccaagc cagagagga gcagtacaac     2400 agcacctaca gagtggtgag cgtgctgacc gtgctgcacc aggactggct gaacggcaag     2460
gagtacaagt gcaaggtgag caacaaggcc ctgcccgccc ccatcgagaa gaccatcagc     2520
aaggccaagg ccagcccag agagcccag gtgtacaccc tgccccccag cagagacgag     2580
```

-continued

| | |
|---|---|
| ctgaccaaga accaggtgag cctgacctgc ctggtgaagg gcttctaccc cagcgacatc | 2640 |
| gccgtggagt gggagagcaa cggccagccc gagaacaact acaagaccac ccccccgtg | 2700 |
| ctggacagcg acggcagctt cttcctgtac agcaagctga ccgtggacaa gagcagatgg | 2760 |
| cagcagggca acgtgttcag ctgcagcgtg atgcacgagg ccctgcacaa ccactacacc | 2820 |
| cagaagagcc tgagcctgag ccccggctga | 2850 |

<210> SEQ ID NO 67
<211> LENGTH: 2850
<212> TYPE: DNA
<213> ORGANISM: Homo sapiens

<400> SEQUENCE: 67

| | |
|---|---|
| cagagcacca tcgaggagca ggccaagacc ttcctggaca agttcaacca cgaggccgag | 60 |
| gacctgttct accagagcag cctggccagc tggaactaca caccaacat caccgaggag | 120 |
| aacgtgcaga acatgaacaa cgccggcgac aagtggagcg ccttcctgaa ggagcagagc | 180 |
| accctggccc agatgtaccc cctgcaggag atccagaacc tgaccgtgaa gctgcagctg | 240 |
| caggccctgc agcagaacgg cagcagcgtg ctgagcgagg acaagagcaa gagactgaac | 300 |
| accatcctga caccatgag caccatctac agcaccggca aggtgtgcaa ccccgacaac | 360 |
| ccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctacccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagaaca gcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacca cgagatgggc | 1080 |
| cacatccagt acgacatggc ctacgccgcc cagccttcc tgctgagaaa cggcgccaac | 1140 |
| gagggcttcc acgaggccgt gggcgagatc atgagcctga cgccgccac ccccaagcac | 1200 |
| ctgaagagca tcggcctgct gagccccgac ttccaggagg acaacgagac cgagatcaac | 1260 |
| ttcctgctga agcaggccct gaccatcgtg ggcaccctgc ccttcaccta catgctggag | 1320 |
| aagtggagat ggatggtgtt caagggcgag atccccaagg accagtggat gaagaagtgg | 1380 |
| tgggagatga gagagagat cgtgggcgtg gtggagcccg tgcccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca gtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagacccct gctgaactac ttcgagcccc tgttcacctg gctgaaggac | 1740 |
| cagaacaaga acagcttcgt gggctggagc accgactgga gccccctacgc cgaccagagc | 1800 |
| atcaaggtga gaatcagcct gaagagcgcc ctgggcgaca aggcctacga gtggaacgac | 1860 |

```
aacgagatgt acctgttcag aagcagcgtg gcctacgcca tgagacagta cttcctgaag   1920
gtgaagaacc agatgatcct gttcggcgag gaggacgtga gagtggccaa cctgaagccc   1980
agaatcagct tcaacttctt cgtgaccgcc cccaagaacg tgagcgacat catccccaga   2040
accgaggtgg agaaggccat cagaatgagc agaagcagaa tcaacgacgc cttcagactg   2100
aacgacaaca gcctggagtt cctgggcatc cagcccaccc tgggccccccc caaccagccc   2160 cccgtgagcg acaagaccca cacctgcccc cctgcccccg cccccgagct gctgggcggc   2220
cccagcgtgt tcctgttccc ccccaagccc aaggacaccc tgatgatcag cagaacccccc   2280 gaggtgaccl gcgtggtggt ggacgtgagc cacgaggacc ccgaggtgaa gttcaactgg   2340
tacgtggacg gcgtggaggt gcacaacgcc aagaccaagc ccagagagga gcagtacaac   2400
agcacctaca gagtggtgag cgtgctgacc gtgctgcacc aggactggct gaacggcaag   2460
gagtacaagt gcaaggtgag caacaaggcc ctgcccgccc ccatcgagaa gaccatcagc   2520
aaggccaagg gccagcccag agagcccag gtgtacaccc tgcccccccag cagagacgag   2580 ctgaccaaga accaggtgag cctgacctgc ctggtgaagg gcttctaccc cagcgacatc   2640
gccgtggagt gggagagcaa cggccagccc gagaacaact acaagaccac ccccccgtg   2700 ctggacagcg acggcagctt cttcctgtac agcaagctga ccgtggacaa gagcagatgg   2760
cagcagggca acgtgttcag ctgcagcgtg atgcacgagg ccctgcacaa ccactacacc   2820
cagaagagcc tgagcctgag ccccggctga                                    2850

<210> SEQ ID NO 68
<211> LENGTH: 2850
<212> TYPE: DNA
<213> ORGANISM: Artificial Sequence
<220> FEATURE:
<223> OTHER INFORMATION: Synthetic

<400> SEQUENCE: 68
cagagcacca tcgaggagca ggccaagacc ttcctggaca agttcaacca cgaggccgag    60
gacctgttct accagagcag cctggccagc tggaactaca caccaacat caccgaggag   120 aacgtgcaga acatgaacaa cgccggcgac aagtggagcg ccttcctgaa ggagcagagc   180 acccctggccc agatgtaccc cctgcaggag atccagaacc tgaccgtgaa gctgcagctg   240
caggccctgc agcagaacgg cagcagcgtg ctgagcgagg acaagagcaa gagactgaac   300
accatcctga acaccatgag caccatctac agcaccggca aggtgtgcaa ccccgacaac   360
ccccaggagt gcctgctgct ggagcccggc ctgaacgaga tcatggccaa cagcctggac   420
tacaacgaga gactgtgggc ctgggagagc tggagaagcg aggtgggcaa gcagctgaga   480
cccctgtacg aggagtacgt ggtgctgaag aacgagatgg ccagagccaa ccactacgag   540
gactacggcg actactggag aggcgactac gaggtgaacg gcgtggacgg ctacgactac   600
agcagaggcc agctgatcga ggacgtggag cacaccttcg aggagatcaa gcccctgtac   660
gagcacctgc acgcctacgt gagagccaag ctgatgaacg cctaccccag ctacatcagc   720
cccatcggct gcctgcccgc ccacctgctg ggcgacatgt ggggcagatt ctggaccaac   780
ctgtacagcc tgaccgtgcc cttcggccag aagcccaaca tcgacgtgac cgacgccatg   840 gtgaccagg cctggacgc ccagagaatc ttcaaggagg ccgagaagtt cttcgtgagc   900
gtgggcctgc ccaacatgac ccagggcttc tgggagaaca gcatgctgac cgaccccggc   960
aacgtgcaga aggccgtgtg ccacccccac ggcctgggacc tgggcaaggg cgacttcaga  1020
```

```
atcctgatgt gcaccaaggt gaccatggac gacttcctga ccgcccacca cgagatgggc    1080
cacatccagt acgacatggc ctacgccgcc cagcccttcc tgctgagaaa cggcgccaac    1140
gagggcttcc accaggccgt gggcgagatc atgagcctga gcgccgccac ccccaagcac    1200
ctgaagagca tcggcctgct gagccccgac ttccaggagg acaacgagac cgagatcaac    1260
ttcctgctga gcaggccct gaccatcgtg gcaccctgc ccttcaccta catgctggag    1320
aagtggagat ggatggtgtt caagggcgag atccccaagg accagtggat gaagaagtgg    1380
tgggagatga agagagagat cgtgggcgtg gtggagcccg tgccccacga cgagacctac    1440
tgcgaccccg ccagcctgtt ccacgtgagc aacgactaca gcttcatcag atactacacc    1500
agaaccctgt accagttcca gttccaggag gccctgtgcc aggccgccaa gcacgagggc    1560
cccctgcaca gtgcgacat cagcaacagc accgaggccg ccagaagct gttcaacatg    1620 ctgagactgg gcaagagcga gccctggacc ctggccctgg agaacgtggt gggcgccaag    1680
aacatgaacg tgagacccct gctgaactac ttcgagcccc tgttccacctg gctgaaggac    1740 cagaacaaga acagcttcgt gggctggagc accgactgga gccccctacgc cgaccagagc    1800 atcaaggtga gaatcagcct gaagagcgcc ctgggcgaca aggcctacga gtggaacgac    1860
aacgagatgt acctgttcag aagcagcgtg gcctacgcca tgagacagta cttcctgaag    1920
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggccccc caaccagccc    2160 cccgtgagcg acaagaccca cctgccccc ccctgcccccg ccccgagct gctgggcggc    2220 cccagcgtgt tcctgttccc cccaagccc aaggacaccc tgatgatcag cagaaccccc    2280
gaggtgacct gcgtggtggt ggacgtgagc cacgaggacc ccgaggtgaa gttcaactgg    2340
tacgtggacg gcgtggaggt gcacaacgcc aagaccaagc ccagagagga gcagtacaac    2400
agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagccccag gtgtacaccc tgcccccag cagagacgag    2580 ctgaccaaga accaggtgag cctgacctgc ctggtgaagg gcttctaccc cagcgacatc    2640
gccgtggagt gggagagcaa cggccagccc gagaacaact acaagaccac ccccccgtg    2700 ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                     2850
```

<210> SEQ ID NO 69
<211> LENGTH: 2850
<212> TYPE: DNA
<213> ORGANISM: Artificial Sequence
<220> FEATURE:
<223> OTHER INFORMATION: Synthetic

<400> SEQUENCE: 69

```
cagagcacca tcgaggagca ggccaagacc ttcctggaca agttcaacca cgaggccgag      60
gacctgttct accagagcag cctggccagc tggaactaca acaccaacat caccgaggag     120
aacgtgcaga acatgaacaa cgccggcgac aagtggagcg ccttcctgaa ggagcagagc     180
accagcgccc agatgtaccc cctgcaggag atccagaacc tgaccgtgaa gctgcagctg     240
```

-continued

```
caggccctgc agcagaacgg cagcagcgtg ctgagcgagg acaagagcaa gagactgaac      300
accatcctga acaccatgag caccatctac agcaccggca aggtgtgcaa ccccgacaac      360
ccccaggagt gcctgctgct ggagcccggc ctgaacgaga tcatggccaa cagcctggac      420
tacaacgaga gactgtgggc ctgggagagc tggagaagcg aggtgggcaa gcagctgaga      480
cccctgtacg aggagtacgt ggtgctgaag aacgagatgg ccagagccaa ccactacgag      540
gactacggcg actactggag aggcgactac gaggtgaacg cgtggacgg ctacgactac       600 agcagaggcc agctgatcga ggacgtggag cacaccttcg aggagatcaa gccctgtac      660 gagcacctgc acgcctacgt gagagccaag ctgatgaacg cctacccag ctacatcagc      720 cccatcggct gcctgcccgc ccacctgctg ggcgacatgt ggggcagatt ctggaccaac     780
ctgtacagcc tgaccgtgcc cttcggccag aagcccaaca tcgacgtgac cgacgccatg     840
gtggaccagg cctgggacgc cagagaatc ttcaaggagg ccgagaagtt cttcgtgagc      900
gtgggcctgc caacatgac ccagggcttc tgggagctga gcatgctgac cgaccccggc      960
aacgtgcaga aggccgtgtg ccaccccacc gcctgggacc tgggcaaggg cgacttcaga   1020
atcctgatgt gcaccaaggt gaccatggac gacttcctga ccgcccacgc cgagatgggc   1080
agaatccagt acgacatggc ctacgtggcc cagcccttcc tgctgagaaa cggcgccaac   1140
gagggcttcc accaggccgt gggcgagatc atgagcctga gcgccgccac ccccaagcac   1200
ctgaagagca tcggcctgct gagccccgac ttccaggagg acaacgagac cgagatcaac   1260
ttcctgctga gcaggccct gaccatcgtg ggcaccctgc ccttcaccta catgctggag   1320
aagtggagat ggatggtgtt caagggcgag atccccaagg accagtggat gaagaagtgg   1380
tgggagatga agagagagat cgtgggcgtg gtggagcccg tgccccacga cgagacctac   1440
tgcgaccccg ccagcctgtt ccacgtgagc aacgactaca gcttcatcag atactacacc   1500
agaaccctgt accagttcca gttccaggag gccctgtgcc aggccgccaa gcacgagggc   1560
cccctgcaca agtgcgacat cagcaacagc accgaggccg ccagaagct gttcaacatg   1620 ctgagactgg gcaagagcga gccctggacc ctggccctgg agaacgtggt gggcgccaag   1680
aacatgaacg tgagacccct gctgaactac ttcgagcccc tgttcacctg gctgaaggac   1740
cagaacaaga acagcttcgt gggctggagc accgactgga gccccctacg cgaccagagc   1800
atcaaggtga gaatcagcct gaagagcgcc ctgggcgaca aggcctacga gtggaacgac   1860
aacgagatgt acctgttcag aagcagcgtg gcctacgcca tgagacagta cttcctgaag   1920
gtgaagaacc agatgatcct gttcggcgag gaggacgtga gagtggccaa cctgaagccc   1980
agaatcagct tcaacttctt cgtgaccgcc cccaagaacg tgagcgacat catccccaga   2040
accgaggtgg agaaggccat cagaatgagc agaagcagaa tcaacgacgc cttcagactg   2100
aacgacaaca gcctggagtt cctgggcatc cagcccaccc tgggcccccc caaccagccc   2160
cccgtgagca caagaccca cacctgcccc cctgcccccg cccccgagct gctgggcggc   2220
cccagcgtgt tcctgttccc ccccaagccc aaggacaccc tgatgatcag cagaacccc   2280 gaggtgacct gcgtggtggt ggacgtgagc cacgaggacc ccgaggtgaa gttcaactgg   2340
tacgtggacg gcgtggaggt gcacaacgcc aagaccaagc cagagagga gcagtacaac   2400 agcacctaca gagtggtgag cgtgctgacc gtgctgcacc aggactggct gaacggcaag   2460
gagtacaagt gcaaggtgag caacaaggcc ctgcccgccc ccatcgagaa gaccatcagc   2520
aaggccaagg gccagcccag agagcccag gtgtacaccc tgcccccag cagagacgag   2580
```

| | |
|---|---|
| ctgaccaaga accaggtgag cctgacctgc ctggtgaagg gcttctaccc cagcgacatc | 2640 |
| gccgtggagt gggagagcaa cggccagccc gagaacaact acaagaccac ccccccgtg | 2700 |
| ctggacagcg acggcagctt cttcctgtac agcaagctga ccgtggacaa gagcagatgg | 2760 |
| cagcagggca cgtgttcag ctgcagcgtg atgcacgagg ccctgcacaa ccactacacc | 2820 |
| cagaagagcc tgagcctgag ccccggctga | 2850 |

<210> SEQ ID NO 70
<211> LENGTH: 2850
<212> TYPE: DNA
<213> ORGANISM: Artificial Sequence
<220> FEATURE:
<223> OTHER INFORMATION: Synthetic

<400> SEQUENCE: 70

| | |
|---|---|
| cagagcacca tcgaggagca ggccaagacc ttcctggaca agttcaacca cgaggccgag | 60 |
| gacctgttct accagagcag cctggccagc tggaactaca acaccaacat caccgaggag | 120 |
| aacgtgcaga acatgaacaa cgccggcgac aagtggagcg ccttcctgaa ggagcagagc | 180 |
| accctggccc agatgtaccc cctgcaggag atccagaacc tgaccgtgaa gctgcagctg | 240 |
| caggccctgc agcagaacgg cagcagcgtg ctgagcgagc acaagagcaa gagactgaac | 300 |
| accatcctga acaccatgag caccatctac agcaccggca aggtgtgcaa ccccgacaac | 360 |
| ccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctacccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagctga cgcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacgc cgagatgggc | 1080 |
| agaatccagt acgacatggc ctacgtggcc cagcccttcc tgctgagaaa cggcgccaac | 1140 |
| gagggcttcc accaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg ggcaccctgc ccttcaccta catgctggag | 1320 |
| aagtggagat ggatggtgtt caagggcgag atccccaagg accagtggat gaagaagtgg | 1380 |
| tgggagatga agagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca agtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagaccct gctgaactac ttcgagcccc tgttcacctg gctgaaggac | 1740 |
| cagaacaaga acagcttcgt gggctggagc accgactgga gccccctacgc cgaccagagc | 1800 |

```
atcaaggtga gaatcagcct gaagagcgcc ctgggcgaca aggcctacga gtggaacgac    1860
aacgagatgt acctgttcag aagcagcgtg gcctacgcca tgagacagta cttcctgaag    1920
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggcccccc caaccagccc    2160
cccgtgagcg acaagaccca cacctgcccc cctgccccg ccccgagct gctgggcggc    2220 cccagcgtgt tcctgttccc ccccaagccc aaggacaccc tgatgatcag cagaaccccc    2280
gaggtgacct gcgtggtggt ggacgtgagc cacgaggacc ccgaggtgaa gttcaactgg    2340
tacgtggacg gcgtggaggt gcacaacgcc aagaccaagc cagagagga gcagtacaac    2400 agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagcccag gtgtacaccc tgcccccag cagagacgag    2580 ctgaccaaga accaggtgag cctgacctgc ctggtgaagg gcttctaccc cagcgacatc    2640
gccgtggagt gggagagcaa cggccagccc gagaacaact acaagaccac cccccccgtg    2700
ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                    2850
```

<210> SEQ ID NO 71
<211> LENGTH: 2850
<212> TYPE: DNA
<213> ORGANISM: Artificial Sequence
<220> FEATURE:
<223> OTHER INFORMATION: Synthetic

<400> SEQUENCE: 71

```
cagagcacca tcgaggagca ggccaagtac ttcctggaca gttcaacca cgaggccgag      60 gacctgttct accagagcag cctggccagc tggaactaca caccaacat caccgaggag    120 aacgtgcaga acatgaacaa cgccggcgac aagtggagcg ccttcctgaa ggagcagagc    180
accagcgccc agatgtaccc cctgcaggag atccagaacc tgaccgtgaa gctgcagctg    240
caggccctgc agcagaacgg cagcagcgtg ctgagcgagg acaagagcaa gagactgaac    300
accatcctga caccatgag caccatctac agcaccggca aggtgtgcaa ccccgacaac    360
ccccaggagt gcctgctgct ggagcccggc ctgaacgaga tcatggccaa cagcctggac    420
tacaacgaga gactgtgggc ctgggagagc tggagaagcg aggtgggcaa gcagctgaga    480
cccctgtacg aggagtacgt ggtgctgaag aacgagatgg ccagagccaa ccactacgag    540
gactacggcg actactggag aggcgactac gaggtgaacg gcgtggacgg ctacgactac    600
agcagaggcc agctgatcga ggacgtggag cacaccttcg aggagatcaa gcccctgtac    660
gagcacctgc acgcctacgt gagagccaag ctgatgaacg cctacccag ctacatcagc    720 cccatcggct gcctgcccgc ccacctgctg ggcgacatgt ggggcagatt ctggaccaac    780
ctgtacagcc tgaccgtgcc cttcggccag aagcccaaca tcgacgtgac cgacgccatg    840
gtggaccagg cctgggacgc ccagagaatc ttcaaggagg ccgagaagtt cttcgtgagc    900
gtgggcctgc ccaacatgac ccagggcttc tgggagttca catgctgac cgaccccggc    960
```

```
aacgtgcaga aggccgtgtg ccaccccacc gcctgggacc tgggcaaggg cgacttcaga    1020
atcctgatgt gcaccaaggt gaccatggac gacttcctga ccgcccacgc cgagatgggc    1080
cacatccagt acgacatggc ctacgccctg cagcccttcc tgctgagaaa cggcgccaac    1140
gagggcttcc accaggccgt gggcgagatc atgagcctga cgccgccac ccccaagcac     1200 ctgaagagca tcggcctgct gagccccgac ttccaggagg acaacgagac cgagatcaac    1260
ttcctgctga gcaggccct gaccatcgtg gcaccctgc ccttcaccta catgctggag      1320
aagtggagat ggatggtgtt caagggcgag atccccaagg accagtggat gaagaagtgg    1380
tgggagatga agagagagat cgtgggcgtg gtggagcccg tgccccacga cgagacctac    1440
tgcgaccccg ccagcctgtt ccacgtgagc aacgactaca gcttcatcag atactacacc    1500
agaaccctgt accagttcca gttccaggag gccctgtgcc aggccgccaa gcacgagggc    1560
cccctgcaca agtgcgacat cagcaacagc accgaggccg ccagaagct gttcaacatg     1620 ctgagactgg gcaagagcga gccctggacc ctggccctgg agaacgtggt gggcgccaag    1680
aacatgaacg tgagaccct gctgaactac ttcgagcccc tgttcacctg gctgaaggac     1740
cagaacaaga cagcttcgt gggctggagc accgactgga gccctacgc gaccagagc       1800 atcaaggtga gaatcagcct gaagagcgcc ctgggcgaca aggcctacga gtggaacgac    1860
aacgagatgt acctgttcag aagcagcgtg gcctacgcca tgagacagta cttcctgaag    1920
gtgaagaacc agatgatcct gttcggcgag gaggacgtga gagtggccaa cctgaagccc   1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggcccccc caaccagccc    2160
cccgtgagcg acaagaccca cacctgcccc cctgccccg cccccgagct gctgggcggc     2220
cccagcgtgt tcctgttccc ccccaagccc aaggacaccc tgatgatcag cagaaccccc   2280
gaggtgacct gcgtggtggt ggacgtgagc cacgaggacc ccgaggtgaa gttcaactgg    2340
tacgtggacg gcgtggaggt gcacaacgcc aagaccaagc ccagagagga gcagtacaac    2400
agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagcccag gtgtacaccc tgcccccag cagagacgag      2580 ctgaccaaga accaggtgag cctgacctgc ctggtgaagg gcttctaccc cagcgacatc    2640
gccgtggagt gggagagcaa cggccagccc gagaacaact acaagaccac ccccccgtg     2700 ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                     2850
```

```
<210> SEQ ID NO 72
<211> LENGTH: 2850
<212> TYPE: DNA
<213> ORGANISM: Artificial Sequence
<220> FEATURE:
<223> OTHER INFORMATION: Synthetic

<400> SEQUENCE: 72
cagagcacca tcgaggagca ggccaagtac ttcctggaca agttcaacca cgaggccgag      60
gacctgttct accagagcag cctggccagc tggaactaca caccaacat caccgaggag     120 aacgtgcaga acatgaacaa cgccggcgac aagtggagcg ccttcctgaa ggagcagagc    180
```

-continued

| | |
|---|---|
| accagcgccc agatgtaccc cctgcaggag atccagaacc tgaccgtgaa gctgcagctg | 240 |
| caggccctgc agcagaacgg cagcagcgtg ctgagcgagg acaagagcaa gagactgaac | 300 |
| accatcctga acaccatgag caccatctac agcaccggca aggtgtgcaa ccccgacaac | 360 |
| ccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctacccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagttca gcatgctgac cgaccccggc | 960 |
| aacgtgcaga aggccgtgtg ccaccccacc gcctgggacc tggcaagggg cgacttcaga | 1020 |
| atcctgatgt gcaccaaggt gaccatggac gacttcctga ccgcccacgc cgagatgggc | 1080 |
| agaatccagt acgacatggc ctacgccctg cagcccttcc tgctgagaaa cggcgccaac | 1140 |
| gagggcttcc accaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga gcaggccct gaccatcgtg ggcaccctgc ccttcaccta catgctggag | 1320 |
| aagtggagat ggatggtgtt caagggcgag atccccaagg accagtggat gaagaagtgg | 1380 |
| tgggagatga agagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca gtgcgacat cagcaacagc accgaggccg ccagaagct gttcaacatg | 1620 |
| ctgagactgg gcaagagcga gccctggacc ctggccctgg agaacgtggt gggcgccaag | 1680 |
| aacatgaacg tgagaccct gctgaactac ttcgagcccc tgttcacctg gctgaaggac | 1740 |
| cagaacaaga cagcttcgt gggctggagc accgactgga cccctacgc cgaccagagc | 1800 |
| atcaaggtga gaatcagcct gaagagcgcc ctgggcgaca aggcctacga gtggaacgac | 1860 |
| aacgagatgt acctgttcag aagcagcgtg gcctacgcca tgagacagta cttcctgaag | 1920 |
| gtgaagaacc agatgatcct gttcggcgag gaggacgtga gtggccaa cctgaagccc | 1980 |
| agaatcagct tcaacttctt cgtgaccgcc cccaagaacg tgagcgacat catccccaga | 2040 |
| accgaggtgg agaaggccat cagaatgagc agaagcagaa tcaacgacgc cttcagactg | 2100 |
| aacgacaaca gcctggagtt cctgggcatc cagcccaccc tgggcccccc caaccagccc | 2160 |
| cccgtgagcg acaagaccca cctgccccc cctgccccg ccccgagct gctgggcggc | 2220 |
| cccagcgtgt tcctgttccc ccccaagccc aaggacaccc tgatgatcag cagaaccccc | 2280 |
| gaggtgacct gcgtggtggt ggacgtgagc cacgaggacc ccgaggtgaa gttcaactgg | 2340 |
| tacgtggacg gcgtggaggt gcacaacgcc aagaccaagc ccagagagga gcagtacaac | 2400 |
| agcacctaca gagtggtgag cgtgctgacc gtgctgcacc aggactggct gaacggcaag | 2460 |
| gagtacaagt gcaaggtgag caacaaggcc ctgcccgccc ccatcgagaa gaccatcagc | 2520 |

| | | | |
|---|---|---|---|
| aaggccaagg | gccagcccag | agagccccag | gtgtacaccc tgccccccag cagagacgag | 2580 |
| ctgaccaaga | accaggtgag | cctgacctgc | ctggtgaagg gcttctaccc cagcgacatc | 2640 |
| gccgtggagt | gggagagcaa | cggccagccc | gagaacaact acaagaccac cccccccgtg | 2700 |
| ctggacagcg | acggcagctt | cttcctgtac | agcaagctga ccgtggacaa gagcagatgg | 2760 |
| cagcagggca | acgtgttcag | ctgcagcgtg | atgcacgagg ccctgcacaa ccactacacc | 2820 |
| cagaagagcc | tgagcctgag | ccccggctga | | 2850 |

```
<210> SEQ ID NO 73
<211> LENGTH: 2850
<212> TYPE: DNA
<213> ORGANISM: Artificial Sequence
<220> FEATURE:
<223> OTHER INFORMATION: Synthetic

<400> SEQUENCE: 73
```

| | | | | |
|---|---|---|---|---|
| cagagcacca | tcgaggagca | ggccaagacc | ttcctggaca agttcaacca cgaggccgag | 60 |
| gacctgttct | accagagcag | cctggccagc | tggaactaca acaccaacat caccgaggag | 120 |
| aacgtgcaga | acatgaacaa | cgccggcgac | aagtggagcg ccttcctgaa ggagcagagc | 180 |
| accctggccc | agatgtaccc | cctgcaggag | atccagaacc tgaccgtgaa gctgcagctg | 240 |
| caggccctgc | agcagaacgg | cagcagcgtg | ctgagcgagg acaagagcaa gagactgaac | 300 |
| accatcctga | acaccatgag | caccatctac | agcaccggca aggtgtgcaa ccccgacaac | 360 |
| ccccaggagt | gcctgctgct | ggagcccggc | ctgaacgaga tcatggccaa cagcctggac | 420 |
| tacaacgaga | gactgtgggc | ctgggagagc | tggagaagcg aggtgggcaa gcagctgaga | 480 |
| cccctgtacg | aggagtacgt | ggtgctgaag | aacgagatgg ccagagccaa ccactacgag | 540 |
| gactacggcg | actactggag | aggcgactac | gaggtgaacg gcgtggacgg ctacgactac | 600 |
| agcagaggcc | agctgatcga | ggacgtggag | cacaccttcg aggagatcaa gcccctgtac | 660 |
| gagcacctgc | acgcctacgt | gagagccaag | ctgatgaacg cctacccag ctacatcagc | 720 |
| cccatcggct | gcctgcccgc | ccacctgctg | ggcgacatgt ggggcagatt ctggaccaac | 780 |
| ctgtacagcc | tgaccgtgcc | cttcggccag | aagcccaaca tcgacgtgac cgacgccatg | 840 |
| gtggaccagg | cctgggacgc | ccagagaatc | ttcaaggagg ccgagaagtt cttcgtgagc | 900 |
| gtgggcctgc | ccaacatgac | ccagggcttc | tgggagaaca gcatgctgac cgaccccggc | 960 |
| aacgtgcaga | aggccgtgtg | ccaccccacc | gcctgggacc tgggcaaggg cgacttcaga | 1020 |
| atcctgatgt | gcaccaaggt | gaccatggac | gacttcctga ccgcccacgc cgagatgggc | 1080 |
| gccatccagt | acgacatggc | ctacgccctg | cagcccttcc tgctgagaaa cggcgccaac | 1140 |
| gagggcttcc | accaggccgt | gggcgagatc | atgagcctga cgccgccac ccccaagcac | 1200 |
| ctgaagagca | tcggcctgct | gagccccgac | ttccaggagg acaacgagac cgagatcaac | 1260 |
| ttcctgctga | agcaggccct | gaccatcgtg | ggcaccctgc ccttcaccta catgctggag | 1320 |
| aagtggagat | ggatggtgtt | caagggcgag | atccccaagg accagtggat gaagaagtgg | 1380 |
| tgggagatga | agagagagat | cgtgggcgtg | gtggagcccg tgccccacga cgagacctac | 1440 |
| tgcgaccccg | ccagcctgtt | ccacgtgagc | aacgactaca gcttcatcag atactacacc | 1500 |
| agaaccctgt | accagttcca | gttccaggag | gccctgtgcc aggccgccaa gcacgagggc | 1560 |
| cccctgcaca | agtgcgacat | cagcaacagc | accgaggccg ccagaagct gttcaacatg | 1620 |
| ctgagactgg | gcaagagcga | gccctggacc | ctggccctgg agaacgtggt gggcgccaag | 1680 |
| aacatgaacg | tgagacccct | gctgaactac | ttcgagcccc tgttcacctg gctgaaggac | 1740 |

```
cagaacaaga acagcttcgt gggctggagc accgactgga gcccctacgc cgaccagagc    1800
atcaaggtga gaatcagcct gaagagcgcc ctgggcgaca aggcctacga gtggaacgac    1860
aacgagatgt acctgttcag aagcagcgtg gcctacgcca tgagacagta cttcctgaag    1920
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggccccc caaccagccc    2160 cccgtgagcg acaagaccca cacctgcccc cctgccccg ccccgagct gctgggcggc    2220 cccagcgtgt tcctgttccc ccccaagccc aaggacaccc tgatgatcag cagaaccccc    2280
gaggtgacct gcgtggtggt ggacgtgagc cacgaggacc ccgaggtgaa gttcaactgg    2340
tacgtggacg gcgtggaggt gcacaacgcc aagaccaagc ccagagagga gcagtacaac    2400
agcacctaca gagtggtgag cgtgctgacc gtgctgcacc aggactggct gaacggcaag    2460
gagtacaagt gcaaggtgag caacaaggcc ctgcccgccc ccatcgagaa gaccatcagc    2520
aaggccaagg gccagcccag agagcccag gtgtacaccc tgccccccag cagagacgag    2580
ctgaccaaga accaggtgag cctgacctgc ctggtgaagg gcttctaccc cagcgacatc    2640
gccgtggagt gggagagcaa cggccagccc gagaacaact acaagaccac cccccccgtg    2700
ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                     2850
```

<210> SEQ ID NO 74
<211> LENGTH: 2850
<212> TYPE: DNA
<213> ORGANISM: Artificial Sequence
<220> FEATURE:
<223> OTHER INFORMATION: Synthetic

<400> SEQUENCE: 74

```
cagagcacca tcgaggagca ggccaagacc ttcctggaca agttcaacca cgaggccgag      60
gacctgttct accagagcag cctggccagc tggaactaca acaccaacat caccgaggag     120
aacgtgcaga acatgaacaa cgccggcgac aagtggagcg ccttcctgaa ggagcagagc     180
accctggccc cagatgtaccc cctgcaggag atccagaacc tgaccgtgaa gctgcagctg     240 cagggccctgc agcagaacgg cagcagcgtg ctgagcgagg acaagagcaa gagactgaac     300
accatcctga acaccatgag caccatctac agcaccggca aggtgtgcaa ccccgacaac     360
ccccaggagt gcctgctgct ggagcccggc ctgaacgaga tcatggccaa cagcctggac     420
tacaacgaga gactgtgggc ctgggagagc tggagaagcg aggtgggcaa gcagctgaga     480
cccctgtacg aggagtacgt ggtgctgaag aacgagatgg ccagagccaa ccactacgag     540
gactacggcg actactggag aggcgactac gaggtgaacg gcgtggacgg ctacgactac     600
agcagaggcc agctgatcga ggacgtggag cacaccttcg aggagatcaa gcccctgtac     660
gagcacctgc acgcctacgt gagagccaag ctgatgaacg cctaccccag ctacatcagc     720
cccatcggct gcctgcccgc ccacctgctg ggcgacatgt ggggcagatt ctggaccaac     780
ctgtacagcc tgaccgtgcc cttcggccag aagcccaaca tcgacgtgac cgacgccatg     840
gtggaccagg cctgggacgc ccagagaatc ttcaaggagg ccgagaagtt cttcgtgagc     900
```

```
gtgggcctgc ccaacatgac ccagggcttc tgggagaaca gcatgctgac cgaccccggc    960
aacgtgcaga aggccgtgtg ccaccccacc gcctgggacc tgggcaaggg cgacttcaga   1020
atcctgatgt gcaccaaggt gaccatggac gacttcctga ccgcccacgc cgagatgggc   1080
agaatccagt acgacatggc ctacgccctg cagcccttcc tgctgagaaa cggcgccaac   1140
gagggcttcc accaggccgt gggcgagatc atgagcctga gcgccgccac ccccaagcac   1200
ctgaagagca tcggcctgct gagccccgac ttccaggagg acaacgagac cgagatcaac   1260
ttcctgctga agcaggccct gaccatcgtg ggcaccctgc ccttcaccta catgctggag   1320
aagtggagat ggatggtgtt caagggcgag atccccaagg accagtggat gaagaagtgg   1380
tgggagatga agagagagat cgtgggcgtg gtggagcccg tgccccacga cgagacctac   1440
tgcgaccccg ccagcctgtt ccacgtgagc aacgactaca gcttcatcag atactacacc   1500
agaaccctgt accagttcca gttccaggag gccctgtgcc aggccgccaa gcacgagggc   1560
cccctgcaca agtgcgacat cagcaacagc accgaggccg ccagaagct gttcaacatg   1620
ctgagactgg gcaagagcga gccctggacc ctggccctgg agaacgtggt gggcgccaag   1680
aacatgaacg tgagacccct gctgaactac ttcgagcccc tgttccacct gctgaaggac   1740
cagaacaaga acagcttcgt gggctggagc accgactgga cccctacgc cgaccagagc   1800
atcaaggtga gaatcagcct gaagagcgcc ctgggcgaca aggcctacga gtggaacgac   1860
aacgagatgt acctgttcag aagcagcgtg gcctacgcca tgagacagta cttcctgaag   1920
gtgaagaacc agatgatcct gttcggcgag gaggacgtga gagtggccaa cctgaagccc   1980
agaatcagct tcaacttctt cgtgaccgcc cccaagaacg tgagcgacat catccccaga   2040
accgaggtgg agaaggccat cagaatgagc agaagcagaa tcaacgacgc cttcagactg   2100
aacgacaaca gcctggagtt cctgggcatc cagcccaccc tgggcccccc caaccagccc   2160
cccgtgagcg acaagaccca cctgccccc cctgcccg ccccgagct gctgggcggc   2220
cccagcgtgt cctgttccc ccccaagccc aaggacaccc tgatgatcag cagaacccc   2280
gaggtgacct gcgtggtggt ggacgtgagc cacgaggacc ccgaggtgaa gttcaactgg   2340
tacgtggacg gcgtggaggt gcacaacgcc aagaccaagc cagagagga gcagtacaac   2400
agcacctaca gagtggtgag cgtgctgacc gtgctgcacc aggactggct gaacggcaag   2460
gagtacaagt gcaaggtgag caacaaggcc ctgcccgccc catcgagaa gaccatcagc   2520
aaggccaagg ccagcccag agagcccag gtgtacaccc tgcccccag cagagacgag   2580
ctgaccaaga accaggtgag cctgacctgc ctggtgaagg gcttctaccc cagcgacatc   2640
gccgtggagt gggagagcaa cggccagccc gagaacaact acaagaccac ccccccgtg   2700
ctggacagcg acggcagctt cttcctgtac agcaagctga ccgtggacaa gagcagatgg   2760
cagcagggca acgtgttcag ctgcagcgtg atgcacgagg ccctgcacaa ccactacacc   2820
cagaagagcc tgagcctgag ccccggctga                                    2850
```

<210> SEQ ID NO 75
<211> LENGTH: 2850
<212> TYPE: DNA
<213> ORGANISM: Artificial Sequence
<220> FEATURE:
<223> OTHER INFORMATION: Synthetic

<400> SEQUENCE: 75

```
cagagcacca tcgaggagca ggccaagacc ttcctggaca agttcaacca cgaggccgag     60
gacctgttct accagagcag cctggccagc tggaactaca acaccaacat caccgaggag    120
```

```
aacgtgcaga acatgaacaa cgccggcgac aagtggagcg ccttcctgaa ggagcagagc    180
accctggccc agatgtaccc cctgcaggag atccagaacc tgaccgtgaa gctgcagctg    240
caggccctgc agcagaacgg cagcagcgtg ctgagcgagg acaagagcaa gagactgaac    300
accatcctga acaccatgag caccatctac agcaccggca aggtgtgcaa ccccgacaac    360
ccccaggagt gcctgctgct ggagcccggc ctgaacgaga tcatggccaa cagcctggac    420
tacaacgaga gactgtgggc ctgggagagc tggagaagcg aggtgggcaa gcagctgaga    480
cccctgtacg aggagtacgt ggtgctgaag aacgagatgg ccagagccaa ccactacgag    540
gactacggcg actactggag aggcgactac gaggtgaacg gcgtggacgg ctacgactac    600
agcagaggcc agctgatcga ggacgtggag cacaccttcg aggagatcaa gcccctgtac    660
gagcacctgc acgcctacgt gagagccaag ctgatgaacg cctacccag ctacatcagc    720 cccatcggct gcctgcccgc ccacctgctg ggcgacatgt ggggcagatt ctggaccaac    780
ctgtacagcc tgaccgtgcc cttcggccag aagcccaaca tcgacgtgac cgacgccatg    840
gtggaccagg cctgggacgc ccagagaatc ttcaaggagg ccgagaagtt cttcgtgagc    900
gtgggcctgc ccaacatgac ccagggcttc tgggagaaca gcatgctgac cgaccccggc    960
aacgtgcaga aggccgtgtg ccacccacc gcctgggacc tgggcaaggg cgacttcaga   1020
atcctgatgt gcaccaaggt gaccatggac gacttcctga ccgcccacct ggagatgggc   1080
cacatccagt acgacatggc ctacgccctg cagcccttcc tgctgagaaa cggcgccaac   1140
gagggcttcc accaggccgt gggcgagatc atgagcctga cgccgccac ccccaagcac   1200 ctgaagagca tcggcctgct gagccccgac ttccaggagg acaacgagac cgagatcaac   1260
ttcctgctga gcaggccct gaccatcgtg ggcaccctgc ccttcaccta catgctggag   1320
aagtggagat ggatggtgtt caagggcgag atccccaagg accagtggat gaagaagtgg   1380
tgggagatga agagagagat cgtgggcgtg gtggagcccg tgccccacga cgagacctac   1440 tgcgacccg ccagcctgtt ccacgtgagc aacgactaca gcttcatcag atactacacc   1500
agaaccctgt accagttcca gttccaggag gccctgtgcc aggccgccaa gcacgagggc   1560
cccctgcaca agtgcgacat cagcaacagc accgaggccg ccagaagct gttcaacatg   1620 ctgagactgg gcaagagcga gccctggacc ctggccctgg agaacgtggt gggcgccaag   1680
aacatgaacg tgagacccct gctgaactac ttcgagcccc tgttcacctg gctgaaggac   1740
cagaacaaga cagcttcgt gggctggagc accgactgga gccctacgc cgaccagagc   1800 atcaaggtga gaatcagcct gaagagcgcc ctgggcgaca aggcctacga gtggaacgac   1860
aacgagatgt acctgttcag aagcagcgtg gcctacgcca tgagacagta cttcctgaag   1920
gtgaagaacc agatgatcct gttcggcgag gaggacgtga gagtggccaa cctgaagccc   1980
agaatcagct tcaacttctt cgtgaccgcc cccaagaacg tgagcgacat catccccaga   2040
accgaggtgg agaaggccat cagaatgagc agaagcagaa tcaacgacgc cttcagactg   2100
aacgacaaca gcctggagtt cctgggcatc cagcccaccc tgggcccccc caaccagccc   2160
cccgtgagcg acaagaccca cctgcccc cctgccccg ccccgagct gctgggcggc   2220 cccagcgtgt tcctgttccc ccccaagccc aaggacaccc tgatgatcag cagaacccc   2280 gaggtgacct gcgtggtggt ggacgtgagc cacgaggacc ccgaggtgaa gttcaactgg   2340
tacgtggacg gcgtggaggt gcacaacgcc aagaccaagc ccagagagga gcagtacaac   2400
agcacctaca gagtggtgag cgtgctgacc gtgctgcacc aggactggct gaacggcaag   2460
```

| | |
|---|---:|
| gagtacaagt gcaaggtgag caacaaggcc ctgcccgccc ccatcgagaa gaccatcagc | 2520 |
| aaggccaagg gccagcccag agagcccag gtgtacaccc tgcccccag cagagacgag | 2580 |
| ctgaccaaga accaggtgag cctgacctgc ctggtgaagg gcttctaccc cagcgacatc | 2640 |
| gccgtggagt gggagagcaa cggccagccc gagaacaact acaagaccac ccccccgtg | 2700 |
| ctggacagcg acggcagctt cttcctgtac agcaagctga ccgtggacaa gagcagatgg | 2760 |
| cagcagggca acgtgttcag ctgcagcgtg atgcacgagg ccctgcacaa ccactacacc | 2820 |
| cagaagagcc tgagcctgag ccccggctga | 2850 |

<210> SEQ ID NO 76
<211> LENGTH: 2850
<212> TYPE: DNA
<213> ORGANISM: Artificial Sequence
<220> FEATURE:
<223> OTHER INFORMATION: Synthetic

<400> SEQUENCE: 76

| | |
|---|---:|
| cagagcacca tcgaggagca ggccagaacc ttcctggaca agttcaacca cgaggccgag | 60 |
| gacctgttct accagagcag cctggccagc tggaactaca acaccaacat caccgaggag | 120 |
| aacgtgcaga acatgaacaa cgccggcgac aagtggagcg ccttcctgaa ggagcagagc | 180 |
| accctggccc agatgtaccc cctgcaggag atccagaacc tgaccgtgaa gctgcagctg | 240 |
| caggccctgc agcagaacgg cagcagcgtg ctgagcgagg acaagagcaa gagactgaac | 300 |
| accatcctga acaccatgag caccatctac agcaccggca aggtgtgcaa ccccgacaac | 360 |
| cccccaggagt gcctgctgct ggagcccggc ctgaacgaga tcatggccaa cagcctggac | 420 |
| tacaacgaga gactgtgggc ctgggagagc tggagaagcg aggtgggcaa gcagctgaga | 480 |
| cccctgtacg aggagtacgt ggtgctgaag aacgagatgg ccagagccaa ccactacgag | 540 |
| gactacggcg actactggag aggcgactac gaggtgaacg gcgtggacgg ctacgactac | 600 |
| agcagaggcc agctgatcga ggacgtggag cacaccttcg aggagatcaa gcccctgtac | 660 |
| gagcacctgc acgcctacgt gagagccaag ctgatgaacg cctaccccag ctacatcagc | 720 |
| cccatcggct gcctgcccgc ccacctgctg ggcgacatgt ggggcagatt ctggaccaac | 780 |
| ctgtacagcc tgaccgtgcc cttcggccag aagcccaaca tcgacgtgac cgacgccatg | 840 |
| gtggaccagg cctgggacgc ccagagaatc ttcaaggagg ccgagaagtt cttcgtgagc | 900 |
| gtgggcctgc ccaacatgac ccagggcttc tgggagaaca gcatgctgac cgaccccggc | 960 |
| aacgtgcaga aggccgtgtg ccaccccacc gcctgggacc tgggcaaggg cgacttcaga | 1020 |
| atcctgatgt gcaccaaggt gaccatggac gacttcctga ccgcccacgc cgagatgggc | 1080 |
| cacatccagt acgacatggc ctacgccctg cagcccttcc tgctgagaaa cggcgccaac | 1140 |
| gagggcttcc accaggccgt gggcgagatc atgagcctga gcgccgccac ccccaagcac | 1200 |
| ctgaagagca tcggcctgct gagccccgac ttccaggagg acaacgagac cgagatcaac | 1260 |
| ttcctgctga agcaggccct gaccatcgtg ggcacccctgc ccttcaccta catgctggag | 1320 |
| aagtggagat ggatggtgtt caagggcgag atccccaagg accagtggat gaagaagtgg | 1380 |
| tgggagatga gagagagat cgtgggcgtg gtggagcccg tgccccacga cgagacctac | 1440 |
| tgcgaccccg ccagcctgtt ccacgtgagc aacgactaca gcttcatcag atactacacc | 1500 |
| agaaccctgt accagttcca gttccaggag gccctgtgcc aggccgccaa gcacgagggc | 1560 |
| cccctgcaca gtgcgacat cagcaacagc accgaggccg ccagaagct gttcaacatg | 1620 |
| ctgagactgg gcaagagcga gccctggacc ctggcctgg agaacgtggt gggcgccaag | 1680 |

```
aacatgaacg tgagacccct gctgaactac ttcgagcccc tgttcacctg gctgaaggac    1740
cagaacaaga acagcttcgt gggctggagc accgactgga gccctacgc cgaccagagc    1800 atcaaggtga gaatcagcct gaagagcgcc ctgggcgaca aggcctacga gtggaacgac    1860
aacgagatgt acctgttcag aagcagcgtg gcctacgcca tgagacagta cttcctgaag    1920
gtgaagaacc agatgatcct gttcggcgag gaggacgtga gagtggccaa cctgaagccc    1980
agaatcagct tcaacttctt cgtgaccgcc cccaagaacg tgagcgacat catccccaga    2040
accgaggtgg agaaggccat cagaatgagc agaagcagaa tcaacgacgc cttcagactg    2100
aacgacaaca gcctggagtt cctgggcatc cagcccaccc tgggcccccc caaccagccc    2160
cccgtgagcg acaagaccca cacctgcccc cctgccccg ccccgagct gctgggcggc    2220 cccagcgtgt tcctgttccc ccccaagccc aaggacaccc tgatgatcag cagaaccccc    2280
gaggtgacct gcgtggtggt ggacgtgagc cacgaggacc ccgaggtgaa gttcaactgg    2340
tacgtggacg gcgtggaggt gcacaacgcc aagaccaagc cagagagga gcagtacaac    2400 agcacctaca gagtggtgag cgtgctgacc gtgctgcacc aggactggct gaacggcaag    2460
gagtacaagt gcaaggtgag caacaaggcc ctgcccgccc catcgagaa gaccatcagc    2520 aaggccaagg gccagcccag agagcccag gtgtacaccc tgcccccag cagagacgag    2580 ctgaccaaga accaggtgag cctgacctgc tggtgaagg gcttctaccc cagcgacatc    2640
gccgtggagt gggagagcaa cggccagccc gagaacaact acaagaccac cccccccgtg    2700
ctggacagcg acggcagctt cttcctgtac agcaagctga ccgtggacaa gagcagatgg    2760
cagcagggca acgtgttcag ctgcagcgtg atgcacgagg ccctgcacaa ccactacacc    2820
cagaagagcc tgagcctgag ccccggctga                                    2850
```

<210> SEQ ID NO 77
<211> LENGTH: 2850
<212> TYPE: DNA
<213> ORGANISM: Artificial Sequence
<220> FEATURE:
<223> OTHER INFORMATION: Synthetic

<400> SEQUENCE: 77

```
cagagcacca tcgaggagca ggccaagacc ttcctggaca agttcaacca cgaggccgag      60
gacctgttct accagagcag cctggccagc tggaactaca caccaacat caccgaggag     120 aacgtgcaga acatgaacaa cgccggcgac aagtggagcg ccttcctgaa ggagcagagc    180
accctggccc agatgtaccc cctgcaggag atccagaacc tgaccgtgaa gctgcagctg    240
caggccctgc agcagaacgg cagcagcgtg ctgagcgagg acaagagcaa gagactgaac    300
accatcctga acaccatgag caccatctac agcaccggca aggtgtgcaa cccgacaac    360 ccccaggagt gcctgctgct ggagcccggc ctgaacgaga tcatggccaa cagcctggac    420
tacaacgaga gactgtgggc ctgggagagc tggagaagcg aggtgggcaa gcagctgaga    480
cccctgtacg aggagtacgt ggtgctgaag aacgagatgg ccagagccaa ccactacgag    540
gactacggcg actactggag aggcgactac gaggtgaacg gcgtggacgg ctacgactac    600
agcagaggcc agctgatcga ggacgtggag cacaccttcg aggagatcaa gcccctgtac    660
gagcacctgc acgcctacgt gagagcaag ctgatgaacg cctaccccag ctacatcagc    720
cccatcggct gcctgcccgc ccacctgctg ggcgacatgt ggggcagatt ctggaccaac    780
ctgtacagcc tgaccgtgcc cttcggccag aagcccaaca tcgacgtgac cgacgccatg    840
```

```
gtggaccagg cctgggacgc ccagagaatc ttcaaggagg ccgagaagtt cttcgtgagc      900
gtgggcctgc ccaacatgac ccagggcttc tgggagaaca gcatgctgac cgaccccggc      960
aacgtgcaga aggccgtgtg ccaccccacc gcctgggacc tgggcaaggg cgacttcaga     1020
atcctgatgt gcaccaaggt gaccatggac gacttcctga ccgcccacct ggagatgggc     1080
agaatccagt acgacatggc ctacgccctg cagcccttcc tgctgagaaa cggcgccaac     1140
gagggcttcc accaggccgt gggcgagatc atgagcctga cgccgccac ccccaagcac      1200
ctgaagagca tcggcctgct gagccccgac ttccaggagg acaacgagac cgagatcaac     1260
ttcctgctga gcaggccct gaccatcgtg ggcaccctgc ccttcaccta catgctggag      1320
aagtggagat ggatggtgtt caagggcgag atccccaagg accagtggat gaagaagtgg     1380
tgggagatga agagagagat cgtgggcgtg gtggagcccg tgccccacga cgagacctac     1440
tgcgacccg ccagcctgtt ccacgtgagc aacgactaca gcttcatcag atactacacc      1500
agaaccctgt accagttcca gttccaggag gccctgtgcc aggccgccaa gcacgagggc     1560
cccctgcaca agtgcgacat cagcaacagc accgaggccg ccagaagct gttcaacatg      1620
ctgagactgg gcaagagcga gccctggacc ctggccctgg agaacgtggt gggcgccaag     1680
aacatgaacg tgagaccct gctgaactac ttcgagcccc tgttcacctg gctgaaggac      1740
cagaacaaga acagcttcgt gggctggagc accgactgga gcccctacgc cgaccagagc     1800
atcaaggtga gaatcagcct gaagagcgcc ctgggcgaca aggcctacga gtggaacgac     1860
aacgagatgt acctgttcag aagcagcgtg gcctacgcca tgagacagta cttcctgaag     1920
gtgaagaacc agatgatcct gttcggcgag gaggacgtga gagtggccaa cctgaagccc     1980
agaatcagct tcaacttctt cgtgaccgcc cccaagaacg tgagcgacat catccccaga     2040
accgaggtgg agaaggccat cagaatgagc agaagcagaa tcaacgacgc cttcagactg     2100
aacgacaaca gcctggagtt cctgggcatc cagcccaccc tgggccccc caaccagccc     2160
cccgtgagcg acaagaccca cacctgcccc cctgccccg cccccgagct gctgggcggc      2220
cccagcgtgt tcctgttccc ccccaagccc aaggacaccc tgatgatcag cagaaccccc     2280
gaggtgacct gcgtggtggt ggacgtgagc cacgaggacc ccgaggtgaa gttcaactgg     2340
tacgtggacg gcgtggaggt gcacaacgcc aagaccaagc ccagagagga gcagtacaac     2400
agcacctaca gtggtgagc gtgctgaccg tgctgcacc aggactggct gaacggcaag       2460
gagtacaagt gcaaggtgag caacaaggcc ctgcccgccc ccatcgagaa gaccatcagc     2520
aaggccaagg gccagcccag agagcccag gtgtacaccc tgcccccag cagagacgag       2580
ctgaccaaga accaggtgag cctgacctgc ctggtgaagg gcttctaccc cagcgacatc     2640
gccgtggagt gggagagcaa cggccagccc gagaacaact acaagaccac ccccccgtg     2700
ctggacagcg acggcagctt cttcctgtac agcaagctga ccgtggacaa gagcagatgg     2760
cagcagggca acgtgttcag ctgcagcgtg atgcacgagg ccctgcacaa ccactacacc     2820
cagaagagcc tgagcctgag ccccggctga                                      2850
```